(12) United States Patent
Dubernet et al.

(10) Patent No.: US 9,115,073 B2
(45) Date of Patent: Aug. 25, 2015

(54) 1,3-DIPHENYLPROPANE DERIVATIVES, PREPARATIONS AND USES THEREOF

(71) Applicant: GENFIT, Loos (FR)

(72) Inventors: Mathieu Dubernet, Santes (FR); Jean-Francois Delhomel, Arras (FR); Karine Bertrand, Frelinghien (FR)

(73) Assignee: GENFIT, Loos (FR)

( * ) Notice: Subject to any disclaimer, the term of this patent is extended or adjusted under 35 U.S.C. 154(b) by 0 days.

(21) Appl. No.: 14/368,823

(22) PCT Filed: Dec. 28, 2012

(86) PCT No.: PCT/EP2012/077026
§ 371 (c)(1),
(2) Date: Jun. 26, 2014

(87) PCT Pub. No.: WO2013/098374
PCT Pub. Date: Jul. 4, 2013

(65) Prior Publication Data
US 2014/0350112 A1    Nov. 27, 2014

(30) Foreign Application Priority Data

Dec. 28, 2011    (EP) .................................... 11306790

(51) Int. Cl.
| | | |
|---|---|---|
| *A61K 31/19* | (2006.01) | |
| *C07C 59/72* | (2006.01) | |
| *C07C 323/19* | (2006.01) | |
| *C07C 323/62* | (2006.01) | |

(52) U.S. Cl.
CPC ............... *C07C 59/72* (2013.01); *C07C 323/19* (2013.01); *C07C 323/62* (2013.01); *C07C 2101/02* (2013.01); *C07C 2101/14* (2013.01); *C07C 2101/16* (2013.01)

(58) Field of Classification Search
USPC .......................................... 514/571; 562/468
See application file for complete search history.

(56) References Cited

U.S. PATENT DOCUMENTS 8,188,148 B2 *   5/2012   Delhomel et al. ............ 514/571
2010/0286276 A1  11/2010   Delhomel et al.

FOREIGN PATENT DOCUMENTS

| FR | 2902789 | 12/2007 |
| FR | 2910892 | 7/2008 |

OTHER PUBLICATIONS

Written Opinion in International Application No. PCT/EP2012/077026, Jan. 30, 2013, pp. 1-4.

* cited by examiner

*Primary Examiner* — Rei-Tsang Shiao
(74) *Attorney, Agent, or Firm* — Saliwanchik, Lloyd & Eisenschenk

(57) ABSTRACT

The present invention relates to novel 1,3-diphenylpropane derivatives, pharmaceutical compositions comprising the same and therapeutic uses thereof, in particular in the fields of human and animal health. The compounds according to the present invention have intrinsic PPAR agonist properties. They are therefore of particular interest in the treatment of metabolic and/or inflammatory diseases and particularly peripheral and central diseases associated with the metabolic syndrome, such as diverse forms of steatohepatitis, type 2 diabetes, diverse neurodegenerative disorders, such as Alzheimer's disease, Parkinson's disease and multiple sclerosis.

18 Claims, 4 Drawing Sheets

Figure 3

1,3-DIPHENYLPROPANE DERIVATIVES, PREPARATIONS AND USES THEREOF

CROSS-REFERENCE TO RELATED APPLICATION

This application is the U.S. national stage application of International Patent Application No. PCT/EP2012/077026, filed Dec. 28, 2012.

FIELD OF THE INVENTION

The present invention relates to novel 1,3-diphenylpropane derivatives, pharmaceutical compositions comprising the same and therapeutic uses thereof, in particular in the fields of human and animal health. The compounds according to the present invention have intrinsic PPAR agonist properties. They are therefore of particular interest in the treatment of metabolic and/or inflammatory diseases and particularly peripheral and central diseases associated with the metabolic syndrome, such as diverse forms of steatohepatitis, type 2 diabetes, diverse neurodegenerative disorders such as Alzheimer's disease, Parkinson's disease and multiple sclerosis.

TECHNICAL BACKGROUND

The peroxisome proliferator-activated receptors (PPARs) form a subfamily in the nuclear receptor superfamily. Three isoforms, encoded by separate genes, have been identified thus far: PPAR[gamma], PPAR[alpha], and PPAR[delta]. The PPARs are ligand-dependent transcription factors that regulate target gene expression by binding to specific peroxisome proliferator response elements (PPREs) in enhancer sites of regulated genes. PPARs possess a modular structure composed of functional domains that include a DNA binding domain (DBD) and a ligand binding domain (LBD). The DBD specifically binds PPREs in the regulatory region of PPAR-responsive genes. The LBD, located in the C-terminal half of the receptor contains the ligand-dependent activation domain, AF-2. Each receptor binds to its PPRE as a heterodimer with a retinoid X receptor (RXR). Upon binding of an agonist, the conformation of a PPAR is altered and stabilized such that a binding cleft, made up in part of the AF-2 domain, is created and recruitment of transcriptional coactivators occurs. Coactivators augment the ability of nuclear receptors to initiate the transcription process. The result of the agonist-induced PPAR-coactivator interaction at the PPRE is an increase in gene transcription. Downregulation of gene expression by PPARs appears to occur through indirect mechanisms (Berger J and Wagner J A, 2002).

PPAR[alpha] is expressed in numerous metabolically active tissues, including liver, kidney, heart, skeletal muscle, and brown fat. It is also present in monocytes, vascular endothelium, and vascular smooth muscle cells. Activation of PPAR[alpha] induces hepatic peroxisome proliferation, hepatomegaly, and hepatocarcinogenesis in rodents. These toxic effects are not observed in humans, although the same compounds activate PPAR[alpha] across species. There are two PPAR[gamma] isoforms expressed at the protein level in mouse and human, [gamma]1 and [gamma]2. They differ only in that the latter has 30 additional amino acids at its N terminus due to differential promoter usage within the same gene, and subsequent alternative RNA processing. PPAR [gamma]2 is expressed primarily in adipose tissue, while PPAR[gamma]1 is expressed in a broad range of tissues. PPAR[delta] is expressed in a wide range of tissues and cells with the highest levels of expression found in the digestive tract, heart, kidney, liver, adipose, and brain.

Kota provides a review of biological mechanisms involving PPARs that includes a discussion of the possibility of using PPAR modulators for treating a variety of conditions, including chronic inflammatory disorders such as atherosclerosis, arthritis and inflammatory bowel syndrome, retinal disorders associated with angiogenesis, increased fertility, and neurodegenerative diseases (Kota B P et al., 2005).

Yousef discusses the anti-inflammatory effects of PPAR [alpha], PPAR[gamma] and PPAR[delta] agonists, suggesting that PPAR agonists may have a role in treating neuronal diseases such as Alzheimer's disease, and autoimmune diseases such as inflammatory bowel disease and multiple sclerosis (Youssef J and Badr M, 2004). A potential role for PPAR agonists in the treatment of Alzheimer's disease has been described in Combs et al., (Combs C K et al., 2000), and such a role for PPAR agonists in Parkinson's disease is discussed in Breidert et al. (Breidert T et al., 2002). A potential related function of PPAR agonists in treatment of Alzheimer's disease, that of regulation of the APP-processing enzyme BACE, has been discussed by Sastre (Sastre M et al., 2003). These studies collectively indicate PPAR agonists may provide advantages in treating a variety of neurodegenerative diseases by acting through complementary mechanisms.

Discussion of the anti-inflammatory effects of PPAR agonists is also available in Feinstein et al., (Feinstein D L, 2004), in relation to multiple sclerosis and Alzheimer's disease; Patel et al., (Patel H J et al., 2003) in relation to chronic obstructive pulmonary disease (COPD) and asthma; Lovett-Racke et al., (Lovett-Racke A E et al., 2004) in relation to autoimmune disease; Malhotra et al., (Malhotra S et al., 2005) in relation to psoriasis; and Storer et al., (Storer P D et al., 2005) in relation to multiple sclerosis.

This wide range of roles for the PPARs that have been discovered suggest that PPAR[alpha], PPAR[gamma] and PPAR[delta] play a role in a wide range of events involving the vasculature, including atherosclerotic plaque formation and stability, thrombosis, vascular tone, angiogenesis, cancer, pregnancy, pulmonary disease, autoimmune disease, and neurological disorders.

The fibrates, amphipathic carboxylic acids that have been proven useful in the treatment of hypertriglyceridemia, are PPAR[alpha] ligands. Clofibrate and fenofibrate have been shown to activate PPARa with a 10-fold selectivity over PPAR[gamma]. Bezafibrate acts as a pan-agonist that shows similar potency on all three PPAR isoforms. Fibrates are known to regulate expression of genes (acyl CoA synthase, lipoprotein lipase, fatty acid transport protein and the like) relating to the metabolism of fatty acid and apolipoprotein (AI, AII, AV, CIII) genes involved in triglyceride (TG) and cholesterol metabolism, by activation of PPAR[alpha], decreases TG and LDL cholesterol and increases HDL cholesterol (Bocher V et al., 2002, Lefebvre P et al., 2006). Thus, fenofibrate is known to be highly effective as a therapeutic drug for hyperlipidemia. PPAR[alpha] also exerts anti-inflammatory and antiproliferative effects and prevents the proatherogenic effects of accumulation of cholesterol in macrophages by stimulating the outflow of cholesterol (Lefebvre P et al). Fenofibrate significantly reduced proteinuria, inflammatory cell recruitment and extracellular matrix (ECM) proteins deposition in the kidney of hypertensive SHR rats without apparent effect on blood pressure. A marked reduction of oxidative stress accompanied by reduced activity of renal NAD(P)H oxidase, increased activity of Cu/Zn SOD, and decreased phosphorylation of p38MAPK and JNK was detected in the kidney of fenofibrate treated SHR rat (Hou X et al., 2010). Fenofibrate significantly reduced superoxide production, protein oxidation and infarct size in the ischemic brain at 30 minutes after reperfusion (Wang G et al., 2010). Fenofibrate administration significantly decreased the cerebral infarct volume and reduced microglial activation and neutrophil infiltration into the ischaemic zone (Ouk T et al., 2009). This effect was associated with partial prevention of post-ischaemic endothelial dysfunction.

The finding that the thiazolidinediones mediate their therapeutic effects through direct interactions with PPAR[gamma] established this target as a key regulator of glucose and lipid homeostasis. PPAR[gamma] improves insulin resistance and thereby has a hypoglycemic effect. Ligands known for PPAR[gamma] include synthetic compounds such as unsaturated fatty acids (e.g., [alpha]-linolenic acid, eicosapentaenoic acid, docosahexaenoic acid) and thiazolidine-type antidiabetic drugs (e.g., troglitazone, pioglitazone, rosiglitazone) (Bhatia V and Viswanathan P, 2006, Nagy L et al., 1998). These ligands are known to suppress hyperplasia of large adipocytes and to increase the number of insulin-sensitive small adipocytes, so that they improve insulin resistance and thereby reduce blood glucose levels (Tontonoz P and Spiegelman B M, 2008, Walczak R and Tontonoz P, 2002).

One of the earliest findings associating PPARs and macrophages was that PPAR[gamma] was highly expressed in macrophage-derived foam cells of human and murine atherosclerotic lesions. Subsequently, it has been demonstrated that PPAR[gamma] is expressed in human and murine monocytes/macrophages. Functionally, PPAR[gamma] has been shown to play a role in the differentiation and activation of monocytes and in the regulation of inflammatory activities (Chawla A et al., 2001, Li A C et al., 2004). Many studies have demonstrated that PPAR[gamma] ligands inhibit macrophage-mediated inflammatory responses. Thiazolidinediones have been found to inhibit the secretion of many of these mediators (including gelatinase B, IL-6, TNF-a, and IL-1) and also to reduce the induced expression of inducible NOS (iNOS) and the transcription of the scavenger receptor (Chawla A et al., 2001, Li A C et al., 2004).

The relevance of PPAR[gamma] has been studied in several human autoimmune diseases and animal models of autoimmune diseases. Kawahito et al. demonstrated that synovial tissue expressed PPAR[gamma] in patients with rheumatoid arthritis (Kawahito Y et al., 2000). PPAR[gamma] was found to be highly expressed in macrophages, and modest expression was noted in synovial-lining fibroblasts and ECs. Activation of PPAR[gamma] by 15d-PGJ2 and troglitazone induced RA synoviocyte apoptosis in vitro. It has been suggested that PPAR[gamma] is functionally relevant in freshly isolated T cells or becomes functionally relevant early in activation. In these studies, it was also demonstrated that the two ligands for PPAR[gamma] mediated inhibition of IL-2 secretion by the T-cell clones and did not inhibit IL-2-induced proliferation of such clones. Several studies have investigated the role of PPAR[gamma] ligands in modifying animal models of autoimmune diseases. Su et al. showed that in a mouse model of inflammatory bowel disease, thiazolidinediones markedly reduced colonic inflammation (Su C G et al., 1999). It has been proposed that this effect might be a result of a direct effect on colonic epithelial cells, which express high levels of PPAR[gamma] and can produce inflammatory cytokines. Kawahito et al. demonstrated that intraperitoneal administration of the PPAR[gamma] ligands, 15d-PGJ2 and troglitazone, ameliorated adjuvant-induced arthritis (Kawahito Y et al., 2000). Niino and Feinstein examined the effect of a thiazolidinedione on experimental allergic encephalomyelitis and found that this treatment attenuated the inflammation and decreased the clinical symptoms in this mouse model of multiple sclerosis (Feinstein D L et al., 2002, Niino M et al., 2001).

Alzheimer's disease (AD) is characterized by the extracellular deposition of beta-amyloid fibrils within the brain and the activation of microglial cells associated with the amyloid plaque. The activated microglia subsequently secrete a diverse range of inflammatory products. Kitamura et al. assessed the occurrence of PPAR[gamma] and COX-1, COX-2, in normal and AD brains using specific antibodies and found increased expression of these moieties in AD brains (Kitamura Y et al., 1999). Nonsteroidal, anti-inflammatory drugs (NSAIDs) have been shown to be efficacious in reducing the incidence and risk of AD and in delaying disease progression. Combs et al. demonstrated that NSAIDs, thiazolidinediones, and PGJ2, all of which are PPAR[gamma] agonists, inhibited the beta-amyloid-stimulated secretion of inflammatory products by microglia and monocytes. PPAR[gamma] agonists were shown to inhibit the beta-amyloid-stimulated expression of the genes for IL-6 and TNFa and the expression of COX-2 (Combs C K et al., 2000). Heneka et al. demonstrated that microinjection of LPS and IFN-a into rat cerebellum induced iNOS expression in cerebellar granule cells and subsequent cell death (Heneka M T et al., 2000). Coinjection of PPAR[gamma] agonists (including troglitazone and 15d-PGJ2) reduced iNOS expression and cell death, whereas coinjection of a selective COX inhibitor had no effect. Overall, work in AD seems to suggest that PPAR[gamma] agonists can modulate inflammatory responses in the brain and that NSAIDs may be helpful in AD as a result of their effect on PPAR[gamma].

The low dose combination of fenofibrate and rosiglitazone was more effective in attenuating the diabetes-induced experimental nephropathy and renal oxidative stress as compared to treatment with either drug alone or lisinopril (Arora M K et al., 2010). The concurrent administration of fenofibrate and rosiglitazone at low doses may have prevented the development of diabetes induced nephropathy by reducing the lipid alteration, decreasing the renal oxidative stress and certainly providing the direct nephroprotective action.

PPAR ligands have also been identified as dual PPAR[gamma]/[alpha] agonists. By virtue of the additional PPAR[alpha] agonist activity, this class of compounds has potent lipid-altering efficacy in addition to antihyperglycemic activity in animal models of lipid disorders. KRP-297 is an example of a TZD dual PPAR[gamma]/[alpha] agonist (Murakami K et al., 1998); furthermore DRF-2725 and AZ-242 are non-TZD dual PPAR[gamma]/[alpha] agonists (Cronet P et al., 2001, Lohray B B et al., 2001).

Recently, potent PPAR[delta] ligands have been published allowing a better understanding of its function in lipid metabolism (Barak Y et al., 2002, Oliver W R, Jr. et al., 2001, Tanaka T et al., 2003, Wang Y X et al., 2003). The main effect of these compounds in db/db mice (Leibowitz M D et al., 2000) and obese rhesus monkeys (Oliver W R, Jr. et al., 2001) was an increase of high density lipoprotein cholesterol (HDL-C) and a decrease in triglycerides with little effect on glucose (although insulin levels were decreased in monkeys). HDL-C serves to remove cholesterol from peripheral cells through a process called reverse cholesterol transport. The first and rate-limiting step, which is a transfer of cellular cholesterol and phospholipids to the apolipoprotein A-I component of HDL3 is mediated by the ATP binding cassette transporter A1 (ABCA1) (Lawn R M et al., 1999). PPAR[delta] activation appears to increase HDL-C through transcriptional regulation of ABCA1 (Oliver W R, Jr. et al., 2001). Therefore, by inducing ABCA1 mRNA in macrophages, PPAR[delta] agonists could increase HDL-C levels in patients and remove excess cholesterol from lipid-laden macrophages, one of the major players in atherosclerotic lesion development. This would be an alternative therapy to the statin drugs, which show little effect on HDL-C and mainly decrease LDL-C or the fibrates, the only marketed PPAR[alpha] agonists, having low potency and inducing only modest HDL-C elevations. In addition, like the fibrates, PPAR[delta] agonists have the potential to also reduce triglycerides, an additional risk factor for cardiovascular disease.

PPAR[delta] is highly expressed in skeletal muscle cells, and further PPAR[delta] is involved in the expression of genes associated with fatty acid metabolism and has the function of stimulating fatty acid metabolism in skeletal muscle cells or fat tissue. PPAR[delta] conditional knock-out mice, engineered to lack receptor expression specifically in the myogenic cells, had 40% fewer satellite cells than their wild-type littermates, and these satellite cells exhibited reduced growth kinetics and proliferation in vitro (Angione A R et al., 2011). Furthermore, regeneration of PPAR[delta] muscles was impaired after cardiotoxin-induced injury. These results support a function of PPAR[delta] in regulating skeletal muscle metabolism and insulin sensitivity. In-line with these findings, transgenic mice designed to overexpress PPAR[delta] in their skeletal muscle are less likely to develop high-fat diet-induced obesity or insulin resistance, and their adipocytes become smaller in size.

By various other mechanisms, PPAR[delta] agonists are effective at preventing, reversing, or treating other types of inflammations and particularly diseases linked to lung inflammation. Using intravital microscopy in the mouse cremasteric microcirculation, Piqueras et al., have shown that activation of PPAR[delta] by its selective ligand GW501516 inhibited TNF-alpha induced leukocyte rolling flux, adhesion, and emigration in a dose-dependent manner (Piqueras L et al., 2009). Moreover, PPAR[delta] agonists reduced the expression of adhesion molecules such as ICAM-1, VCAM-1, and E-selectin in the cremasteric postcapillary venules. Similarly, rolling and adhesion of hPMNs under physiological flow on TNF-alpha-activated HUVECs were also inhibited markedly by GW501516. These inhibitory responses of GW501516 on activated endothelium were accompanied by a reduction in TNF-alpha induced endothelial GRO-release and VCAM-1, E-selectin, and ICAM-1 mRNA expression. Taken together, these results show that PPAR [delta] modulates acute inflammation in vivo and in vitro under flow by targeting the neutrophil-endothelial cell (Piqueras L et al., 2009).

Renal ischemia, also called nephric ischemia, is the deficiency of blood in one or both kidneys, or nephrons, usually due to functional constriction or actual obstruction of a blood vessel. Acute renal ischemia is associated with significant morbidity and mortality. There has been little progress in treating the disease over the last 50 years. Currently dialysis is the only effective therapy. A few reports have proposed a relationship between the activation of PPAR[alpha] (Portilla D et al., 2000), PPAR[gamma] (Sivarajah A et al., 2003) and PPAR[delta] (Letavernier E et al., 2005) and protection from acute renal ischemia. It has been suggested that the protective effect of PPAR[delta] may be due to its activation of the anti-apoptotic Akt signaling pathway and by promoting increased spreading of tubular epithelial cells.

Examples of known PPAR delta agonists variously useful for hyperlipidemia, diabetes, or atherosclerosis include L-165041 (Leibowitz M D et al., 2000) and GW501516 (Oliver W R, Jr. et al., 2001). There is a further need for new PPAR delta agonists for the treatment of diabetes, nephropathy, neuropathy, retinopathy, polycystic ovary syndrome, hypertension, ischemia, stroke, irritable bowel disorder, inflammation, cataract, cardiovascular diseases, metabolic syndrome, X syndrome, hyper-LDL-cholesterolemia, dyslipidemia (including hypertriglyceridemia, hypercholesterolemia, mixed hyperlipidemia, and hypo-HDL-cholesterolemia), atherosclerosis, obesity, and other disorders related to lipid metabolism and energy homeostasis complications thereof.

The old and well known lipid-lowering fibric acid derivative bezafibrate is the first clinically tested panPPAR activator. Bezafibrate leads to considerable raising of HDL cholesterol and reduces triglycerides, improves insulin sensitivity and reduces blood glucose level, significantly lowering the incidence of cardiovascular events and new diabetes in patients with features of metabolic syndrome (Tenenbaum A et al., 2005). Clinical evidences obtained from bezafibrate-based studies strongly support the concept of pan-PPAR therapeutic approach to conditions which comprise the metabolic syndrome.

Both bezafibrate and GW501516 inhibited the methionine- and choline-deficient (MCD)-diet-induced elevations of hepatic triglyceride and thiobarbituric acid-reactants contents and the histopathological increases in fatty droplets within hepatocytes, liver inflammation and number of activated hepatic stellate cells (Nagasawa T et al., 2006). In this model, both ligands increased the levels of hepatic mRNAs associated with fatty acid beta-oxidation and reduced the levels of those associated with inflammatory cytokines or chemokine. In addition, bezafibrate characteristically reduced the elevation in the level of plasma ALT, but enhanced that in plasma adiponectin and increased the mRNA expression levels of its receptors. These results suggest that panPPAR activators may improve non-alcoholic steatohepatitis.

The results of the Bezafibrate Infarction Prevention (BIP) Study demonstrated that in diabetic patients, bezafibrate administration over two years period prevented a progressive decline of beta cell function and an increase of insulin resistance (Tenenbaum H et al., 2007). Bezafibrate therapy in the BIP trial was also associated with significant long-term cardiovascular protection despite the unbalanced usage of non-study lipid lowering drugs during the course of the trial (Goldenberg I et al., 2008). The results of the 16-year mortality follow-up of the BIP trial demonstrated that patients allocated to bezafibrate therapy experienced a significant 11% reduction in the risk of long-term mortality compared with placebo-allocated patients (Goldenberg I et al., 2009).

SUMMARY OF THE INVENTION

The present invention provides novel compounds, derived from 1,3-diphenylpropane, having the following general formula:

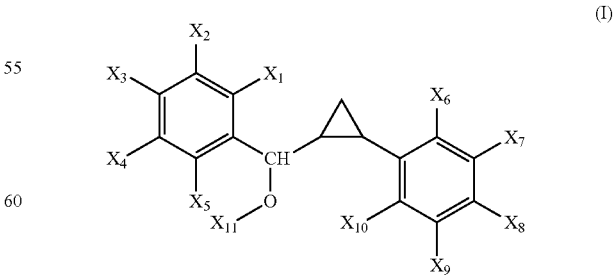

(I)

in which:
X1 represents a halogen atom, a hydrogen atom, a R1 or G1-R1 group;

X2 represents a halogen atom, a hydrogen atom, a R2 or G2-R2 group;
X3 represents a halogen atom, a hydrogen atom, a R3 or G3-R3 group;
X4 represents a halogen atom, a hydrogen atom, a R4 or G4-R4 group;
X5 represents a halogen atom, a hydrogen atom, a R5 or G5-R5 group;
X6, X7, X9 and X10, identical or different, represent an halogen atom, a hydrogen atom, or an alkyl group;
X8 represents a G8-R8 group;
wherein R1, R2, R3, R4 and R5, identical or different, represent an alkyl group, preferably an halogenated alkyl group;
R8 represents an alkyl group substituted by at least one COOR12 group;
R12 represents an atom of hydrogen or an alkyl group;
G1, G2, G3, G4, G5, and G8, identical or different, representing an atom of oxygen or sulfur;
X11 represents an alkyl group, substituted or not by an aryl or a cycloalkyl group.

The compounds according to the present invention have intrinsic PPAR agonist properties.

The compounds of the invention are therefore of particular interest in the treatment of metabolic and/or inflammatory diseases, such as: overweight condition, bulimia, anorexia nervosa, hyperlipidemia, dyslipidemia, hypoalphalipoproteinemia, hypertriglyceridemia, hypercholesterolemia, low HDL, metabolic syndrome, non-alcoholic fatty liver disease (NAFLD), non-alcoholic steatohepatitis (NASH), diseases associated with hepatic fibrosis, such as primary biliary cirrhosis, viral hepatitis, or drug-induced hepatitis, alcoholic liver disease, type 2 diabetes, type 1 diabetes, hyperinsulinemia, impaired glucose tolerance, insulin resistance, a diabetic complication of neuropathy, nephropathy, retinopathy, diabetic foot ulcer or cataracts, hypertension, coronary heart disease, heart failure, congestive heart failure, atherosclerosis, arteriosclerosis, stroke, cerebrovascular disease, myocardial infarction, peripheral vascular disease, vitiligo, uveitis, pemphigus foliaceus, inclusion body myositis, polymyositis, dermatomyositis, scleroderma, Grave's disease, Hashimoto's disease, chronic graft versus host disease, rheumatoid arthritis, inflammatory bowel syndrome, Crohn's disease, systemic lupus erythematosis, Sjogren's syndrome, multiple sclerosis, asthma, chronic obstructive pulmonary disease, polycystic kidney disease, polycystic ovary syndrome, pancreatitis, nephritis, hepatitis, eczema, psoriasis, dermatitis, impaired wound healing, Alzheimer's disease, Parkinson's disease, amyotrophic lateral sclerosis, spinal cord injury, acute disseminated encephalomyelitis, Guillain-Barre syndrome, thrombosis, infarction of the large or small intestine, renal insufficiency, erectile dysfunction, urinary incontinence, neurogenic bladder, ophthalmic inflammation, macular degeneration, pathologic neovascularization, HCV infection, HIV infection, or Helicobacter pylori infection.

They are particularly useful in the treatment of peripheral and/or central diseases associated with the metabolic syndrome, such as diverse forms of steatohepatitis, type 2 diabetes, diverse neurodegenerative disorders, such as Alzheimer's disease, Parkinson's disease or multiple sclerosis.

DETAILED DESCRIPTION OF THE INVENTION

In the context of the invention, the term "alkyl" designates a hydrocarbon radical that is saturated, linear, branched, or cyclic, halogenated or not halogenated, having particularly from 1 to 24, preferably 1, 2, 3, 4, 5, 6, 7, 8, 9, or 10, carbon atoms, more preferably from 1 to 4 carbon atoms. For instance, the alkyl group can be methyl, ethyl, n-propyl, isopropyl, n-butyl, isobutyl, tertiobutyl, sec-butyl, pentyl, neopentyl, n-hexyl, or cyclohexyl group.

The term "cycloalkyl" designates a specific alkyl group as defined above and forms at least one cycle. The cycloalkyl group has more specifically from 3 to 8 carbon atoms, e.g.: cyclopropyl, cyclobutyl, cyclopentyl, cyclohexyl, cycloheptyl, and cyclooctyl groups.

The term "aryl" refers to aromatic groups comprising preferably from 5 to 14 carbon atoms, advantageously 6 to 14 carbon atoms, optionally interrupted by one or several heteroatoms selected among N, O, S or P (more specifically called "heteroaryl"). They are generally mono- or bi-cyclical and comprise advantageously from 6 to 14 carbon atoms, such as phenyl, α-naphtyl, β-naphtyl, anthracenyl or fluorenyl.

By halogen atom, an atom of bromine, chlorine, fluorine or iodine is understood.

A halogenated alkyl radical is an alkyl radical as defined above which comprises at least one halogen atom or is totally halogenated (perhalogenated), like trifluoromethyl.

The invention also includes pharmaceutically acceptable salts, hydrates and/or solvates of a compound of General Formula (I). The invention further relates to metabolites or prodrugs of a compound of General Formula (I). The invention further includes optical and geometrical isomers of a compound of General Formula (I), and mixtures thereof. The compounds of the present invention have one or more asymmetric centers and it is intended that stereoisomers (optical isomers), as separated, pure or partially purified stereoisomers or racemic mixtures thereof are included in the scope of the invention.

In a particular embodiment, when at least one of X1, X2, X3, X4 and X5 represents R1, R2, R3, R4 and R5 respectively, then said R1, R2, R3, R4 or R5 is C1-C4, halogenated or not, alkyl groups, more specifically a methyl or trifluoromethyl group.

In a particular embodiment, when at least one of X1, X2, X3, X4 and X5 represents G1-R1, G2-R2, G3-R3, G4-R4 and G5-R5 respectively, then said R1, R2, R3, R4 or R5 is a C1-C4, halogenated or not, alkyl group, more specifically a methyl or trifluoromethyl group.

In an aspect of the invention, the compounds are of formula (I) wherein at least three, more particularly three or four, out of the X1, X2, X3, X4 and X5 groups are hydrogen atom, preferably X2, X4 and X5 are hydrogen atoms or X1, X2, X4 and X5 are hydrogen atoms.

In another particular embodiment, X1, X2, X3, X4 and X5 groups represent R1, R2, R3, R4 and R5, respectively, and said R1, R2, R3, R4 and R5 are C1-C4, halogenated or not, alkyl groups, more specifically a methyl or trifluoromethyl group.

One particular aspect of the invention concerns compounds of general formula (I) in which X3 represents a halogen atom (e.g., F or Br), a R3 or G3-R3 group and X1 represents a halogen atom (e.g., F or Br) or more particularly a hydrogen atom. According to said embodiment, the compounds of the invention are more particularly of formula (I) wherein X2, X4 and X5 are hydrogen atoms.

Another particular aspect of the invention concerns compounds of general formula (I) in which X1 represents a halogen atom (e.g., F or Br), a R1 or G1-R1 group and X3 represents a halogen atom (e.g., F or Br) or more particularly a hydrogen atom. According to said embodiment, the compounds of the invention are more particularly of formula (I) wherein X2, X4 and X5 are hydrogen atoms.

According to the invention or the above described specific embodiments, when X3 or X1 is R3 or R1 group, respectively, then said R3 or R1 group is preferably a methyl or trifluoromethyl group.

According to the invention or the above described specific embodiments, when X3 or X1 is G3-R3 or G1-R1 group, respectively, then said G3-R3 or G1-R1 group is preferably a methoxy (—OCH3), methylthio (—SCH3), trifluoromethoxy (—OCF3) or trifluoromethylthio (—SCF3).

Another particular aspect of the invention concerns compounds of general formula (I) in which at least one of X7 and X9 group is not an hydrogen atom.

According to a particular aspect of the invention, the compounds are of formula (I) wherein X6, X7, X9 and X10 represent independently an atom of hydrogen, a halogen atom or an alkyl group; with at least one of X7 and X9 group is not an hydrogen atom. Consequently, X7 is hydrogen and X9 is an alkyl group or a halogen atom, or X9 is hydrogen and X7 is an alkyl group or a halogen atom, or both X7 and X9, identical or different, are an alkyl group and/or a halogen atom. When X7 and/or X9 is an alkyl group, said alkyl group is preferably a (C1-C4)alkyl group, such as methyl group.

In an aspect of the invention, the compounds are of formula (I) wherein X6 and X10 represent independently a halogen atom, a (C1-C4)alkyl group, or more preferably a hydrogen atom. When at least one of X6 and X10 represents a (C1-C4) alkyl group, then said alkyl group is preferably a methyl or trifluoromethyl group.

Another particular aspect of the invention concerns compounds of general formula (I) in which either X6 and X7 are halogen atoms (preferably chlorine) and X9 and X10 are hydrogen atoms or X9 and X10 are halogen atoms (preferably chlorine) and X6 and X7 are hydrogen atoms.

Another particular aspect of the invention concerns compounds of general formula (I) in which G8 is an oxygen atom.

Another particular aspect of the invention concerns compounds of general formula (I) in which R8 is a (C1-C4)alkyl group. The (C1-C4)alkyl group is preferably linear or more preferably branched. Examples of R8 include, but are not limited to: —CH(CH3)-, and —C(CH3)2-.

According to a particular aspect of the invention, R12 is an hydrogen or a (C1-C4)alkyl group. The (C1-C4)alkyl group is linear or preferably branched. It can be for instance methyl, ethyl, n-propyl, n-butyl, isobutyl, preferably isopropyl or tertiobutyl.

Another particular aspect of the invention concerns compounds of general formula (I) in which X11 represents a (C1-C4)alkyl group, linear or branched, substituted or not by an aryl or cycloalkyl group. Preferably, the aryl group is a phenyl group. Preferably, the cycloalkyl is a cyclohexyl group.

According to a particular aspect of the invention, X11 is a linear (C1-C4)alkyl group, such as methyl, ethyl, n-propyl, or n-butyl group.

A list of preferred compounds of General Formula (I) that present specific substituent groups according to further specific embodiments of the invention are shown in FIG. 3 and includes:

|  | Stereoisomery | | |
|---|---|---|---|
| Cpd N° | Racemate | Enantiopure | Name |
| 1-1 | ✓ | | 2-(4-(2-(methoxy(4- |
| 1-2 | ✓ | | bromophenyl)methyl)cyclopropyl)-2,6-dimethylphenoxy)-2-methylpropanoic acid |
| 2-1 | ✓ | | 2-(4-(2-(methoxy(4-methylphenyl)methyl)cyclopropyl)-2,6-dimethylphenoxy)-2-methylpropanoic acid |
| 3-1 | ✓ | | 2-(4-(2-(methoxy(4- |
| 3-2 | | ✓ | (methylthio)phenyl)methyl)cyclopropyl)-2,6-dimethylphenoxy)-2-methylpropanoic acid |
| 4-1 | ✓ | | 2-(4-(2-(methoxy(4- |
| 4-2 | | ✓ | (trifluoromethyl)phenyl)methyl)cyclopropyl)-2,6-dimethylphenoxy)-2-methylpropanoic acid |
| 5-1 | ✓ | | 2-(4-(2-(butyloxy(4- |
| 5-2 | | ✓ | (trifluoromethoxy)phenyl)methyl)cyclopropyl)-2,6-dimethylphenoxy)-2-methylpropanoic acid |
| 6-1 | ✓ | | 2-(4-(2-(cyclohexylethyloxy(4- |
| 6-2 | | ✓ | (trifluoromethoxy)phenyl)methyl)cyclopropyl)-2,6-dimethylphenoxy)-2-methylpropanoic acid |
| 7-1 | ✓ | | 2-(4-(2-(methoxy(4- |
| 7-2 | | ✓ | (trifluoromethoxy)phenyl)methyl)cyclopropyl)-2-methylphenoxy)-2-methylpropanoic acid |
| 8-1 | ✓ | | 2-(4-(2-(methoxy(4- |
| 8-2 | | ✓ | (propyloxy)phenyl)methyl)cyclopropyl)-2,6-dimethylphenoxy)-2-methylpropanoic acid |
| 9-1 | ✓ | | 2-(4-(2-(methoxy(4-(trifluoromethylthio)phenyl)methyl)cyclopropyl)-2,6-dimethylphenoxy)-2-methylpropanoic acid |
| 10-1 | ✓ | | 2-(4-(2-(ethoxy(4- |
| 10-2 | | ✓ | (trifluoromethoxy)phenyl)methyl)cyclopropyl)-2,6-dimethylphenoxy)-2-methylpropanoic acid |
| 11-1 | ✓ | | 2-(4-(2-(benzyloxy(4- |
| 11-2 | | ✓ | (trifluoromethoxy)phenyl)methyl)cyclopropyl)-2,6-dimethylphenoxy)-2-methylpropanoic acid |
| 12-1 | ✓ | | 2-(4-(2-(methoxy(2-fluoro-4- |
| 12-2 | | ✓ | (trifluoromethyl)phenyl)methyl)cyclopropyl)-2,6-dimethylphenoxy)-2-methylpropanoic acid |
| 13-1 | ✓ | | 2-(4-(2-(methoxy(2- |
| 13-2 | | ✓ | (trifluoromethyloxy)phenyl)methyl)cyclopropyl)-2,6-dimethylphenoxy)-2-methylpropanoic acid |
| 14-1 | ✓ | | 2-(4-(2-(methoxy(4- |

-continued

| Cpd N° | Stereoisomery Racemate | Enantiopure | Name |
|---|---|---|---|
| 14-2 | ✓ | | (trifluoromethoxy)phenyl)methyl)cyclopropyl)-2,6-dimethylphenoxy)-2-methylpropanoic acid |
| 14-1-1 | | ✓ | |
| 14-1-2 | | ✓ | |
| 14-2-1 | | ✓ | |
| 14-2-2 | | ✓ | |
| 15-1 | ✓ | | 2-(2-isopropyl-4-(2-(methoxy(4-(trifluoromethoxy)phenyl)methyl)cyclopropyl)phenoxy)-2-methylpropanoic acid |
| 15-2 | ✓ | | |
| 16-1 | ✓ | | 2-(4-(2-((2,4-bis(trifluoromethyl)phenyl)(methoxy)methyl)cyclopropyl)-2,6-dimethylphenoxy)-2-methylpropanoic acid |
| 16-2 | ✓ | | |
| 17-1 | ✓ | | 2-(4-(2-(methoxy(2-methoxy-4-(trifluoromethoxy)phenyl)methyl)cyclopropyl)-2,6-dimethylphenoxy)-2-methylpropanoic acid |
| 18-1 | ✓ | | 2-(4-(2-((2-(hexyloxy)phenyl)(methoxy)methyl)cyclopropyl)-2,6-dimethylphenoxy)-2-methylpropanoic acid |
| 19-1 | ✓ | | 2-(2-bromo-4-(2-(methoxy(4-(trifluoromethoxy)phenyl)methyl)cyclopropyl)phenoxy)-2-methylpropanoic acid |
| 20-1 | ✓ | | 2-(2,6-difluoro-4-(2-(methoxy(4-(trifluoromethoxy)phenyl)methyl)cyclopropyl)phenoxy)-2-methylpropanoic acid |
| 21-1 | ✓ | | 2-(2-cyclopropyl-4-(2-(methoxy(4-(trifluoromethoxy)phenyl)methyl)cyclopropyl)phenoxy)-2-methylpropanoic acid |

In a particular aspect, the invention concerns 2-(4-(2-(methoxy(4-(trifluoromethoxy)phenyl)methyl)cyclopropyl)-2,6-dimethylphenoxy)-2-methylpropanoic acid.

As mentioned before, the compounds of the present invention include their stereoisomers (diastereoisomers, enantiomers), pure or mixed, racemic forms, their geometric isomers, their salts, their hydrates, their solvates, their solid forms, and mixtures thereof.

The compounds according to the invention comprise several asymmetrical centers. The present invention includes stereoisomers (diastereoisomers, enantiomers), pure or mixed, as well as racemic forms and geometrical isomers. When an enantiomerically pure (or enriched) mixture is desired, it can be obtained either by purification of the final product or chiral intermediates, or by synthetic methods known by the person skilled in the art such as asymmetric synthesis, enzymatic resolution, resolution via diastereoisomeric salt formation or chromatography using a chiral stationary phase.

This invention also concerns "pharmaceutically acceptable" salts of compounds according to the invention. Generally, this term designates slightly- or non-toxic salts obtained from organic or inorganic bases or acids. These salts may be obtained during the final purification step of the compound according to the invention or by incorporating the salt into the purified compound.

Some compounds according to the invention and their salts could be stable in several solid forms. The present invention includes all the solid forms of the compounds according to the invention which includes amorphous, polymorphous, mono- and polycrystalline forms.

The compounds according to the invention can exist in non-solvated or solvated form, for example with pharmaceutically acceptable solvents such as water (hydrates) or ethanol.

Compounds according to the invention labeled with one or more isotopes are also included in the invention: these compounds are structurally identical but different by the fact that at least one atom of the structure is replaced by an isotope (radioactive or not). Examples of isotopes that can be included in the structure of the compounds according to the invention can be chosen among hydrogen, carbon, oxygen, and sulfur such as $^{2}H$, $^{3}H$, $^{13}C$, $^{14}C$, $^{18}O$, $^{17}O$, $^{35}S$ respectively. Radioactive isotopes are particularly preferable since they are easy to prepare and detect within the scope of in vivo bioavailability studies of the substances. Heavy isotopes (such as $^{2}H$) are particularly preferred because of their use as internal standards in analytical studies.

The present invention also concerns a method for the preparation of compounds of general formula (I) as previously defined. The methods of the present invention are detailed in the figures.

The procedures of the syntheses can be particularly those described under "examples" in this invention.

The resulting compounds can be isolated by classic methods of one of ordinary skill in the art. They could then be used, for example, as medicines or cosmetic products.

The present invention is also directed to compounds such as above described as medicines.

Another subject-matter of the present invention concerns a pharmaceutical composition comprising, in a pharmaceutically acceptable support, at least one compound as above described, optionally in association with one or several other therapeutic and/or cosmetic active constituents.

It preferably concerns a compound of the invention or the pharmaceutical composition for use in the treatment of metabolic and/or inflammatory diseases. Metabolic and/or inflammatory diseases are more particularly selected from overweight condition, bulimia, anorexia nervosa, hyperlipidemia, dyslipidemia, hypoalphalipoproteinemia, hypertriglyceridemia, hypercholesterolemia, low HDL, metabolic syndrome, non-alcoholic fatty liver disease (NAFLD), non-alcoholic steatohepatitis (NASH), diseases associated with hepatic fibrosis, such as primary biliary cirrhosis, viral hepatitis, or drug-induced hepatitis, alcoholic liver disease, type 2 diabetes, type 1 diabetes, hyperinsulinemia, impaired glucose tolerance, insulin resistance, a diabetic complication of neuropathy, nephropathy, retinopathy, diabetic foot ulcer or cataracts, hypertension, coronary heart disease, heart failure, congestive heart failure, atherosclerosis, arteriosclerosis, stroke, cerebrovascular disease, myocardial infarction, peripheral vascular disease, vitiligo, uveitis, pemphigus foliaceus, inclusion body myositis, polymyositis, dermatomyositis, scleroderma, Grave's disease, Hashimoto's disease, chronic graft versus host disease, rheumatoid arthritis, inflammatory bowel syndrome, Crohn's disease, systemic lupus erythematosis, Sjogren's syndrome, multiple sclerosis, asthma, chronic obstructive pulmonary disease, polycystic kidney disease, polycystic ovary syndrome, pancreatitis, nephritis, hepatitis, eczema, psoriasis, dermatitis, impaired wound healing, Alzheimer's disease, Parkinson's disease, amyotrophic lateral sclerosis, spinal cord injury, acute disseminated encephalomyelitis, Guillain-Barre syndrome, thrombosis, infarction of the large or small intestine, renal insufficiency, erectile dysfunction, urinary incontinence, neurogenic bladder, ophthalmic inflammation, macular degeneration, pathologic neovascularization, HCV infection, HIV infection, or Helicobacter pylori infection.

More specifically, it concerns a compound of the invention or the pharmaceutical composition for use in the treatment of peripheral and/or central diseases associated with the metabolic syndrome, such as diverse forms of steatohepatitis, type 2 diabetes, diverse neurodegenerative disorders, such as Alzheimer's disease and Parkinson's disease.

The compound or pharmaceutical composition according to the invention is preferably used for treating diabetes and/or neurodegenerative disorders.

It is preferably a compound or a pharmaceutical composition of the invention for use in the treatment of neurodegenerative pathologies, more specifically Alzheimer's or Parkinson's disease.

Another subject-matter of the invention concerns a nutritional composition including at least one compound as above described.

Another subject-matter of the invention concerns the use of at least one compound as previously described for the preparation of pharmaceutical compositions intended for the treatment of metabolic and/or inflammatory diseases, such as: overweight condition, bulimia, anorexia nervosa, hyperlipidemia, dyslipidemia, hypoalphalipoproteinemia, hypertriglyceridemia, hypercholesterolemia, low HDL, metabolic syndrome, non-alcoholic fatty liver disease (NAFLD), non-alcoholic steatohepatitis (NASH), diseases associated with hepatic fibrosis, such as primary biliary cirrhosis, viral hepatitis, or drug-induced hepatitis, alcoholic liver disease, type 2 diabetes, type 1 diabetes, hyperinsulinemia, impaired glucose tolerance, insulin resistance, a diabetic complication of neuropathy, nephropathy, retinopathy, diabetic foot ulcer or cataracts, hypertension, coronary heart disease, heart failure, congestive heart failure, atherosclerosis, arteriosclerosis, stroke, cerebrovascular disease, myocardial infarction, peripheral vascular disease, vitiligo, uveitis, pemphigus foliaceus, inclusion body myositis, polymyositis, dermatomyositis, scleroderma, Grave's disease, Hashimoto's disease, chronic graft versus host disease, rheumatoid arthritis, inflammatory bowel syndrome, Crohn's disease, systemic lupus erythematosis, Sjogren's syndrome, multiple sclerosis, asthma, chronic obstructive pulmonary disease, polycystic kidney disease, polycystic ovary syndrome, pancreatitis, nephritis, hepatitis, eczema, psoriasis, dermatitis, impaired wound healing, Alzheimer's disease, Parkinson's disease, amyotrophic lateral sclerosis, spinal cord injury, acute disseminated encephalomyelitis, Guillain-Barre syndrome, thrombosis, infarction of the large or small intestine, renal insufficiency, erectile dysfunction, urinary incontinence, neurogenic bladder, ophthalmic inflammation, macular degeneration, pathologic neovascularization, HCV infection, HIV infection, or Helicobacter pylori infection. More specifically, the subject-matter of the invention concerns the use of at least one compound previously described for the preparation of pharmaceutical compositions intended for treating diabetes or a neurodegenerative disorder, in particular Alzheimer's, Parkinson's disease or multiple sclerosis.

For example, the compounds according to the invention may be advantageously administered in combination with other therapeutic and/or cosmetic agents, currently available in the market or in development.

The invention also concerns a method for treating a metabolic and/or inflammatory disease, such as the ones identified above, comprising the administration to a subject, in particular a human, of an effective amount of a compound or a pharmaceutical composition as above-defined.

Within the context of the invention, the term "an effective amount" refers to an amount of the compound sufficient to produce the desired biological result. Within the context of the invention, the term "subject" means a mammal and more particularly a human.

The term "treatment" designates curative, symptomatic, or preventative treatment. The compounds of this invention can thus be used upon subjects (such as mammals, in particular humans) having a declared disease. The compounds of this invention can also be used to delay or slow down the progress or prevent the further progress of the disease, thus improving the subjects' condition. The compounds of this invention can finally be administered to healthy subjects that might normally develop the disease or have a significant risk of developing the disease.

Pharmaceutical compositions according to the invention advantageously comprise one or several excipients or vehicles, acceptable within a pharmaceutical context (e.g. saline solutions, physiological solutions, isotonic solutions, etc., compatible with pharmaceutical usage and well-known by one of ordinary skill in the art). The compositions can comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc. The compositions can be formulated in the form of injectable suspensions, gels, oils, pills, suppositories, powders, gelcaps, capsules, aerosols, etc., eventually by means of galenic forms or devices assuring a prolonged and/or slow release. For this kind of formulation, agents such as cellulose, carbonates or starches can advantageously be used.

The compounds or compositions according to the invention can be administered in different ways and in different forms. Thus, for example, they can be administered in a systematic way, per os, parenterally, by inhalation, or by injection, such as for example intravenously, by intramuscular route, by subcutaneous route, by transdermal route, by intra-arterial route, etc. For the injections, the compounds are generally conditioned in the form of liquid suspensions which can be injected using syringes or perfusions, for example.

It is understood that the speed and/or the dose relative to the injection can be adapted by one of ordinary skill in the art, in function of the patient, the pathology, the form of administration, etc. Typically, the compounds are administered at doses varying between 1 µg and 2 g per administration, preferentially from 0.1 mg to 1 g per administration. Administra-

DESCRIPTION OF THE FIGURES

Figure 3:
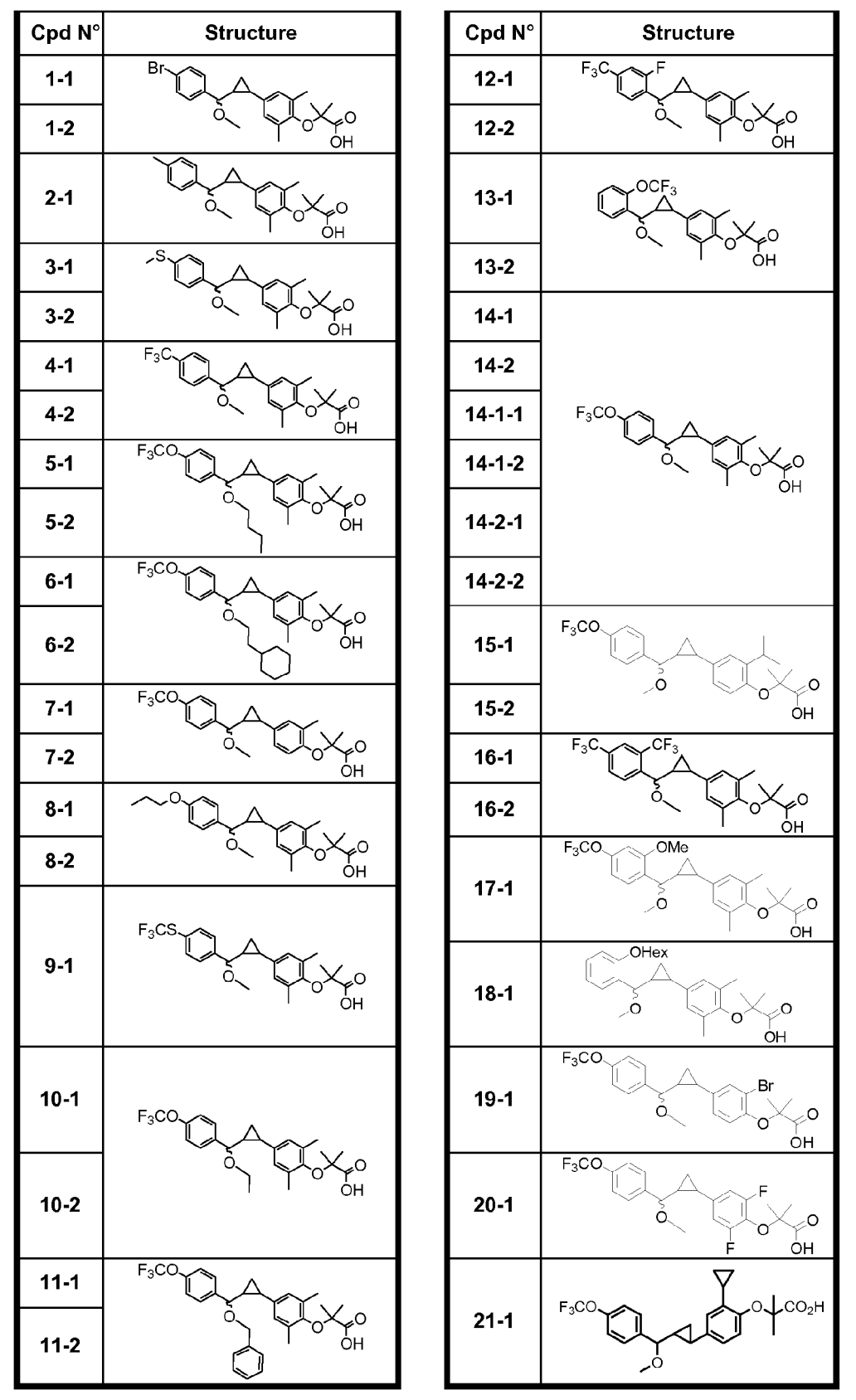

FIG. 3—Specific compounds of General Formula (I) according to the invention.

ABBREVIATION USED IN THESE FIGURES

Figure 1A:
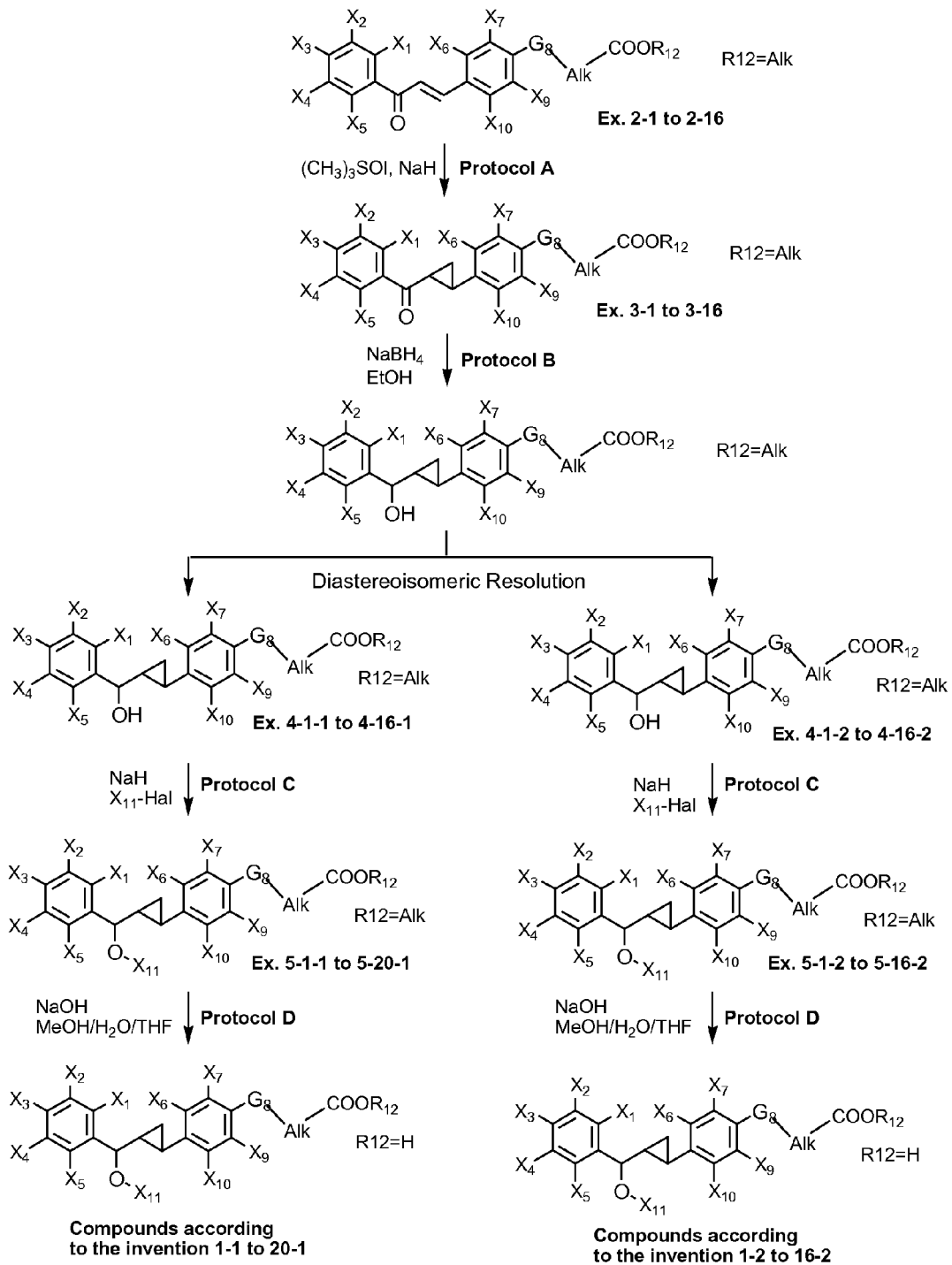
FIGS. 1a & 1b—General synthetic scheme of the Compounds of Formula (I) as racemate mixtures Alk means an alkyl group as defined above. The compounds of General Formula (I) described in Example 5, are generated from starting diphenylpropenone esters in 4 reaction steps and one (FIG. 1a) or two (FIG. 1a and FIG. 2) stereoisomeric resolution steps. As depicted in FIG. 1a, the diphenylpropenones quoted in Example 2 are used to prepare intermediate ((benzoyl(cyclopropyl))phenyl derivatives from Example 3 according to Protocol A in a highly diastereoselective to diastereospecific reaction step. Intermediates from Example 3 are then used to prepare intermediate alcohols from Example 4 as a mixture of the diastereoisomeric forms. At this step a diastereoisomeric resolution, as for example a chromatography on silica gel (normal phase, 40-60 µM), are used to separate both enantiomeric pairs Ex. 4-1-1 to 4-14-1 and 4-2-1 to 4-14-2. Those enantiomeric pairs are used separately to prepare racemate alkoxy(phenyl)methyl)cyclopropyl)phenyles from Example 5 using Protocol C. Finally, using Protocol D, the compounds according to the invention from Example 6 are generated from the compounds described in Example 5. Further substitutions can be introduced as illustrated by the synthesis of example 5-21-1 starting from example 5-19-1 and using Protocol F (FIG. 1b).

Cpd: Compound
DMSO: Dimethyl Sulfoxide
de: diastereoisomeric excess
Ex: Example
Eq: Equivalent
ee: enantiomeric excess
ESI-MS ElectroSpray Ionization-Mass Spectroscopy
Fig.: Figure
IPA Isopropyl Alcohol
HPLC: High Performance Liquid Chromatography
MHz: Mega Hertz
NMR Nuclear Magnetic Resonance
ppm part per million
Rf: Retention factor
Rt: Retention time
RT: Room Temperature
TFA Trifluoroacetic acid
TLC Thin Layer Chromatography
V: volume Statistic Analyses The statistical studies consist of a Student's t-test (*//*) and/or a univariate ANOVA analysis of variance, followed by Tukey test (°/°°/°°°). The results are compared to a control group according to the value of parameter p: °/*: $p<0.05$; °°/: $p<0.01$; °°°/*: $p<0.001$.

EXAMPLES

Classical reagents and catalysts are commercially available (Aldrich, Alfa Aesar, Acros, Fluka or Lancaster as suppliers).

Nuclear Magnetic Resonance spectra of proton (NMR $^1$H) were measured on a Bruker AC300P spectrometer at 250, 300 or 400 MHz in the appropriate deuterated solvent. Chemical shifts (δ) were expressed in ppm (parts per million) and the splitting of the NMR signals were described by with the usual abbreviations.

Example 1

General Protocols

Compounds provided herein may generally be prepared using standard synthetic methods. Starting materials are generally readily available from commercial sources, such as Interchim, Sigma-Aldrich or Carlo-Erba, or may be prepared as described herein, or using standard synthetic methods known by the person skilled in the art.

The compounds of the invention are prepared according to the general methods and general protocols of synthesis given below. Representative procedures suitable for the preparation of compounds of General Formula (I) are outlined in the Reaction Schemes for intermediate and final (FIGS. 1a & 1b and 2) compounds. Reagents and conditions may be adapted and additional steps employed to produce further compounds encompassed in the present invention having alternative substituent groups, or for achieving such compounds at higher yield and/or of higher purity. The final and intermediate compounds were characterized structurally by proton Nuclear Magnetic Resonance ($^1$H NMR). Mass analyses were performed on a Q-TOF (Quadripol-Time of Flight) by ESI-MS (Electrospray Ionisation-Mass Spectroscopy). The purity of the final and intermediate compounds was measured by High Performance Liquid Chromatography (HPLC) and/or by Thin Layer Chromatography (TLC).

Protocol A:

In a three-necked round-bottom flask, under a nitrogen atmosphere, the diphenylpropenone (1 eq.) is solved in dimethyl sulfoxide (0.2 mol/L), cooled to 0° C., and a mix of trimethyloxosulfonium iodide and NaH (1.2 eq.) is added by portions. The reaction mixture is stirred at 60° C. during 3 hours. After cooling to room temperature, the reaction mixture is diluted with water, extracted with a solvent such as ethyl acetate or diethyl ether. The combined organic layers are washed with brine, dried over magnesium sulfate, filtered and concentrated under reduced pressure. The residue is purified by chromatography on silica gel column; eluent: petroleum ether/ethyl acetate: 95/5.

Protocol B:

To an ice cooled solution of ketone (1 eq.) in methanol (0.15 mol·L$^{-1}$) is added sodium borohydride (3 eq.). The reaction mixture is stirred for 1 hour at room temperature and then dilute citric acid (1N) is added to pH=5. The methanol is removed by evaporation under reduced pressure and the residue is diluted with a solvent such as dichloromethane or ethyl acetate and washed with a saturated solution of ammonium chloride. The organic layer is washed with water, dried over magnesium sulfate and concentrated under vacuum. The residue is purified by chromatography on silica gel to afford the separate diastereoisomers; one to several purifications in a row may be performed to obtain high diastereoisomeric excess, ranging for example from 80% to 100%; eluent: petroleum ether/ethyl acetate: 95/5, unless otherwise indicated.

Protocol C:

An ice-cooled (−10° C.) solution of alcohol (1 eq.) in anhydrous N,N-dimethylformamide (0.1-0.2 mol/L) is treated with sodium hydride (1.6 eq.) After 10 min. of stirring, the appropriate halogenoalkyle (1.2 eq.) is added and stirring is pursued at room temperature for 2 to 15 hours. The reaction mixture is diluted with a saturated solution of ammonium chloride and extracted with ethyl acetate. The combined organic layers are washed with brine, dried over magnesium sulfate and concentrated under vacuum. The residue is purified by chromatography on silica gel; Eluent: petroleum ether/ethyl acetate: 95/5, unless otherwise indicated.

Protocol D:

The esters (1 eq.) are solved in a mixture of methanol/water: 2 v/1 v (0.1-1 mol/L) and solid sodium hydroxide is added (20 eq.). The reaction mixture is stirred for 2 hours at room temperature before tetrahydrofuran (2 v) is added. After an additional 18 hours of stirring, the reaction mixture is acidified with a solution of citric acid (2N) or with a solution of hydrochloric acid (1N) (until pH 2-3) and extracted with dichloromethane. The combined organic layers are washed with water, brine and dried over magnesium sulfate. After solvent removal under vacuum, the residue is purified by chromatography on silica gel column; eluent: dichloromethane/methanol: 98/2 to 95/5 unless otherwise indicated.

Protocol E

Racemic mixtures are purified by preparative HPLC chiral chromatography using a Chiralpak AD-H column, 250×20 mm; eluent: Heptane/isopropyl alcohol (IPA), trifluoroacetic acid (TFA): 96/4, 0.1%, isocratic method.

Protocol F

Intermediate aryl bromide (1 eq.), tricyclohexylphosphine (0.2 eq.), cyclopropylboronic acid (3 eq.) and potassium phosphate (4 eq.) are placed under a nitrogen atmosphere in a mixture of toluene/water: 91 v/9 v (0.03 mol/L). Palladium acetate (0.1-1 eq.) is added and the reaction mixture is stirred at 100° C. during 3 hours. The reaction mixture is diluted with ethyl acetate, filtered and washed with water. The organic layer is dried over magnesium sulfate. After solvent removal under vacuum, the residue is used without further purification or if necessary, purified by chromatography on silica gel column; eluent: petroleum ether/ethyl acetate: 95/5 to 9/1.

Example 2

Synthesis of Intermediate Diphenylpropenones

Starting diphenylpropenone esters (Table 2-1) were prepared according to the methods described in WO2004005233.

TABLE 2-1

| Starting diphenylpropenones | 1H NMR (MHz, solvent) data |
|---|---|
| Ex. 2-1: Ethyl 2-(4-(3-(4-bromophenyl)-3-oxoprop-1-enyl)-2,6-dimethylphenoxy)-2-methylpropanoate | (250 MHz, CDCl$_3$) 1.37 (t, 3H, J = 7.1 Hz); 1.50 (s, 6H); 2.25 (s, 6H); 4.30 (q, 2H, J = 7.1 Hz); 7.28 (s, 2H); 7.36 (d, 1H, J = 15.7 Hz); 7.64 (d, 2H, J = 8.1 Hz); 7.72 (d, 1H, J = 15.7 Hz); 7.88 (d, 2H, J = 8.1 Hz) |
| Ex. 2-2: Ethyl 2-(4-(3-(4-methylphenyl)-3-oxoprop-1-enyl)-2,6-dimethylphenoxy)-2-methylpropanooate | (250 MHz, CDCl$_3$) 1.39 (t, 3H, J = 7.1 Hz); 1.56 (s, 6H); 2.28 (s, 6H); 2.46 (s, 3H); 4.33 (q, 2H, J = 7.1 Hz); 7.31-7.34 (m, 4H); 7.45 (d, 1H, J = 15.7 Hz); 7.73 (d, 1H, J = 15.7 Hz); 7.96 (d, 2H, J = 8.1 Hz) |
| Ex. 2-3: Ethyl 2-(4-(3-(4-methylthiophenyl)-3-oxoprop-1-enyl)-2,6-dimethylphenoxy)-2-methylpropanoate | (250 MHz, CDCl$_3$) 1.37 (t, 3H, J = 7.1 Hz); 1.50 (s, 6H); 2.25 (s, 6H); 2.54 (s, 3H); 4.30 (q, 2H, J = 7.1 Hz); 7.22-7.37 (m, 4H); 7.41 (d, 1H, J = 15.7 Hz); 7.71 (d, 1H, J = 15.7 Hz); 7.96 (d, 2H, J = 8.1 Hz) |
| Ex. 2-4: Ethyl 2-(4-(3-(4-(trifluoromethyl)phenyl)-3-oxoprop-1-enyl)-2,6-dimethylphenoxy)-2-methylpropanoate | (250 MHz, CDCl$_3$) 1.37 (t, 3H, J = 7.1 Hz); 1.50 (s, 6H); 2.25 (s, 6H); 4.31 (q, 2H, J = 7.1 Hz); 7.30 (s, 2H); 7.37 (d, 1H, J = 15.7 Hz); 7.72 (d, 1H, J = 15.7 Hz); 7.76 (d, 2H, J = 8.1 Hz); 8.09 (d, 2H, J = 8.1 Hz) |
| Ex. 2-5: Ethyl 2-(4-(3-(4-(trifluoromethoxy)phenyl)-3-oxoprop-1-enyl)-2,6-dimethylphenoxy)-2-methylpropanoate | (300 MHz, CDCl$_3$) 1.37 (t, 3H, J = 7.1 Hz); 1.51 (s, 6H); 2.26 (s, 6H); 4.31 (q, 2H, J = 7.1 Hz); 7.30 (s, 2H); 7.32 (d, 2H, J = 8.2 Hz); 7.39 (d, 1H, J = 15.4 Hz); 7.73 (d, 1H, J = 15.4 Hz); 8.07 (d, 2H, J = 8.2 Hz) |
| Ex. 2-6: Ethyl 2-(4-(3-(4-(trifluoromethoxy)phenyl)-3-oxoprop-1-enyl)-2-methylphenoxy)-2-methylpropanoate | (250 MHz, CDCl$_3$) 1.24 (t, 3H, J = 7.1 Hz); 1.65 (s, 6H); 2.28 (s, 3H); 4.25 (q, 2H, J = 7.1 Hz); 6.64 (d, 1H, J = 8.5 Hz); 7.27-7.38 (m, 4H); 7.47 (s, 1H); 7.75 (d, 1H, J = 15.7 Hz); 8.06 (d, 2H, J = 8.1 Hz) |
| Ex. 2-7: Ethyl 2-(4-(3-(4-(propyloxy)phenyl)-3-oxoprop-1-enyl)-2,6-dimethylphenoxy)-2-methylpropanoate | (250 MHz, CDCl$_3$) 1.06 (t, 3H, J = 7.4 Hz); 1.37 (t, 3H, J = 7.1 Hz); 1.50 (s, 6H); 1.70-1.82 (m, 2H); 2.25 (s, 6H); 4.01 (t, 2H, J = 7.4 Hz); 4.30 (q, 2H, J = 7.1 Hz); 6.97 (d, 2H, J = 8.9 Hz); 7.28 (s, 2H); 7.44 (d, 1H, J = 15.6 Hz); 7.70 (d, 1H, J = 15.6 Hz); 8.03 (d, 2H, J = 8.9 Hz) |

TABLE 2-1-continued

| Starting diphenylpropenones | 1H NMR (MHz, solvent) data |
|---|---|
| Ex. 2-8: Ethyl 2-(4-(3-(4-(trifluoromethylthio)phenyl)-3-oxoprop-1-enyl)-2,6-dimethylphenoxy)-2-methylpropanoate | (250 MHz, CDCl$_3$) 1.39 (t, 3H, J = 7.1 Hz); 1.56 (s, 6H); 2.28 (s, 6H); 4.33 (q, 2H, J = 7.1 Hz); 7.32 (s, 2H); 7.40 (d, 1H, J = 15.5 Hz); 7.75 (d, 1H, J = 15.5 Hz); 7.80 (d, 2H, J = 8.1 Hz); 8.05 (d, 2H, J = 8.1 Hz) |
| Ex. 2-9: Ethyl 2-(4-(3-(2-fluoro-4-(trifluoromethoxy)phenyl)-3-oxoprop-1-enyl)-2,6-dimethylphenoxy)-2-methylpropanoate | (250 MHz, CDCl$_3$) 1.36 (t, 3H, J = 7.2 Hz); 1.50 (s, 6H); 2.24 (s, 6H); 4.30 (q, 2H, J = 7.1 Hz); 7.21 (dd, 1H, J = 15.7 Hz); 7.26 (s, 2H); 7.45 (d, 1H, J = 10.1 Hz); 7.53 (d, 1H, J = 8.1 Hz); 7.61 (dd, 1H, J = 15.8 Hz); 7.87 (t, 1H, J = 7.2 Hz) |
| Ex. 2-10: Ethyl 2-(4-(3-(2-(trifluoromethoxy)phenyl)-3-oxoprop-1-enyl)-2,6-dimethylphenoxy)-2-methylpropanoate | (250 MHz, CDCl$_3$) 1.38 (t, 3H, J = 7.1 Hz); 1.49 (s, 6H); 2.22 (s, 6H); 4.30 (q, 2H, J = 7.1 Hz); 7.08 (d, 1H; J = 16.0 Hz); 7.22 (s, 2H); 7.33-7.43 (m, 2H); 7.45 (d, 1H, J = 15.7 Hz); 7.55 (td, 1H, J = 8.1 Hz, 1.9 Hz); 8.09 (dd, 1H, J = 8.1 Hz, 1.9 Hz) |
| Ex. 2-11: Ethyl 2-(2-isopropyl-4-(3-oxo-3-(4-(trifluoromethoxy)phenyl)prop-1-enyl)phenoxy)-2-methylpropanoate | (300 MHz, CDCl$_3$): 1.20-1.28 (m, 9H); 1.67 (s, 6H); 3.36 (m, 1H); 4.22 (q, 2H, J = 7.0 Hz); 6.62 (d, 1H, J = 8.7 Hz); 7.32-7.38 (m, 4H); 7.50 (d, 1H, J = 2.3 Hz); 7.75 (d, 1H, J = 15.7 Hz); 8.05 (m, 2H) |
| Ex. 2-12: Ethyl 2-(4-(3-(2,4-bis(trifluoromethyl)phenyl)-3-oxoprop-1-enyl)-2,6-dimethylphenoxy)-2-methylpropanoate | (300 MHz, CDCl$_3$): 1.36 (t, 3H, J = 7.0 Hz); 1.49 (s, 6H); 2.22 (s, 6H); 4.30 (q, 2H, J = 7.0 Hz); 6.93 (d, 1H, J = 16.3 Hz); 7.15 (d, 1H, J = 16.3 Hz); 7.19 (s, 2H); 7.58 (d, 1H, J = 8.4 Hz); 7.90 (d, 1H, J = 8.4 Hz); 8.02 (s, 1H) |
| Ex. 2-13: Ethyl 2-(4-(3-(2-methoxy-4-(trifluoromethoxy)phenyl)-3-oxoprop-1-enyl)-2,6-dimethylphenoxy)-2-methylpropanoate | (300 MHz, CDCl$_3$): 1.36 (t, 3H, J = 7.0 Hz); 1.50 (s, 6H); 2.24 (s, 6H); 3.92 (s, 3H); 4.30 (q, 2H, J = 7.0 Hz); 6.82 (d, 1H); 6.90 (d, 1H, J = 8.5 Hz); 7.20 (d, 1H, J = 15.7 Hz); 7.23 (s, 2H); 7.50 (d, 1H, J = 15.7 Hz); 7.62 (d, 1H, J = 8.5 Hz) |
| Ex. 2-14: Ehyl 2-(4-(3-(2-(hexyloxy)phenyl)-3-oxoprop-1-enyl)-2,6-dimethylphenoxy)-2-methylpropanoate | (250 MHz, CDCl$_3$): 0.79 (t, 3H, J = 7.0 Hz); 1.14-1.26 (m, 4H); 1.36 (t, 3H, J = 7.0 Hz); 1.39-1.46 (m, 2H); 1.48 (s, 6H); 1.72-1.83 (m, 2H); 2.22 (s, 6H); 4.04 (t, 2H, J = 6.3 Hz); 4.29 (q, 2H, J = 7.0 Hz); 6.94-7.03 (m, 2H); 7.21 (s, 2H); 7.34 (d, 1H, J = 15.8 Hz); 7.38-7.49 (m, 1H); 7.51 (d, 1H, J = 15.8 Hz); 7.62 (dd, 1H, J = 7.6 Hz, J = 1.8 Hz) |
| Ex. 2-15: Ethyl 2-(2-bromo-4-(3-oxo-3-(4-(trifluoromethoxy)phenyl)prop-1-enyl)phenoxy)-2-methylpropanoate | (250 MHz, CDCl$_3$): 1.26 (t, 3H, J = 7.2 Hz); 1.68 (s, 6H); 4.25 (q, 2H, J = 7.2 Hz); 6.81 (d, 1H, J = 8.6 Hz); 7.33 (d, 2H, J = 8.5 Hz); 7.50 (d, 1H, J = 15.7 Hz); 7.43 (dd, 1H, J = 8.6 Hz, J = 2.2 Hz); 7.70 (d, 1H, J = 15.7 Hz); 7.88 (d, 1H, J = 2.2 Hz); 8.06 (d, 2H, J = 8.5 Hz) |
| Ex. 2-16: Ethyl 2-(2,6-difluoro-4-(3-oxo-3-(4-(trifluoromethoxy)phenyl)prop-1-enyl)phenoxy)-2-methylpropanoate | (250 MHz, CDCl$_3$): 1.32 (t, 3H, J = 7.2 Hz); 1.6 (s, 6H); 4.27 (q, 2H, J = 7.2 Hz); 7.13-7.24 (m, 2H); 7.3-7.42 (m, 3H); 7.65 (d, 1H, J = 15.7 Hz); 8.06 (d, 2H, J = 8.5 Hz) |

Example 3

Synthesis of Intermediate Benzoylcyclopropyle Derivatives According to the Invention The synthesis of those intermediate compounds depicted in FIG. 1a and summarized in Table 3-1 was realized using the Protocol A described in Example 1.

TABLE 3-1

Systematic name

| Ex. | Starting materials, Protocol, yield. | $^1$H NMR (MHz, solvent) data |
|---|---|---|
| Ex. 3-1 | Ethyl 2-(4-(2-(4-bromobenzoyl)cyclopropyl)-2,6-dimethylphenoxy)-2-methylpropanoate<br>Ex. 2-1, Protocol A,<br>Yield: 93%. | (250 MHz, CDCl$_3$): 1.35 (t, 3H, J = 7.1 Hz); 1.46 (s, 6H); 1.50-1.56 (m, 1H); 1.83-1.90 (m, 1H); 2.18 (s, 6H); |

TABLE 3-1-continued

| Ex. | Starting materials, Protocol, yield. | $^1$H NMR (MHz, solvent) data |
|---|---|---|
| | | 2.55-2.63 (m, 1H); 2.74-2.81 (m, 1H); 4.29 (q, 2H, J = 7.1 Hz); 6.75 (s, 2H); 7.60 (d, 2H, J = 8.6 Hz); 7.86 (d, 2H, J = 8.6 Hz). |
| Ex. 3-2 | Ethyl 2-(4-(2-(4-methylbenzoyl)cyclopropyl)-2,6-dimethylphenoxy)-2-methylpropanoate | |
| | Ex. 2-2, Protocol A, Yield: 96%. | (250 MHz, CDCl$_3$): 1.34 (t, 3H, J = 7.1 Hz); 1.48 (s, 6H); 1.46-1.52 (m, 1H); 1.83-1.90 (m, 1H); 2.21 (s, 6H); 2.44 (s, 3H); 2.55-2.64 (m, 1H); 2.83-2.87 (m, 1H); 4.32 (q, 2H, J = 7.1 Hz); 6.78 (s, 2H); 7.28 (d, 2H, J = 8.3 Hz); 7.93 (d, 2H, J = 8.3 Hz). |
| Ex. 3-3 | Ethyl 2-(4-(2-(4-(methylthio)benzoyl)cyclopropyl)-2,6-dimethylphenoxy)-2-methylpropanoate | |
| | Ex. 2-3, Protocol A, Yield: 96%. | (250 MHz, CDCl$_3$): 1.34 (t, 3H, J = 7.1 Hz); 1.46 (s, 6H); 1.44-1.50 (m, 1H); 1.82-1.86 (m, 1H); 2.18 (s, 6H); 2.52 (s, 3H); 2.53-2.62 (m, 1H); 2.73-2.82 (m, 1H); 4.29 (q, 2H, J = 7.1 Hz); 6.75 (s, 2H); 7.28 (d, 2H, J = 8.6 Hz); 7.92 (d, 2H, J = 8.6 Hz). |
| Ex. 3-4 | Ethyl 2-(4-(2-(4-(trifluoromethyl)benzoyl)cyclopropyl)-2,6-dimethylphenoxy)-2-methylpropanoate | |
| | Ex. 2-4, Protocol A, Yield: 92%. | (250 MHz, CDCl$_3$): 1.36 (t, 3H, J = 7.1 Hz); 1.47 (s, 6H); 1.50-1.56 (m, 1H); 1.86-1.94 (m, 1H); 2.19 (s, 6H); 2.59-2.67 (m, 1H); 2.78-2.85 (m, 1H); 4.29 (q, 2H, J = 7.1 Hz); 6.76 (s, 2H); 7.73 (d, 2H, J = 8.2 Hz); 8.09 (d, 2H, J = 8.2 Hz). |
| Ex. 3-5 | Ethyl 2-(4-(2-(4-(trifluoromethoxy)benzoyl)cyclopropyl)-2,6-dimethylphenoxy)-2-methylpropanoate | |
| | Ex. 2-5, Protocol A, Yield: 94%. | (300 MHz, CDCl$_3$): 1.36 (t, 3H, J = 7.0 Hz); 1.47 (s, 6H); 1.49-1.57 (m, 1H); 1.84-1.91 (m, 1H); 2.16 (s, 6H); 2.57-2.64 (m, 1H); 2.76-2.82 (m, 1H); 4.30 (q, 2H, J = 7.0 Hz); 6.76 (s, 2H); 7.29-7.33 (m, 2H); 8.03-8.07 (m, 2H). |
| Ex. 3-6 | Ethyl 2-(4-(2-(4-trifluoromethoxy)benzoyl)cyclopropyl)-2-methylphenoxy)-2-methylpropanoate | |
| | Ex. 2-6, Protocol A, Yield: 88%. | (250 MHz, CDCl$_3$): 1.35 (t, 3H, J = 7.1 Hz); 1.61 (s, 6H); 1.44-1.50 (m, 1H); 1.86-1.94 (m, 1H); 2.18 (s, 3H); 2.61-2.69 (m, 1H); 2.76-2.83 (m, 1H); 4.28 (q, 2H, J = 7.1 Hz); 6.61-6.65 (m, 1H); 6.87 (d, 1H, J = 8.4 Hz); 6.96 (s, 1H); 7.31 (d, 2H, J = 8.6 Hz); 8.04 (d, 2H, J = 8.6 Hz). |
| Ex. 3-7 | Ethyl 2-(4-(2-(4-(propyloxy)benzoyl)cyclopropyl)-2,6-dimethylphenoxy)-2-methylpropanoate | |
| | Ex. 2-7, Protocol A, Yield: 99%. | (250 MHz, CDCl$_3$): 1.04 (t, 3H, J = 7.4 Hz); 1.35 (t, 3H, J = 7.1 Hz); 1.46 (s, 6H); 1.44-1.50 (m, 1H); 1.75-1.89 (m, 3H); 2.18 (s, 6H); 2.51-2.59 (m, 1H); 2.76-2.83 (m, 1H); 3.96 (t, 2H, J = 7.1 Hz); 4.28 (q, 2H, J = 7.1 Hz); 6.76 (s, 2H); 6.92 (d, 2H, J = 8.7 Hz); 7.98 (d, 2H, J = 8.7 Hz). |
| Ex. 3-8 | Ethyl 2-(4-(2-(4-trifluoromethylthio)benzoyl)cyclopropyl)-2,6-dimethylphenoxy)-2-methylpropanoate | |
| | Ex. 2-8, Protocol A, Yield: 80%. | (250 MHz, CDCl$_3$): 1.35 (t, 3H, J = 7.1 Hz); 1.47 (s, 6H); 1.50-1.57 (m, 1H); 1.84-1.91 (m, 1H); 2.19 (s, 6H); 2.59-2.65 (m, 1H); 2.79-2.83 (m, 1H); 4.29 (q, 2H, J = 7.1 Hz); 6.77 (s, 2H); 7.72 (d, 2H, J = 8.3 Hz); 8.01 (d, 2H, J = 8.3 Hz). |

TABLE 3-1-continued

| Ex. | Starting materials, Protocol, yield. | $^1$H NMR (MHz, solvent) data |
|---|---|---|
| Ex. 3-9 | Ethyl 2-(4-(2-(2-fluoro-4-trifluoromethylbenzoyl)cyclopropyl)-2,6-dimethylphenoxy)-2-methylpropanoate | |
| | Ex. 2-9, Protocol A, Yield: 77%. | (250 MHz, CDCl$_3$): 1.35 (t, 3H, J = 7.1 Hz); 1.46 (s, 6H); 1.51-1.60 (m, 1H); 1.88-1.95 (m, 1H); 2.19 (s, 6H); 2.65-2.73 (m, 1H); 2.78-2.86 (m, 1H); 4.28 (q, 2H, J = 7.1 Hz); 6.76 (s, 2H); 7.38-7.46 (m, 1H); 7.41-7.47 (m, 1H); 7.68-7.74 (m, 1H). |
| Ex. 3-10 | Ethyl 2-(4-(2-(2-trifluoromethoxybenzoyl)cyclopropyl)-2,6-dimethylphenoxy)-2-methylpropanoate | |
| | Ex. 2-10, Protocol A, Yield: 80%. | (250 MHz, CDCl$_3$): 1.36 (t, 3H, J = 7.1 Hz); 1.45 (s, 6H); 1.50-1.56 (m, 1H); 1.84-1.91 (m, 1H); 2.17 (s, 6H); 2.66-2.75 (m, 2H); 4.28 (q, 2H, J = 7.1 Hz); 6.73 (s, 2H); 7.27-7.33 (m, 1H); 7.35-7.41 (m 1H); 7.49-7.55 (m, 1H); 7.61-7.66 (m, 1H). |
| Ex. 3-11 | Ethyl 2-(2-isopropyl-4-(2-(4-(trifluoromethoxy)benzoyl)cyclopropyl)phenoxy)-2-methylpropanoate | |
| | Ex. 2-11, Protocol A, Yield: 95%. | (250 MHz, CDCl$_3$): 1.18-1.27 (m, 9H); 1.50-1.57 (m, 1H); 1.60 (s, 6H); 1.85-1.92 (m, 1H); 2.61-2.69 (m, 1H); 2.74-2.81 (m, 1H); 3.36 (hept, 1H, J = 6.7 Hz); 4.24 (q, 2H, J = 7.0 Hz); 6.6 (d, 1H, J = 8.2 Hz); 6.81 (dd, 1H, J = 8.5 Hz, 2.5 Hz); 7.03 (d, 1H, J = 2.5 Hz); 7.28 (d, 2H, J = 8.5 Hz); 8.04 (d, 2H, J = 8.5 Hz) |
| Ex. 3-12 | Ethyl 2-(4-(2-(2,4-bis(trifluoromethyl)benzoyl)cyclopropyl)-2,6-dimethylphenoxy)-2-methylpropanoate | |
| | Ex. 2-12, Protocol A, Yield: 88%. | (250 MHz, CDCl$_3$): 1.34 (t, 3H, J = 7.2 Hz); 1.45 (s, 6H); 1.59-1.68 (m, 1H); 1.93-2.01 (m, 1H); 2.16 (s, 6H); 2.43-2.50 (m, 1H); 2.69-2.78 (m, 1H); 4.28 (q, 2H, J = 7.2 Hz); 6.72 (s, 2H); 7.66 (d, 1H, J = 8.2 Hz); 7.88 (d, 1H, J = 8.2 Hz); 7.96 (br s, 1H) |
| Ex. 3-13 | Ethyl 2-(4-(2-(2-methoxy-4-(trifluoromethoxy)benzoyl)cyclopropyl)-2,6-dimethylphenoxy)-2-methylpropanoate | |
| | Ex. 2-13, Protocol A, Yield: 95%. | (250 MHz, CDCl$_3$): 1.39 (t, 3H, J = 7.1 Hz); 1.42-1.51 (m, 7H); 1.91-1.96 (m, 1H); 2.21 (s, 6H); 2.48-2.58 (m, 1H); 2.82-2.91 (m, 1H); 3.73 (s, 3H); 4.32 (q, 2H, J = 7.1 Hz); 6.74-6.81 (m, 3H); 6.83-6.95 (m, 1H); 7.68 (d, 1H, J = 8.5 Hz) |
| Ex. 3-14 | Ethyl 2-(4-(2-(2-(hexyloxy)benzoyl)cyclopropyl)-2,6-dimethylphenoxy)-2-methylpropanoate | |
| | Ex. 2-14, Protocol A, Yield: 91%. | (250 MHz, CDCl$_3$): 0.88 (t, 3H, J = 7.0 Hz); 1.17-1.29 (m, 4H); 1.3-1.42 (m, 5H); 1.45 (s, 6H); 1.52-1.63 (m, 3H); 1.78-1.85 (m, 1H); 2.16 (s, 6H); 2.54-2.63 (m, 1H); 3.01-3.1 (m, 1H); 3.96 (t, 2H, J = 6.5 Hz); 4.28 (q, 2H, J = 7.2 Hz); 6.72 (s, 2H); 6.9-6.99 (m, 2H); 7.37-7.44 (m, 1H); 7.59 (dd, 1H, J = 7.6 Hz, J = 1.8 Hz) |
| Ex. 3-15 | Ethyl 2-(2-bromo-4-(2-(4-(trifluoromethoxy)benzoyl)cyclopropyl)phenoxy)-2-methylpropanoate | |
| | Ex. 2-15, Protocol A, Yield: 95%. | (250 MHz, CDCl$_3$): 1.29 (t, 3H, J = 7.2 Hz); 1.47-1.55 (m, 1H); 1.62 (s, 6H); 1.85-1.92 (m, 1H); 2.59-2.67 (m, 1H); 2.74-2.82 (m, 1H); 4.26 (q, 2H, J = 7.2 Hz); 6.8 (d, 1H, J = 8.5 Hz); 6.99 (dd, 1H, J = 8.5 Hz, J = 2.5 Hz); 7.27-7.34 (m, 3H); 8.03 (d, 2H, J = 8.5 Hz) |
| Ex. 3-16 | Ethyl 2-(2,6-difluoro-4-(2-(4-(trifluoromethoxy)benzoyl)cyclopropyl)phenoxy)-2-methylpropanoate | |
| | Ex. 2-16, Protocol A, Yield: 83%. | (250 MHz, CDCl$_3$): 1.32 (t, 3H, J = 7.1 Hz); 1.45-1.54 (m, 1H); 1.55 (s, 6H); 1.86-1.93 (m, 1H); 2.59-2.67 (m, 1H); 2.76-2.86 (m, 1H); 4.25 (q, 2H, J = 7.1 Hz); 6.64-6.75 (m, 2H); 7.29-7.33 (m, 2H); 8.02-8.06 (m, 2H) |

Example 4

Synthesis of Intermediate Alcohols According to the Invention

The synthesis of the enantiomeric pairs as depicted in FIG. 1a and summarized in Table 4-1 was realized using the Protocol B described in Example 1. As an example of the preparation of pure enantiomers (FIG. 2), Ex. 4-5-1 and 4-5-2 were purified according to Protocol E to generate the pure enantiomers, Ex. 4-5-1-1 and Ex. 4-5-1-2, and, Ex. 4-5-2-1 and Ex. 4-5-2-2 respectively.

TABLE 4-1

| Ex. | Systematic name<br>Starting materials, Protocol, purification, yield. | $^1$H NMR (MHZ, solvent) data |
|---|---|---|
| Ex. 4-1-1 | Ethyl 2-(4-(2-((4-bromophenyl)(hydroxy)methyl)cyclopropyl)-2,6-dimethylphenoxy)-2-methylpropanoate<br>Ex. 3-1, Protocol B,<br>Yield: 43%. | (250 MHz, CDCl$_3$): 0.91-1.04 (m, 2H); 1.36 (t, 3H, J = 7.1 Hz); 1.41-1.46 (m, 1H); 1.44 (s, 6H); 1.92-1.98 (m, 1H); 2.15 (s, 6H); 4.20 (dd, 1H, J = 8.3 Hz, 3.1 Hz); 4.28 (q, 2H, J = 7.1 Hz); 6.66 (s, 2H); 7.32 (d, 2H, J = 8.5 Hz); 7.49 (d, 2H, J = 8.5 Hz)<br>Rf (petroleum ether/ethyl acetate, 8/2) = 0.47. |
| Ex. 4-1-2 | Ethyl 2-(4-(2-((4-bromophenyl)(hydroxy)methyl)cyclopropyl)-2,6-dimethylphenoxy)-2-methylpropanoate<br>Ex. 3-1, Protocol B,<br>Yield: 9%. | (250 MHz, CDCl$_3$): 0.83-0.99 (m, 1H); 1.07-1.12 (m, 1H); 1.30-1.36 (m, 1H); 1.33 (t, 3H, J = 7.1 Hz); 1.43 (s, 6H); 1.84-1.90 (m, 1H); 2.12 (s, 6H); 4.26 (q, 2H, J = 7.1 Hz); 4.31-4.35 (m, 1H); 6.58 (s, 2H); 7.31 (d, 2H, J = 8.5 Hz); 7.47 (d, 2H, J = 8.5 Hz)<br>Rf (petroleum ether/ethyl acetate, 8/2) = 0.37. |
| Ex. 4-2-1 | Ethyl 2-(4-(2-((4-methylphenyl)(hydroxy)methyl)cyclopropyl)-2,6-dimethylphenoxy)-2-methylpropanoate<br>Ex. 3-2, Protocol B,<br>Yield: 54%. | (400 MHz, CDCl$_3$): 0.86-1.04 (m, 2H); 1.39 (t, 3H, J = 7.1 Hz); 1.48 (s, 6H); 1.50-1.58 (m, 1H); 1.91-2.02 (m, 1H); 2.18 (s, 6H); 2.39 (s, 3H); 4.21 (dd, 1H, J = 7.7 Hz, J = 3.1 Hz); 4.31 (q, 2H, J = 7.1 Hz); 6.70 (s, 2H); 7.21 (d, 2H, J = 8.2 Hz); 7.36 (d, 2H, J = 8.2 Hz)<br>Rf (petroleum ether/ethyl acetate, 8/2) = 0.40. |
| Ex. 4-2-2 | Ethyl 2-(4-(2-((4-methylphenyl)(hydroxy)methyl)cyclopropyl)-2,6-dimethylphenoxy)-2-methylpropanoate<br>Ex. 3-2, Protocol B,<br>Yield: 29%. | (250 MHz, CDCl$_3$): 0.86-1.05 (m, 1H); 1.09-1.22 (m, 1H); 1.36 (t, 3H, J = 7.1 Hz); 1.46 (s, 6H); 1.50-1.58 (m, 1H); 1.84-1.90 (m, 1H); 2.15 (s, 6H); 2.37 (s, 3H); 4.30 (q, 2H, J = 7.1 Hz); 4.32-4.39 (m, 1H); 6.62 (s, 2H); 7.19 (d, 2H, J = 8.0 Hz); 7.35 (d, 2H, J = 8.0 Hz)<br>Rf (petroleum ether/ethyl acetate, 8/2) = 0.32. |
| Ex. 4-3-1 | Ethyl 2-(4-(2-((4-methylthiophenyl)(hydroxy)methyl)cyclopropyl)-2,6-dimethylphenoxy)-2-methylpropanoate<br>Ex. 3-3, Protocol B,<br>Yield: 36%. | (250 MHz, CDCl$_3$): 0.86-1.04 (m, 2H); 1.33 (t, 3H, J = 7.1 Hz); 1.45 (s, 6H); 1.45-1.52 (m, 1H); 1.91-2.02 (m, 1H); 2.15 (s, 6H); 2.49 (s, 3H); 4.20 (dd, 1H, J = 7.9 Hz, J = 3.3 Hz); 4.28 (q, 2H, J = 7.1 Hz); 6.67 (s, 2H); 7.25 (d, 2H, J = 8.2 Hz); 7.36 (d, 2H, J = 8.2 Hz).<br>Rf (petroleum ether/ethyl acetate, 7/3) = 0.42. |
| Ex. 4-3-2 | Ethyl 2-(4-(2-((4-methylthiophenyl)(hydroxy)methyl)cyclopropyl)-2,6-dimethylphenoxy)-2-methylpropanoate<br>Ex. 3-3, Protocol B,<br>Yield: 17%.. | (250 MHz, CDCl$_3$): 0.86-1.05 (m, 1H); 1.09-1.22 (m, 1H); 1.33 (t, 3H, J = 7.1 Hz); 1.43 (s, 6H); 1.42-1.48 (m, 1H); 1.83-1.88 (m, 1H); 2.12 (s, 6H); 2.48 (s, 3H); 4.27 (q, 2H, J = 7.1 Hz); |

TABLE 4-1-continued

| | | Systematic name | |
|---|---|---|---|
| Ex. | Starting materials, Protocol, purification, yield. | | ¹H NMR (MHZ, solvent) data |
| | | | 4.35 (dd, 1H, J = 7.2 Hz J = 3.4 Hz); 6.59 (s, 2H); 7.24 (d, 2H, J = 8.3 Hz); 7.36 (d, 2H, J = 8.3 Hz).<br>Rf (petroleum ether/ethyl acetate, 7/3) = 0.33. |
| Ex. 4-4-1 | Ethyl 2-(4-(2-((4-trifluoromethylphenyl)(hydroxy)methyl)cyclopropyl)-2,6-dimethylphenoxy)-2-methylpropanoate<br>Ex. 3-4, Protocol B,<br>Yield: 34%. | | (400 MHz, CDCl₃): 0.91-1.01 (m, 1H); 1.02-1.08 (m, 1H); 1.36 (t, 3H, J = 7.1 Hz); 1.42-1.48 (m, 1H); 1.46 (s, 6H); 1.93-2.02 (m, 1H); 2.07 (d, 1H, J = 3.5 Hz); 2.16 (s, 6H); 4.28-4.3 (m, 1H); 4.29 (q, 2H, J = 7.1 Hz); 6.67 (s, 2H); 7.57 (d, 2H, J = 8.2 Hz); 7.64 (d, 2H, J = 8.2 Hz)<br>Rf (petroleum ether/ethyl acetate, 8/2) = 0.37. |
| Ex. 4-4-2 | Ethyl 2-(4-(2-((4-trifluoromethylphenyl)(hydroxy)methyl)cyclopropyl)-2,6-dimethylphenoxy)-2-methylpropanoate<br>Ex. 3-4, Protocol B,<br>Yield: 14%. | | (250 MHz, CDCl₃): 0.80-0.93 (m, 1H); 1.04-1.10 (m, 1H); 1.30-1.36 (m, 1H); 1.33 (t, 3H, J = 7.1 Hz); 1.43 (s, 6H); 1.90-1.94 (m, 1H); 2.00 (d, 1H, J = 3.5 Hz); 2.12 (s, 6H); 4.26 (q, 2H, J = 7.1 Hz); 4.41-4.46 (m, 1H); 6.58 (s, 2H); 7.55 (d, 2H, J = 8.5 Hz); 7.61 (d, 2H, J = 8.5 Hz).<br>Rf (petroleum ether/ethyl acetate, 8/2) = 0.28. |
| Ex. 4-5-1 | Ethyl 2-(4-(2-((4-trifluoromethoxyphenyl)(hydroxy)methyl)cyclopropyl)-2,6-dimethylphenoxy)-2-methylpropanoate<br>Ex. 3.5, Protocol B,<br>Yield: 60%,<br>Eluent: cyclohexane/ethyl acetate: 9/1. | | (300 MHz, CDCl₃): 0.92-1.05 (m, 2H); 1.36 (t, 3H, J = 7.3 Hz); 1.46 (s, 6H); 1.41-1.51 (m, 1H); 1.93-2.01 (m, 1H); 2.01-2.07 (m, 1H); 2.16 (s, 6H); 4.22-4.28 (m, 1H); 4.28 (q, 2H, J = 7.3 Hz); 6.68 (s, 2H); 7.22 (d, 2H, J = 8.3 Hz); 7.47 (d, 2H, J = 8.3 Hz)<br>Rf (cyclohexane/ethyl acetate, 8/2) = 0.50. |
| Ex. 4-5-1-1 | Ethyl 2-(4-(2-((4-trifluoromethoxyphenyl)(hydroxy)methyl)cyclopropyl)-2,6-dimethylphenoxy)-2-methylpropanoate<br>Ex. 4-5.1, Protocol E,<br>Yield: 37%. | | (300 MHz, CDCl₃): 0.92-1.05 (m, 2H); 1.36 (t, 3H, J = 7.0 Hz); 1.46 (s, 6H); 1.46-1.51 (m, 1H); 1.94-2.01 (m, 1H); 2.16 (s, 6H); 4.22-4.28 (m, 1H); 4.28 (q, 2H, J = 7.3 Hz); 6.67 (s, 2H); 7.22 (d, 2H, J = 8.2 Hz); 7.47 (d, 2H, J = 8.2 Hz)<br>Rt (Chiralpak AD-H, 250 × 4.6 mm, IPA/nHeptane, TFA: 4/96, 0.1%) = 35.85 min. |
| Ex. 4-5-1-2 | Ethyl 2-(4-(2-((4-trifluoromethoxyphenyl)(hydroxy)methyl)cyclopropyl)-2,6-dimethylphenoxy)-2-methylpropanoate<br>Ex. 4-5.1 Protocol E,<br>Yield: = 35% | | (300 MHz, CDCl₃): 0.92-1.05 (m, 2H); 1.36 (t, 3H, J = 7.0 Hz); 1.46 (s, 6H); 1.46-1.51 (m, 1H); 1.94-2.01 (m, 1H, J = 4.4 Hz); 2.16 (s, 6H); 4.22-4.28 (m, 1H); 4.28 (q, 2H, J = 7.3 Hz); 6.67 (s, 2H); 7.22 (d, 2H, J = 8.2 Hz); 7.47 (d, 2H, J = 8.2 Hz)<br>Rt (Chiralpak AD-H, 250 × 4.6 mm, IPA/nHeptane, TFA: 4/96, 0.1%) = 28.86 min. |
| Ex. 4-5-2 | Ethyl 2-(4-(2-((4-trifluoromethoxyphenyl)(hydroxy)methyl)cyclopropyl)-2,6-dimethylphenoxy)-2-methylpropanoate<br>Ex. 3.5, Protocol B,<br>Yield: 34%,<br>Eluent: cyclohexane/ethyl acetate: 9/1. | | (300 MHz, CDCl₃): 0.94-1.01 (m, 1H); 1.08-1.16 (m, 1H); 1.33 (t, 3H, J = 7.3 Hz); 1.41-1.49 (m, 7H); 1.85-1.93 (m, 1H); 1.99 (d, 1H, J = 3.5 Hz); 2.13 (s, 6H); 4.26 (q, 2H, J = 7.3 Hz); 4.38 (dd, 1H, J = 7 Hz, 3.5 Hz); 6.58 (s, 2H); 7.2 (d, 2H, J = 8.3 Hz); 7.46 (d, 2H, J = 8.3 Hz)<br>Rf (cyclohexane/ethyl acetate, 8/2) = 0.45. |

TABLE 4-1-continued

| Ex. | Systematic name<br>Starting materials, Protocol, purification, yield. | $^1$H NMR (MHZ, solvent) data |
|---|---|---|
| Ex. 4-5-2-1 | Ethyl 2-(4-(2-((4-trifluoromethoxyphenyl)(hydroxy)methyl)cyclopropyl)-2,6-dimethylphenoxy)-2-methylpropanoate<br>Ex. 4-5-2, Protocol E, Yield: 31%. | (300 MHz, CDCl$_3$): 0.94-1.01 (m, 1H); 1.08-1.16 (m, 1H); 1.33 (t, 3H, J = 7.3 Hz); 1.41-1.49 (m, 7H); 1.85-1.93 (m, 1H); 1.99 (d, 1H, J = 3.5 Hz); 2.13 (s, 6H); 4.26 (q, 2H, J = 7.3 Hz); 4.38 (dd, 1H, J = 7 Hz, 3.5 Hz); 6.58 (s, 2H); 7.2 (d, 2H, J = 8.3 Hz); 7.46 (d, 2H, J = 8.3 Hz)<br>Rt (Chiralpak AD-H, 250 × 4.6 mm, IPA/nHeptane, TFA: 4/96, 0.1%) = 20.24 min. |
| Ex. 4-5-2-2 | Ethyl 2-(4-(2-((4-trifluoromethoxyphenyl)(hydroxy)methyl)cyclopropyl)-2,6-dimethylphenoxy)-2-methylpropanoate<br>Ex. 4-5-2, Protocol E, Yield: 44%. | (300 MHz, CDCl$_3$): 0.94-1.01 (m, 1H); 1.08-1.16 (m, 1H); 1.33 (t, 3H, J = 7.3 Hz); 1.41-1.49 (m, 7H); 1.85-1.93 (m, 1H); 1.99 (d, 1H, J = 3.5 Hz); 2.13 (s, 6H); 4.26 (q, 2H, J = 7.3 Hz); 4.38 (dd, 1H, J = 7 Hz, 3.5 Hz); 6.58 (s, 2H); 7.2 (d, 2H, J = 8.3 Hz); 7.46 (d, 2H, J = 8.3 Hz)<br>Rt (Chiralpak AD-H, 250 × 4.6 mm, IPA/nHeptane, TFA: 4/96, 0.1%) = 30.08 min. |
| Ex. 4-6-1 | Ethyl 2-(4-(2-((4-trifluoromethoxyphenyl)(hydroxy)methyl)cyclopropyl)-2-methylphenoxy)-2-methylpropanoate<br>Ex. 3-6, Protocol B, Yield: 50%. | (250 MHz, CDCl$_3$): 0.88-1.04 (m, 2H); 1.26 (t, 3H, J = 7.1 Hz); 1.39-1.51 (m, 1H); 1.56 (s, 6H); 1.73-2.04 (m, 2H); 2.18 (s, 3H); 4.21-4.25 (m, 1H); 4.25 (q, 2H, J = 7.1 Hz); 6.54-6.59 (m, 1H); 6.76 (d, 1H, J = 8.4 Hz); 6.86 (d, 1H, J = 2.1 Hz); 7.21 (d, 2H, J = 8.6 Hz); 7.46 (d, 2H, J = 8.6 Hz)<br>Rf (petroleum ether/ethyl acetate, 7/3) = 0.50. |
| Ex. 4-6-2 | Ethyl 2-(4-(2-((4-trifluoromethoxyphenyl)(hydroxy)methyl)cyclopropyl)-2-methylphenoxy)-2-methylpropanoate<br>Ex. 3-6, Protocol B, Yield: 26%. | (250 MHz, CDCl$_3$): 0.93-1.21 (m, 2H); 1.27 (t, 3H, J = 7.1 Hz); 1.40-1.51 (m, 1H); 1.58 (s, 6H); 1.90-2.01 (m, 2H); 2.19 (s, 3H); 4.25 (q, 2H, J = 7.1 Hz); 4.37 (dd, 1H, J = 7.6 Hz, 3.3 Hz); 6.56 (d, 1H, J = 8.4 Hz); 6.70 (dd, 1H, J = 8.4 Hz, 2.0 Hz); 6.80 (d, 1H, J = 2.0 Hz); 7.22 (d, 2H, J = 8.6 Hz); 7.50 (d, 2H, J = 8.6 Hz)<br>Rf (petroleum ether/ethyl acetate, 7/3) = 0.34. |
| Ex. 4-7-1 | Ethyl 2-(4-(2-((4-propyloxyphenyl)(hydroxy)methyl)cyclopropyl)-2,6-dimethylphenoxy)-2-methylpropanoate<br>Ex. 3-7, Protocol B, Yield: 53%. | (250 MHz, CDCl$_3$): 0.82-0.97 (m, 1H); 1.04 (t, 3H, J = 7.4 Hz); 1.09-1.22 (m, 1H); 1.35 (t, 3H, J = 7.1 Hz); 1.45 (s, 6H); 1.45-1.52 (m, 1H); 1.73-1.87 (m, 3H); 2.15 (s, 6H); 3.93 (d, 2H, J = 6.6 Hz); 4.19 (dd, 1H, J = 7.9 Hz, J = 3.0 Hz); 4.28 (q, 2H, J = 7.1 Hz); 6.68 (s, 2H); 6.89 (d, 2H J = 8.6 Hz); 7.34 (d, 2H, J = 8.6 Hz)<br>Rf (petroleum ether/ethyl acetate, 7/3) = 0.41. |
| Ex. 4-7-2 | Ethyl 2-(4-(2-((4-propyloxyphenyl)(hydroxy)methyl)cyclopropyl)-2,6-dimethylphenoxy)-2-methylpropanoate<br>Ex. 3-7, Protocol B, Yield: 27%. | (250 MHz, CDCl$_3$): 0.85-0.96 (m, 1H); 1.03 (t, 3H, J = 7.4 Hz); 1.09-1.22 (m, 1H); 1.33 (t, 3H, J = 7.1 Hz); 1.42-1.48 (m, 7H); 1.72-1.85 (m, 3H); 2.12 (s, 6H); 3.91 (d, 2H, J = 6.6 Hz); 4.27 (q, 2H, J = 7.1 Hz); 4.34 (dd, 1H, J = 7.2 Hz, J = 2.2 Hz); 6.59 (s, 2H); 6.87 (d, 2H, J = 8.5 Hz); 7.33 (d, 2H, J = 8.5 Hz)<br>Rf (petroleum ether/ethyl acetate, 7/3) = 0.36. |

TABLE 4-1-continued

| | Systematic name | |
|---|---|---|
| Ex. | Starting materials, Protocol, purification, yield. | $^1$H NMR (MHZ, solvent) data |
| Ex. 4-8-1 | Ethyl 2-(4-(2-((4-trifluoromethylthiophenyl)(hydroxy)methyl)cyclopropyl)-2,6-dimethylphenoxy)-2-methylpropanoate | |
| | Ex. 3-8, Protocol B, Yield: 41%. | (400 MHz, CDCl$_3$): 0.86-0.92 (m, 1H); 0.93-0.96 (m, 1H); 1.32 (t, 3H, J = 7.1 Hz); 1.41-1.46 (m, 1H); 1.42 (s, 6H); 1.90-1.95 (m, 1H); 2.12 (s, 6H); 2.99-3.04 (m, 1H); 4.13-4.19 (m, 1H); 4.24 (q, 2H, J = 7.1 Hz); 6.64 (s, 2H); 7.42 (d, 2H, J = 8.2 Hz); 7.59 (d, 2H, J = 8.2 Hz) Rf (petroleum ether/ethyl acetate, 8/2) = 0.45. |
| Ex. 4-8-2 | Ethyl 2-(4-(2-((4-trifluoromethylthiophenyl)(hydroxy)methyl)cyclopropyl)-2,6-dimethylphenoxy)-2-methylpropanoate | |
| | Ex. 3-8, Protocol B, Yield: 18%. | (250 MHz, CDCl$_3$): 0.83-0.99 (m, 1H); 1.07-1.12 (m, 1H); 1.33 (t, 3H, J = 7.1 Hz); 1.40-1.46 (m, 1H); 1.42 (s, 6H); 1.84-1.90 (m, 1H); 2.11 (s, 6H); 4.25 (q, 2H, J = 7.1 Hz); 4.36-4.39 (m, 1H); 6.57 (s, 2H); 7.46 (d, 2H, J = 8.1 Hz) 7.61 (d, 2H, J = 8.1 Hz) Rf (petroleum ether/ethyl acetate, 8/2) = 0.34. |
| Ex. 4-9-1 | Ethyl 2-(4-(2-((2-fluoro-4-trifluoromethythiolphenyl)(hydroxy)methyl)cyclopropyl)-2,6-dimethylphenoxy)-2-methylpropanoate | |
| | Ex. 3-9, Protocol B Yield: 29%. | (250 MHz, CDCl$_3$): 0.87-0.95 (m, 1H); 1.05-1.12 (m, 1H); 1.35 (t, 3H, J = 7.1 Hz); 1.40-1.46 (m, 1H); 1.45 (s, 6H); 1.95-2.01 (m, 1H); 2.15 (s, 6H); 4.28 (q, 2H, J = 7.1 Hz); 4.63 (dd, 1H, J = 7.9 Hz 3.4 Hz); 6.66 (s, 2H); 7.29-7.37 (m, 1H); 7.41-7.48 (m, 1H); 7.69-7.75 (m, 1H) Rf (petroleum ether/ethyl acetate, 8/2) = 0.40. |
| Ex. 4-9-2 | Ethyl 2-(4-(2-((2-fluoro-4-trifluoromethythiolphenyl)(hydroxy)methyl)cyclopropyl)-2,6-dimethylphenoxy)-2-methylpropanoate | |
| | Ex. 3-9, Protocol B Yield: 20%. | (250 MHz, CDCl$_3$): 0.84-1.02 (m, 1H); 1.05-1.15 (m, 1H); 1.33 (t, 3H, J = 7.1 Hz); 1.40-1.46 (m, 1H); 1.43 (s, 6H); 1.92-2.02 (m, 1H); 2.12 (s, 6H); 4.26 (q, 2H, J = 7.1 Hz); 4.76 (dd, 1H, J = 7.2 Hz, 3.8 Hz); 6.57 (s, 2H); 7.27-7.36 (m, 1H); 7.41-7.47 (m, 1H); 7.67-7.74 (m, 1H) Rf (petroleum ether/ethyl acetate, 8/2) = 0.32. |
| Ex. 4-10-1 | Ethyl 2-(4-(2-((2-trifluoromethoxyphenyl)(hydroxy)methyl)cyclopropyl)-2,6-dimethylphenoxy)-2-methylpropanoate | |
| | Ex. 3-10, Protocol B Yield: 37%. | (250 MHz, CDCl$_3$): 0.84-0.96 (m, 1H); 1.01-1.10 (m, 1H); 1.35 (t, 3H, J = 7.1 Hz); 1.35-1.45 (m, 1H); 1.45 (s, 6H); 1.92-2.06 (m, 1H); 2.15 (s, 6H); 4.28 (q, 2H, J = 7.1 Hz); 4.66 (dd, 1H, J = 7.8 Hz, 3.5 Hz); 6.67 (s, 2H); 7.29-7.35 (m, 3H); 7.70 (dd, 1H, J = 5.6 Hz, 3.8 Hz) Rf (petroleum ether/ethyl acetate, 8/2) = 0.38. |
| Ex. 4-10-2 | Ethyl 2-(4-(2-((2-trifluoromethoxyphenyl)(hydroxy)methyl)cyclopropyl)-2,6-dimethylphenoxy)-2-methylpropanoate | |
| | Ex. 3-10, Protocol B Yield: 18%. | (250 MHz, CDCl$_3$): 0.90-0.97 (m, 1H); 1.07-1.15 (m, 1H); 1.31 (t, 3H, J = 7.1 Hz); 1.32-1.42 (m, 1H); 1.42 (s, 6H); 1.85-1.96 (m, 1H); 2.11 (s, 6H); 2.42-2.46 (m, 1H); 4.24 (q, 2H, J = 7.1 Hz); 4.74-4.79 (m, 1H); 6.56 (s, 2H); 7.21-7.28 (m, 3H); 7.65 (dd, 1H, J = 5.2 Hz, 4.1 Hz). Rf (petroleum ether/ethyl acetate, 8/2) = 0.29. |

TABLE 4-1-continued

| Ex. | Starting materials, Protocol, purification, yield. | $^1$H NMR (MHZ, solvent) data |
|---|---|---|
| Ex. 4-11-1 | Ethyl 2-(4-(2-(hydroxy(4-(trifluoromethoxy)phenyl)methyl)cyclopropyl)-2-isopropylphenoxy)-2-methylpropanoate<br>Ex. 3-11, Protocol B, 4 hours at 60° C.<br>Yield: 42%. | (250 MHz, CDCl3): 0.92-1.04 (m, 2H); 1.16-1.22 (m, 6H); 1.24 (t, 3H, J = 7.2 Hz); 1.41-1.51 (m, 1H); 1.57 (s, 6H); 1.98-2.07 (m, 1H); 3.26-3.38 (m, 1H); 4.18-4.29 (m, 3H); 6.53 (d, 1H, J = 8.3 Hz); 6.72 (dd, 1H, J = 8.3 Hz J = 2.2 Hz); 6.92 (d, 1H, J = 2.2 Hz); 7.22 (d, 2H, J = 8.7 Hz); 7.48 (d, 2H, J = 8.7 Hz) |
| Ex. 4-11-2 | Ethyl 2-(4-(2-(hydroxy(4-(trifluoromethoxy)phenyl)methyl)cyclopropyl)-2-isopropylphenoxy)-2-methylpropanoate<br>Ex. 3-11, Protocol B, 4 hours at 60° C.<br>Yield: 30%. | (250 MHz, CDCl3): 0.97-1.03 (m, 1H); 1.09-1.2 (m, 7H); 1.21 (t, 3H, J = 7.2 Hz); 1.36-1.43 (m, 1H); 1.56 (m, 6H); 1.89-1.97 (m, 1H); 3.19-3.37 (m, 1H); 4.21 (q, 2H, J = 7.2 Hz); 4.33-4.41 (m, 1H); 6.49 (d, 1H, J = 8.3 Hz); 6.64 (dd, 1H, J = 8.3 Hz J = 2.2 Hz); 6.84 (d, 1H, J = 2.2 Hz); 7.19 (d, 2H, J = 8.6 Hz); 7.48 (d, 2H, J = 8.6 Hz) |
| Ex. 4-12-1 | Ethyl 2-(4-(2-((2,4-bis(trifluoromethyl)phenyl)(hydroxy)methyl)cyclopropyl)-2,6-dimethylphenoxy)-2-methylpropanoate<br>Ex. 3-12, Protocol B, 4 hours at 60° C.<br>Yield: 35%<br>Eluent: petroleum ether/ethyl acetate: 9/1 | (250 MHz, CDCl$_3$): 0.84-0.94 (m, 1H); 1.01-1.09 (m, 1H); 1.34 (t, 3H, J = 7.2 Hz); 1.42-1.51 (m, 7H); 2.02-2.12 (m, 2H); 2.15 (s, 6H); 4.27 (q, 2H, J = 7.2 Hz); 4.79-4.86 (m, 1H); 6.65 (s, 2H); 7.83-7.92 (m, 2H); 8.04 (d, 1H, J = 8 Hz) |
| Ex. 4-12-2 | Ethyl 2-(4-(2-((2,4-bis(trifluoromethyl)phenyl)(hydroxy)methyl)cyclopropyl)-2,6-dimethylphenoxy)-2-methylpropanoate<br>Ex. 3-12, Protocol B, 4 hours at 60° C.<br>Yield: 17%<br>Eluent: petroleum ether/ethyl acetate: 9/1. | (250 MHz, CDCl$_3$): 0.85-0.99 (m, 1H); 1.11-1.22 (m, 1H); 1.30 (t, 3H, J = 7 Hz); 1.38-1.49 (m, 7H); 1.90-1.99 (m, 1H); 2.02 (br s, 1H); 2.09 (s, 6H); 4.23 (q, 2H, J = 7 Hz); 4.93-5.01 (m, 1H); 6.53 (s, 2H); 7.79-7.92 (m, 2H); 7.99 (d, 1H, J = 8.2 Hz) |
| Ex. 4-13-1 | Ehyl 2-(4-(2-(hydroxy(2-methoxy-4-(trifluoromethoxy)phenyl)methyl)cyclopropyl)-2,6-dimethylphenoxy)-2-methylpropanoate<br>Ex. 3-13, Protocol B, 4 hours at 60° C.<br>Yield: 35%<br>Eluent: petroleum ether/ethyl acetate: 9/1. | (250 MHz, CDCl$_3$): 0.88-0.98 (m, 2H); 1.38 (t, 3H, J = 7.2 Hz); 1.48 (s, 6H); 1.51-1.61 (m, 1H); 1.91-2.01 (m, 1H); 2.18 (s, 6H); 2.59 (d, 1H, J = 5.2 Hz); 3.90 (s, 3H); 4.31 (q, 2H, J = 7.2 Hz); 4.51 (dd, 1H, J = 7.8 Hz, 5.2 Hz); 6.71 (s, 2H); 6.75-6.79 (m, 1H); 6.83-6.91 (m, 1H); 7.45 (d, 1H, J = 8.4 Hz) |
| Ex. 4-13-2 | Ethyl 2-(4-(2-(hydroxy(2-methoxy-4-(trifluoromethoxy)phenyl)methyl)cyclopropyl)-2,6-dimethylphenoxy)-2-methylpropanoate<br>Ex. 3-13, Protocol B, 4 hours at 60° C.<br>Yield: 17%<br>Eluent: petroleum ether/ethyl acetate: 9/1 | (250 MHz, CDCl$_3$): 0.86-0.97 (m, 1H); 1.06-1.17 (m, 1H); 1.36 (t, 3H, J = 7.2 Hz); 1.47 (s, 6H); 1.49-1.64 (m, 1H); 1.84-1.91 (m, 1H); 2.16 (s, 6H); 2.63 (d, 1H, J = 4.7 Hz); 3.89 (s, 3H); 4.29 (q, 2H, J = 7.2 Hz); 4.63 (dd, 1H, J = 7.1 Hz, 4.7 Hz); 6.61 (s, 2H); 6.74-6.79 (m, 1H); 6.8-6.86 (m, 1H); 7.43 (d, 1H, J = 8.4 Hz) |
| Ex. 4-14-1 | Ethyl 2-(4-(2-((2-(hexyloxy)pheny)(hydroxy)methyl)cyclopropyl)-2,6-dimethylphenoxy)-2-methylpropanoate<br>Ex. 3-14, Protocol B, 4 hours at 60° C.<br>Yield: 24% (de = 80%). | (250 MHz, CDCl$_3$): 0.81-1.01 (m, 5H); 1.24-1.39 (m, 7H); 1.41-1.5 (m, 7H); 1.54-1.65 (m, 2H); 1.74-1.86 (m, 2H); 1.90-1.98 (m, 1H); 2.15 (s, 6H); 2.93 (d, 1H, J = 5.7 Hz); 4.02 (t, 2H, J = 6.5 Hz); 4.28 (q, 2H, J = 7 Hz); 4.44 (dd, 1H, J = 8 Hz, 5.7 Hz); 6.69 (s, 2H); 6.87-6.97 (m, 2H); 7.20-7.26 (m, 1H); 7.37 (dd, 1H, J = 7.5 Hz, J = 1.7 Hz) |

TABLE 4-1-continued

| | | Systematic name | |
|---|---|---|---|
| Ex. | Starting materials, Protocol, purification, yield. | | ¹H NMR (MHZ, solvent) data |
| Ex. 4-14-2 | Ethyl 2-(4-(2-((2-(hexyloxy)phenyl)(hydroxy)methyl)cyclopropyl)-2,6-dimethylphenoxy)-2-methylpropanoate | | |
| | Ex. 3-14, Protocol B, 4 hours at 60° C. Yield: 18%. | | (250 MHz, CDCl₃): 0.89-1.03 (m, 4H); 1.11-1.18 (m, 1H); 1.28-1.51 (m, 14H); 1.54-1.66 (m, 2H); 1.74-1.85 (m, 2H); 1.89-1.98 (m, 1H); 2.13 (s, 6H); 3.01 (d, 1H, J = 5 Hz); 4.02 (t, 2H, J = 6.5 Hz); 4.28 (q, 2H, J = 7 Hz); 4.52-4.59 (m, 1H); 6.59 (s, 2H); 6.85-6.96 (m, 2H); 7.18-7.24 (m, 1H); 7.31-7.37 (m, 1H) |
| Ex. 4-15-1 | Ethyl 2-(2-bromo-4-(2-(hydroxy(4-(trifluoromethoxy)phenyl)methyl)cyclopropyl)phenoxy)-2-methylpropanoate | | |
| | Ex. 3-15, Protocol B, 4 hours at 60° C. Yield: 49% | | (250 MHz, CDCl₃): 0.92-0.99-(m, 1H); 1.02-1.09 (m, 1H); 1.28 (t, 3H, J = 7 Hz); 1.39-1.49 (m, 1H); 1.59 (s, 6H); 1.94-2.02 (m, 1H); 2.04 (br s, 1H); 4.2-4.32 (m, 3H); 6.77 (d, 1H, J = 8.5 Hz); 6.89 (dd, 1H, J = 8.5 Hz, J = 2 Hz); 7.19-7.29 (m, 3H); 7.46 (d, 2H, J = 8.5 Hz) |
| Ex. 4-15-2 | Ethyl 2-(2-bromo-4-(2-(hydroxy(4-(trifluoromethoxy)phenyl)methyl)cyclopropyl)phenoxy)-2-methylpropanoate | | |
| | Ex. 3-15, Protocol B, 4 hours at 60° C. Yield: 32%. | | (250 MHz, CDCl₃): 0.92-1.04 (m, 1H); 1.12-1.21 (m, 1H); 1.26 (t, 3H, J = 7.2 Hz); 1.37-1.44 (m, 1H); 1.58 (s, 6H); 1.90-1.96 (m, 1H); 2.04 (br s, 1H); 4.23 (q, 2H, J = 7.2 Hz); 4.37-4.43 (m, 1H); 6.73 (d, 1H, J = 8.5 Hz); 6.79 (dd, 1H, J = 8.5 Hz, J = 2.2 Hz); 7.16-7.24 (m, 3H); 7.42-7.47 (m, 2H) |
| Ex. 4-16-1 | Ethyl 2-(2,6-difluoro-4-(2-(hydroxy(4-(trifluoromethoxy)phenyl)methyl)cyclopropyl)phenoxy)-2-methylpropanoate | | |
| | Ex. 3-16, Protocol B, 4 hours at 60° C. Yield: 33%. | | (250 MHz, CDCl₃): 0.89-0.99 (m, 1H); 1.06-1.14 (m, 1H); 1.31 (t, 3H, J = 7.2 Hz); 1.41-1.51 (m, 1H); 1.52 (s, 6H); 1.97-2.08 (m, 2H); 4.23 (q, 2H, J = 7.2 Hz); 4.30 (dd, 1H, J = 7.5 Hz J = 3 Hz); 6.54-6.64 (m, 2H); 7.21 (d, 2H, J = 8.5 Hz); 7.44 (d, 2H, J = 8.5 Hz) |
| Ex. 4-16-2 | Ethyl 2-(2,6-difluoro-4-(2-(hydroxy(4-(trifluoromethoxy)phenyl)methyl)cyclopropyl)phenoxy)-2-methylpropanoate | | |
| | Ex. 3-16, Protocol B, 4 hours at 60° C. Yield: 36%. | | (250 MHz, CDCl₃): 0.91-0.98 (m, 1H); 1.16-1.24 (m, 1H); 1.30 (t, 3H, J = 7.2 Hz); 1.39-1.47 (m, 1H); 1.51 (s, 6H); 1.86-1.96 (m, 1H); 4.22 (q, 2H, J = 7.2 Hz); 4.39-4.47 (m, 1H); 6.46-6.57 (m, 2H); 7.16-7.24 (m, 2H); 7.39-7.45 (m, 2H) |

Example 5

Figure 1B:
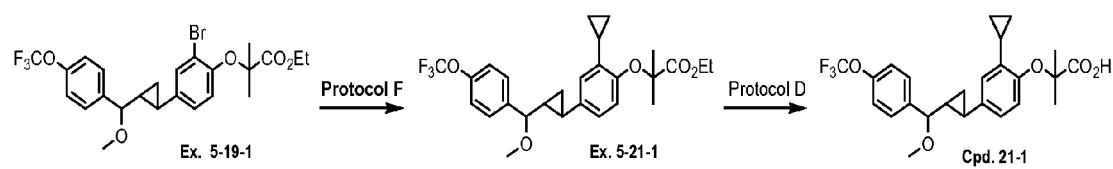
Figure 2:
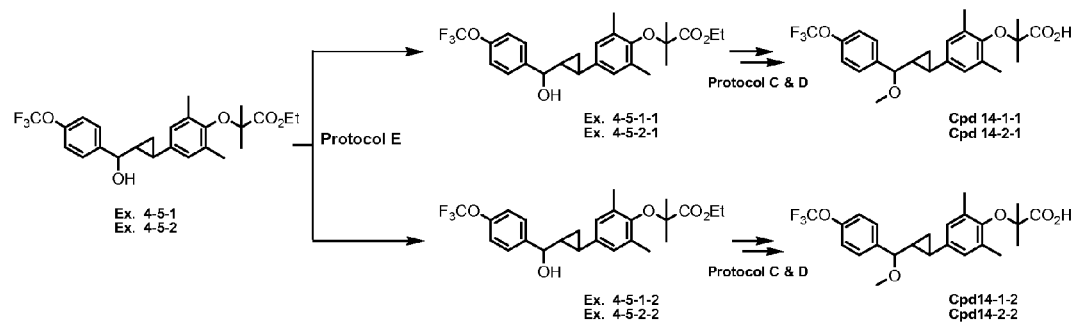
FIG. 2—General synthetic scheme of the Compounds of Formula (I) in their pure enantiomeric forms Compounds according to the invention can be prepared in their pure enantiomeric forms using synthetic methods known by the person skilled in the art such as asymmetric synthesis, enzymatic resolution, resolution via diastereoisomeric salt formation or chromatography using a chiral stationary phase. As an example, as depicted in FIG. 2, intermediate compounds from Example 4 have been separated by HPLC chiral chromatography to generate pure enantiomers. Using Protocol C and D, those enantiomers are subsequently modified as summarized in Examples 5 and 6 to generate enantiopure compounds according to the invention.

Synthesis of Intermediate of (Alkoxy(Phenyl)Methyl)Cyclopropyle Derivatives According to the Invention The synthesis of those intermediate compounds as depicted in FIGS. 1a & 2 and summarized in Table 5-1 was realized using the Protocol C described in Example 1; otherwise, any specific changes in conditions of elution or reaction conditions are reported. In the event some transesterification occurred, only the NMR of the major ester form, generally ethyl ester, has been reported. As an example of how further substitutions may be introduced, Ex 5-21-1 was prepared from Ex 5-19-1 using Protocol F as depicted in FIG. 1b.

TABLE 5-1

| | | Systematic name | |
|---|---|---|---|
| Ex. | Starting materials, Protocol: specific conditions, purification, yield. | | ¹H NMR (solvent) data |
| Ex. 5-1-1 | Ethyl 2-(4-(2-(methoxy(4-bromophenyl)methyl)cyclopropyl)-2,6-dimethylphenoxy)-2-methylpropanoate | | |
| | Ex. 4-1-1 and methyl iodide, Procotol C, Yield: 40%. | | (300 MHz, CDCl₃): 0.76-0.88 (m, 2H); 1.34-1.39 (m, 1H); 1.34 (t, 3H, J = 7.1 Hz); 1.56 (s, 6H); 1.92-1.96 (m, 1H); 2.14 (s, 6H); 3.29 (s, 3H); 3.72 (d, |

TABLE 5-1-continued

| Ex. | Systematic name<br>Starting materials, Protocol:<br>specific conditions,<br>purification, yield. | ¹H NMR (solvent) data |
|---|---|---|
| | | 1H, J = 7.6 Hz); 4.28 (q, 2H, J = 7.1 Hz);<br>6.64 (s, 2H); 7.23 (d, 2H, J = 8.4 Hz);<br>7.49 (d, 2H, J = 8.4 Hz). |
| Ex. 5-1-2 | Ethyl 2-(4-(2-(methoxy(4-bromophenyl)methyl)cyclopropyl)-2,6-dimethylphenoxy)-2-methylpropanoate<br>Ex. 4-1-2 and methyl iodide,<br>Procotol C,<br>Yield: 68%. | (300 MHz, CDCl₃): 0.76-0.88 (m, 1H);<br>0.96-1.04 (m, 1H); 1.32-1.37 (m, 4H);<br>1.42 (s, 6H); 1.75-1.78 (m, 1H); 2.13 (s,<br>6H); 3.29 (s, 3H); 3.89 (d, 1H, J = 6.4<br>Hz); 4.28 (q, 2H, J = 7.1 Hz); 6.53 (s,<br>2H); 7.23 (d, 2H, J = 8.4 Hz); 7.48 (d, 2H,<br>J = 8.4 Hz) |
| Ex. 5-2-1 | Ethyl 2-(4-(2-(methoxy(4-methylphenyl)methyl)cyclopropyl)-2,6-dimethylphenoxy)-2-methylpropanoate<br>Ex. 4-2-1 and methyl iodide,<br>Procotol C,<br>Yield: 75%. | (300 MHz, CDCl₃): 0.76-0.90 (m, 2H);<br>1.34 (t, 3H, J = 7.1 Hz); 1.44-1.49 (m,<br>1H); 1.47 (s, 6H); 1.86-1.96 (m, 1H);<br>2.16 (s, 6H); 2.39 (s, 3H); 3.29 (s, 3H);<br>3.75 (d, 1H, J = 7.7 Hz); 4.30 (q, 2H,<br>J = 7.1 Hz); 6.68 (s, 2H); 7.20 (d, 2H,<br>J = 8.1 Hz); 7.26 (d, 2H, J = 8.1 Hz). |
| Ex. 5-3-1 | Ethyl 2-(4-(2-(methoxy(4-(methylthio)phenyl)methyl)cyclopropyl)-2,6-dimethylphenoxy)-2-methylpropanoate<br>Ex. 4-3-1 and methyl iodide,<br>Procotol C,<br>Yield: 25%. | (250 MHz, CDCl₃): 0.76-0.90 (m, 2H);<br>1.34 (t, 3H, J = 7.1 Hz); 1.44-1.49 (m,<br>1H); 1.47 (s, 6H); 1.84-1.94 (m, 1H);<br>2.14 (s, 6H); 2.50 (s, 3H); 3.26 (s, 3H);<br>3.73 (d, 1H, J = 7.6 Hz); 4.30 (q, 2H,<br>J = 7.1 Hz); 6.65 (s, 2H); 7.23-7.32 (m,<br>4H). |
| Ex. 5-3-2 | Ethyl 2-(4-(2-(methoxy(4-(methylthio)phenyl)methyl)cyclopropyl)-2,6-dimethylphenoxy)-2-methylpropanoate<br>Ex. 4-3-2 and methyl iodide,<br>Procotol C,<br>Yield: 43%. | (400 MHz, CDCl₃): 0.85-0.96 (m, 1H);<br>1.04-1.14 (m, 1H); 1.33 (t, 3H,<br>J = 7.1 Hz); 1.42-1.46 (m, 1H); 1.42 (s,<br>6H); 1.71-1.78 (m, 1H); 2.11 (s, 6H);<br>2.48 (s, 3H); 3.25 (s, 3H); 3.89 (d, 1H,<br>J = 6.5 Hz); 4.28 (q, 2H, J = 7.1 Hz); 6.56<br>(s, 2H); 7.20-7.32 (m, 4H). |
| Ex. 5-4-1 | Ethyl 2-(4-(2-(methoxy(4-(trifluoromethyl)phenyl)methyl)cyclopropyl)-2,6-dimethylphenoxy)-2-methylpropanoate<br>Ex. 4-4-1 and methyl iodide,<br>Procotol C,<br>Yield: 56%. | (300 MHz, CDCl₃): 0.80-0.93 (m, 2H);<br>1.24-1.29 (m, 1H); 1.34 (t, 3H,<br>J = 7.1 Hz); 1.44 (s, 6H); 1.92-1.96 (m,<br>1H); 2.13 (s, 6H); 3.29 (s, 3H); 3.81 (d,<br>1H, J = 7.9 Hz); 4.27 (q, 2H, J = 7.1 Hz);<br>6.64 (s, 2H); 7.47 (d, 2H, J = 8.2 Hz);<br>7.63 (d, 2H, J = 8.2 Hz). |
| Ex. 5-4-2 | Ethyl 2-(4-(2-(methoxy(4-(trifluoromethyl)phenyl)methyl)cyclopropyl)-2,6-dimethylphenoxy)-2-methylpropanoate<br>Ex. 4-4-2 and methyl iodide,<br>Procotol C,<br>Yield: 55%. | (400 MHz, CDCl₃): 0.90-0.98 (m, 1H);<br>1.09-1.16 (m, 1H); 1.33 (t, 3H,<br>J = 7.1 Hz); 1.40-1.46 (m, 1H); 1.42 (s,<br>6H); 1.78-1.85 (m, 1H); 2.10 (s, 6H);<br>3.28 (s, 3H); 4.00 (d, 1H, J = 6.4 Hz);<br>4.26 (q, 2H, J = 7.1 Hz); 6.53 (s, 2H);<br>7.47 (d, 2H, J = 8.6 Hz); 7.62 (d, 2H,<br>J = 8.6 Hz). |
| Ex. 5-5-1 | Ethyl 2-(4-(2-(butyloxy(4-(trifluoromethoxy)phenyl)methyl)cyclopropyl)-2,6-dimethylphenoxy)-2-methylpropanoate<br>Ex. 4-5-1 and butyl iodide,<br>Procotol C,<br>Yield: 55%. | (250 MHz, CDCl₃): 0.77-1.06 (m, 5H);<br>1.28-1.45 (m, 6H); 1.48 (s, 6H); 1.51-<br>1.65 (m, 2H); 1.86-2.03 (m, 1H); 2.17<br>(s, 6H); 3.37-3.42 (m, 2H); 3.94 (d, 1H,<br>J = 7.2 Hz); 4.30 (q, 2H, J = 7.1 Hz); 6.67<br>(s, 2H); 7.22 (d, 2H, J = 8.1 Hz); 7.41 (d,<br>2H, J = 8.1 Hz). |
| Ex. 5-5-2 | Ethyl 2-(4-(2-(butyloxy(4-(trifluoromethoxy)phenyl)methyl)cyclopropyl)-2,6-dimethylphenoxy)-2-methylpropanoate<br>Ex. 4-5-2 and butyl iodide,<br>Procotol C,<br>Yield: 59%. | (250 MHz, CDCl₃): 0.90-1.00 (m, 4H);<br>1.14-1.20 (m, 1H); 1.28-1.45 (m, 6H);<br>1.48 (s, 6H); 1.65-1.87 (m, 3H); 2.13 (s,<br>6H); 3.35-3.40 (m, 2H); 4.05 (d, 1H,<br>J = 7.2 Hz); 4.29 (q, 2H, J = 7.1 Hz); 6.56 |

TABLE 5-1-continued

| Ex. | Systematic name / Starting materials, Protocol: specific conditions, purification, yield. | $^1$H NMR (solvent) data |
|---|---|---|
| | | (s, 2H); 7.21 (d, 2H, J = 8.1 Hz); 7.40 (d, 2H, J = 8.1 Hz). |
| Ex. 5-6-1 | 2-Cyclohexylethyl 2-(4-(2-(cyclohexylethyloxy(4-(trifluoromethoxy)phenyl)methyl) cyclopropyl)-2,6-dimethylphenoxy)-2-methylpropanoate<br>Ex. 4-5-1 and (2-bromoethyl)cyclohexane,<br>Protocol C: NaH 3.2 eq. - (2-bromoethyl)cyclohexane 2.4 eq.,<br>Yield: 60%. | (250 MHz, CDCl$_3$): 0.75-2.03 (m, 26H); 2.17 (s, 6H); 3.39-3.48 (m, 2H); 3.89 (d, 1H, J = 7.2 Hz); 4.26 (q, 2H, J = 6.9 Hz); 6.67 (s, 2H); 7.22 (d, 2H, J = 8.1 Hz); 7.41 (d, 2H, J = 8.1 Hz). |
| Ex. 5-6-2 | 2-Cyclohexylethyl l 2-(4-(2-(cyclohexylethyloxy(4-(trifluoromethoxy)phenyl)methyl) cyclopropyl)-2,6-dimethylphenoxy)-2-methylpropanoate<br>Ex. 4-5-2 and (2-bromoethyl)cyclohexane,<br>Protocol C: NaH 3.2 eq. - (2-bromoethyl)cyclohexane 2.4 eq.,<br>Yield: 59%. | (250 MHz, CDCl$_3$): 0.75-2.03 (m, 26H); 2.17 (s, 6H); 3.39-3.48 (m, 2H); 4.04 (d, 1H, J = 7.2 Hz); 4.26 (q, 2H, J = 6.9 Hz); 6.56 (s, 2H); 7.22 (d, 2H, J = 8.1 Hz); 7.41 (d, 2H, J = 8.1 Hz). |
| Ex. 5-7-1 | Ethyl 2-(4-(2-(methoxy(4-(trifluoromethoxy)phenyl)methyl)cyclopropyl)-2-methylphenoxy)-2-methylpropanoate<br>Ex. 4-6-1 and methyl iodide,<br>Procotol C,<br>Yield: 65%. | (250 MHz, CDCl$_3$): 0.80-0.91 (m, 2H); 1.26 (t, 3H, J = 7.1 Hz); 1.31-1.40 (m, 1H); 1.55 (m, 6H); 1.91-1.99 (m, 1H); 2.18 (s, 3H); 3.29 (s, 3H); 3.78 (d, 1H, J = 7.3 Hz); 4.23 (q, 2H, J = 7.1 Hz); 6.53 (d, 1H, 8.4 Hz); 6.74 (dd, 1H, J = 8.4 Hz, J = 1.5 Hz); 6.84 (d, 1H, J = 1.5 Hz); 7.21 (d, 2H, J = 8.6 Hz); 7.37 (d, 2H, J = 8.6 Hz). |
| Ex. 5-7-2 | Ethyl 2-(4-(2-(methoxy(4-(trifluoromethoxy)phenyl)methyl)cyclopropyl)-2-methylphenoxy)-2-methylpropanoate<br>Ex. 4-6-2 and methyl iodide,<br>Procotol C,<br>Yield: 65%. | (250 MHz, CDCl$_3$): 0.87-0.94 (m, 2H); 1.03-1.11 (m, 1H); 1.23 (t, 3H, J = 7.1 Hz); 1.54 (m, 6H); 1.76-1.83 (m, 1H); 2.14 (s, 3H); 3.28 (s, 3H); 3.88 (d, 1H, J = 6.9 Hz); 4.22 (q, 2H, J = 7.1 Hz); 6.47 (d, 1H, J = 8.4 Hz); 6.62 (dd, 1H, J = 8.4 Hz, J = 1.8 Hz); 6.71 (d, 1H, J = 1.8 Hz); 7.21 (d, 2H, J = 8.6 Hz); 7.37 (d, 2H, J = 8.6 Hz). |
| Ex. 5-8-1 | Ethyl 2-(4-(2-(methoxy(4-(propyloxy)phenyl)methyl)cyclopropyl)-2,6-dimethylphenoxy)-2-methylpropanoate<br>Ex. 4-7-1 and methyl iodide,<br>Procotol C,<br>Yield: 61%. | (250 MHz, CDCl$_3$): 0.76-0.90 (m, 2H); 1.05 (t, 3H, J = 7.3 Hz); 1.34 (t, 3H, J = 7.1 Hz); 1.42-1.46 (m, 1H); 1.44 (s, 6H); 1.64-1.78 (m, 2H); 1.78-1.86 (m, 1H); 2.14 (s, 6H); 3.25 (s, 3H); 3.72 (d, J = 7.6 Hz, 1H); 3.93 (t, 2H, J = 6.5 Hz); 4.28 (q, 2H, J = 7.1 Hz); 6.65 (s, 2H); 6.89 (d, 2H, J = 8.6 Hz); 7.25 (d, 2H, J = 8.6 Hz). |
| Ex. 5-8-2 | Ethyl 2-(4-(2-(methoxy(4-(propyloxy)phenyl)methyl)cyclopropyl)-2,6-dimethylphenoxy)-2-methylpropanoate<br>Ex. 4-7-2 and methyl iodide,<br>Procotol C,<br>Yield: 75%. | (400 MHz, CDCl$_3$): 0.85-0.99 (m, 2H); 1.00-1.10 (m, 3H); 1.33 (t, 3H, J = 7.1 Hz); 1.40-1.46 (m, 7H); 1.70-1.82 (m, 3H); 2.09 (s, 6H); 3.24 (s, 3H); 3.88 (d, 1H, J = 6.7 Hz); 3.91 (t, 2H, J = 6.5 Hz); 4.26 (q, 2H, J = 7.1 Hz); 6.55 (s, 2H); 6.88 (d, 2H, J = 8.6 Hz); 7.23 (d, 2H, J = 8.6 Hz). |
| Ex. 5-9-1 | Ethyl 2-(4-(2-(methoxy(4-(trifluoromethylthio)phenyl)methyl)cyclopropyl)-2,6-dimethylphenoxy)-2-methylpropanoate<br>Ex. 4-8-1 and methyl iodide,<br>Procotol C,<br>Yield: 57%. | (250 MHz, CDCl$_3$): 0.76-0.88 (m, 2H); 1.34-1.39 (m, 1H); 1.34 (t, 3H, J = 7.1 Hz); 1.44 (s, 6H); 1.92-1.96 (m, 1H); 2.14 (s, 6H); 3.30 (s, 3H); 3.77 (d, 1H, J = 7.6 Hz); 4.28 (q, 2H, J = 7.1 Hz); 6.65 (s, 2H); 7.41 (d, 2H, J = 8.1 Hz); 7.66 (d, 2H, J = 8.1 Hz). |

TABLE 5-1-continued

| Ex. | Starting materials, Protocol: specific conditions, purification, yield. | $^1$H NMR (solvent) data |
|---|---|---|
| | Systematic name | |
| Ex. 5-10-1 | Ethyl 2-(4-(2-(ethoxy(4-(trifluoromethoxy)phenyl)methyl)cyclopropyl)-2,6-dimethylphenoxy)-2-methylpropanoate | |
| | Ex. 4-5-1 and ethyl iodide, Procotol C, Yield: 75%. | (250 MHz, CDCl$_3$): 0.76-1.03 (m, 2H); 1.22 (t, 3H, J = 7.0 Hz); 1.37 (t, 3H, J = 7.1 Hz); 1.38-1.43 (m, 1H); 1.47 (s, 6H); 1.86-1.96 (m, 1H); 2.17 (s, 6H); 3.37-3.57 (m, 2H); 3.94 (d, 1H, J = 7.4 Hz); 4.30 (q, 2H, J = 7.1 Hz); 6.67 (s, 2H); 7.23 (d, 2H, J = 8.1 Hz); 7.41 (d, 2H, J = 8.1 Hz). |
| Ex. 5-10-2 | Ethyl 2-(4-(2-(ethoxy(4-(trifluoromethoxy)phenyl)methyl)cyclopropyl)-2,6-dimethylphenoxy)-2-methylpropanoate | |
| | Ex. 4-5-2 and ethyl iodide, Procotol C, Yield: 80%. | (250 MHz, CDCl$_3$): 0.86-1.03 (m, 1H); 1.11-1.27 (m, 4H); 1.35 (t, 3H, J = 7.1 Hz); 1.38-1.43 (m, 1H); 1.45 (s, 6H); 1.78-1.86 (m, 1H); 2.13 (s, 6H); 3.44 (q, 2H, J = 7.1 Hz); 4.04 (d, 1H, J = 6.5 Hz); 4.29 (q, 2H, J = 7.1 Hz); 6.56 (s, 2H); 7.22 (d, 2H, J = 8.1 Hz); 7.41 (d, 2H, J = 8.1 Hz). |
| Ex. 5-11-1 | Ethyl 2-(4-(2-(benzyloxy(4-(trifluoromethoxy)phenyl)methyl)cyclopropyl)-2,6-dimethylphenoxy)-2-methylpropanoate | |
| | Ex. 4-5-1 and benzyl bromide, Procotol C: NaH 3.2 eq. - benzylbromide 2.4 eq., Yield: 60%. | (250 MHz, CDCl$_3$): 0.82-0.94 (m, 2H); 1.37 (t, 3H, J = 7.1 Hz); 1.47 (s, 6H); 1.45-1.49 (m, 1H); 1.91-1.95 (m, 1H); 2.15 (s, 6H); 3.99 (d, 1H, J = 7.4 Hz); 4.30 (q, 2H, J = 7.1 Hz); 4.37 (d, 1H, J = 12.1 Hz); 4.56 (d, 1H, J = 12.1 Hz); 6.67 (s, 2H); 7.10-7.50 (m, 9H). |
| Ex. 5-11-2 | Ethyl 2-(4-(2-(benzyloxy(4-(trifluoromethoxy)phenyl)methyl)cyclopropyl)-2,6-dimethylphenoxy)-2-methylpropanoate | |
| | Ex. 4-5-2 and benzyl bromide, Procotol C: NaH 3.2 eq. - benzylbromide 2.4 eq., Yield: 60%. | (250 MHz, CDCl$_3$): 0.86-1.02 (m, 1H); 1.11-1.21 (m, 1H); 1.37 (t, 3H, J = 7.1 Hz); 1.35-1.43 (m, 1H); 1.45 (s, 6H); 1.71-1.90 (m, 1H); 2.15 (s, 6H); 4.16 (d, 1H, J = 7.4 Hz); 4.30 (q, 2H, J = 7.1 Hz); 4.37 (d, 1H, J = 12.1 Hz); 4.56 (d, 1H, J = 12.1 Hz); 6.56 (s, 2H); 7.10-7.50 (m, 9H). |
| Ex. 5-12-1 | Ethyl 2-(4-(2-(methoxy(2-fluoro-4-(trifluoromethyl)phenyl)methyl)cyclopropyl)-2,6-dimethylphenoxy)-2-methylpropanoate | |
| | Ex. 4-9-1 and methyl iodide, Procotol C, Yield: 57%. | (250 MHz, CDCl$_3$): 0.80-0.93 (m, 2H); 1.34 (t, 3H, J = 7.1 Hz); 1.34-1.44 (m, 1H); 1.44 (s, 6H); 1.92-1.96 (m, 1H); 2.13 (s, 6H); 3.31 (s, 3H); 4.21 (d, 1H, J = 8.2 Hz); 4.29 (q, 2H, J = 7.1 Hz); 6.65 (s, 2H); 7.42-7.48 (m, 2H); 7.6-7.67 (m, 1H). |
| Ex. 5-12-2 | Ethyl 2-(4-(2-(methoxy(2-fluoro-4-(trifluoromethyl)phenyl)methyl)cyclopropyl)-2,6-dimethylphenoxy)-2-methylpropanoate | |
| | Ex. 4-9-2 and methyl iodide, Procotol C, Yield: 48%. | (400 MHz, CDCl$_3$): 0.90-0.98 (m, 1H); 1.06-1.14 (m, 1H); 1.33 (t, 3H, J = 7.1 Hz); 1.40-1.46 (m, 1H); 1.42 (s, 6H); 1.85-1.93 (m, 1H); 2.10 (s, 6H); 3.30 (s, 3H); 4.26 (q, 2H, J = 7.1 Hz); 4.36 (d, 1H, J = 6.8 Hz); 6.54 (s, 2H); 7.29-7.38 (m, 1H); 7.41-7.47 (m, 1H); 7.56-7.63 (m, 1H). |
| Ex. 5-13-1 | Ethyl 2-(4-(2-(methoxy(2-(trifluoromethyloxy)phenyl)methyl)cyclopropyl)-2,6-dimethylphenoxy)-2-methylpropanoate | |
| | Ex. 4-10-1 and methyl iodide, Procotol C, Yield: 83%. | (250 MHz, CDCl$_3$): 0.73-0.82 (m, 1H); 0.91-1.01 (m, 1H); 1.34 (t, 3H, J = 7.1 Hz); 1.44 (s, 6H); 1.35-1.49 (m, 1H); 1.88-1.99 (m, 1H); 2.13 (s, 6H); 3.26 (s, 3H); 4.24 (d, 1H, J = 7.5 Hz); 4;28 (q, 2H, J = 7;1 Hz); 6.64 (s, 2H); 7.24-7.28 (m, 1H); 7.30-7.34 (m, 2H); 7.55-7.64 (m, 1H). |
| Ex. 5-13-2 | Ethyl 2-(4-(2-(methoxy(2-(trifluoromethyloxy)phenyl)methyl)cyclopropyl)-2,6-dimethylphenoxy)-2-methylpropanoate | |
| | Ex. 4-10-2 and methyl iodide, Procotol C, Yield: 83%. | (250 MHz, CDCl$_3$): 0.84-0.96 (m, 2H); 1.05-1.14 (m, 1H); 1.32 (t, 3H, J = 7.1 Hz); 1.42 (s, 6H); 1.35-1.45 (m, 1H); 1.74-1.98 (m, 1H); 2.10 (s, 6H); |

TABLE 5-1-continued

| Ex. | Starting materials, Protocol: specific conditions, purification, yield. | $^1$H NMR (solvent) data |
|---|---|---|
| | Systematic name | |
| | | 3.25 (s, 3H); 4.26 (q, 2H, J = 7.1 Hz); 4.35 (d, 1H, J = 7.5 Hz); 6.53 (s, 2H); 7.27-7.31 (m, 3H); 7.56 (dd, 1H, J = 5.6 Hz, 3.8 Hz). |
| Ex. 5-14-1 | Ethyl 2-(4-(2-(methoxy(4-(trifluoromethoxy)phenyl)methyl)cyclopropyl)-2,6-dimethylphenoxy)-2-methylpropanoate | |
| | Ex. 4-5-1 and methyl iodide, Procotol C: NaH 2 eq.- MeI 1.8 eq. −10° C., Yield: 55%. Eluent: cyclohexane/ethyl acetate: 9/1. | (300 MHz, CDCl$_3$): 0.80-0.92 (m, 2H); 1.35 (t, 3H, J = 7.3 Hz); 1.37-1.44 (m, 1H); 1.45 (s, 6H); 1.90-1.98 (m, 1H); 2.15 (s, 6H); 3.30 (s, 3H); 3.77 (d, 1H, J = 7.9 Hz); 4.28 (q, 2H, J = 7.3 Hz); 6.68 (s, 2H); 7.22 (d, 2H, J = 8.5 Hz); 7.47 (d, 2H, J = 8.5 Hz) |
| Ex. 5-14-2 | Ethyl 2-(4-(2-(methoxy(4-(trifluoromethoxy)phenyl)methyl)cyclopropyl)-2,6-dimethylphenoxy)-2-methylpropanoate | |
| | Ex. 4-5-2 and methyl iodide, Procotol C: −10° C., Yield: 51%. Eluent: cyclohexane/ethyl acetate: 9/1. | (300 MHz, CDCl$_3$): 0.92-0.99 (m, 1H); 1.08-1.16 (m, 1H); 1.31-1.41 (m, 4H); 1.43 (s, 6H); 1.75-1.84 (m, 1H); 2.11 (s, 6H); 3.29 (s, 3H); 3.95 (d, 1H, J = 6.4 Hz); 4.26 (q, 2H, J = 7.3 Hz); 6.54 (s, 2H); 7.20 (d, 2H, J = 8.5 Hz); 7.38 (d, 2H, J = 8.5 Hz) |
| Ex. 5-14-1-1 | Ethyl 2-(4-(2-(methoxy(4-(trifluoromethoxy)phenyl)methyl)cyclopropyl)-2,6-dimethylphenoxy)-2-methylpropanoate | |
| | Ex. 4-5-1-1 and methyl iodide, Procotol C: −10° C., Yield: 60%. Eluent: cyclohexane/ethyl acetate: 9/1. | (300 MHz, CDCl$_3$): 0.80-0.92 (m, 2H); 1.35 (t, 3H, J = 7.3 Hz); 1.37-1.44 (m, 1H); 1.45 (s, 6H); 1.90-1.98 (m, 1H); 2.15 (s, 6H); 3.30 (s, 3H); 3.77 (d, 1H, J = 7.9 Hz); 4.28 (q, 2H, J = 7.3 Hz); 6.68 (s, 2H); 7.22 (d, 2H, J = 8.5 Hz); 7.40 (d, 2H, J = 8.5 Hz) |
| Ex. 5-14-1-2 | Ethyl 2-(4-(2-(methoxy(4-(trifluoromethoxy)phenyl)methyl)cyclopropyl)-2,6-dimethylphenoxy)-2-methylpropanoate | |
| | Ex. 4-5-1-2 and methyl iodide, Procotol C: −10° C., Yield: 64%. Eluent: cyclohexane/ethyl acetate: 9/1. | (300 MHz, CDCl$_3$): 0.80-0.92 (m, 2H); 1.35 (t, 3H, J = 7.3 Hz); 1.37-1.44 (m, 1H); 1.45 (s, 6H); 1.90-1.98 (m, 1H); 2.15 (s, 6H); 3.30 (s, 3H); 3.77 (d, 1H, J = 7.9 Hz); 4.28 (q, 2H, J = 7.3 Hz); 6.68 (s, 2H); 7.22 (d, 2H, J = 8.5 Hz); 7.40 (d, 2H, J = 8.5 Hz) |
| Ex. 5-14-2-1 | Ethyl 2-(4-(2-(methoxy(4-(trifluoromethoxy)phenyl)methyl)cyclopropyl)-2,6-dimethylphenoxy)-2-methylpropanoate | |
| | Ex. 4-5-2-1 and methyl iodide, Procotol C, Yield: 79%. | (300 MHz, CDCl$_3$): 0.92-0.99 (m, 1H); 1.08-1.16 (m, 1H); 1.31-1.41 (m, 4H); 1.43 (s, 6H); 1.75-1.84 (m, 1H); 2.11 (s, 6H); 3.29 (s, 3H); 3.95 (d, 1H, J = 6.4 Hz); 4.26 (q, 2H, J = 7.3 Hz); 6.54 (s, 2H); 7.20 (d, 2H, J = 8.5 Hz); 7.38 (d, 2H, J = 8.5 Hz) |
| Ex. 5-14-2-2 | Ethyl 2-(4-(2-(methoxy(4-(trifluoromethoxy)phenyl)methyl)cyclopropyl)-2,6-dimethylphenoxy)-2-methylpropanoate | |
| | Ex. 4-5-2-2 and methyl iodide, Procotol C, Yield: 84%. | (300 MHz, CDCl$_3$): 0.92-0.99 (m, 1H); 1.08-1.16 (m, 1H); 1.31-1.41 (m, 4H); 1.43 (s, 6H); 1.75-1.84 (m, 1H); 2.11 (s, 6H); 3.29 (s, 3H); 3.95 (d, 1H, J = 6.4 Hz); 4.26 (q, 2H, J = 7.3 Hz); 6.54 (s, 2H); 7.20 (d, 2H, J = 8.5 Hz); 7.38 (d, 2H, J = 8.5 Hz) |
| Ex. 5-15-1 | Ethyl 2-(2-isopropyl-4-(2-(methoxy(4-(trifluoromethoxy)phenyl)methyl)cyclopropyl)phenoxy)-2-methylpropanoate | |
| | Ex. 4-11-1 and methyl iodide, Procotol C, Yield: 52%. | (250 MHz, CDCl$_3$): 0.76-0.89 (m, 1H); 1.1-1.21 (m, 6H); 1.22 (t, 3H, J = 7.2 Hz); 1.29-1.37 (m, 1H); 1.54 (s, 6H); 1.91-1.98 (m, 1H); 3.22-3.34 (m, 4H); 3.8 (d, 1H, J = 7.5 Hz); 4.2 (q, 2H, J = 7.2 Hz); 6.5 (d, 1H, J = 8.3 Hz); 6.69 (dd, 1H, J = 8.3 Hz J = 2.2 Hz); 6.87 (d, 1H, J = 2.2 Hz); 7.19 (d, 2H, J = 8.7 Hz); 7.36 (d, 2H, J = 8.7 Hz) |
| Ex. 5-15-2 | Ethyl 2-(2-isopropyl-4-(2-(methoxy(4-(trifluoromethoxy)phenyl)methyl)cyclopropyl)phenoxy)-2-methylpropanoate | |
| | Ex. 4-11-2 and methyl iodide, Procotol C, Yield: 47%. | (250 MHz, CDCl$_3$): 0.93-1.01 (m, 1H); 1.06-1.14 (m, 7H); 1.19-1.33 (m, 4H); 1.53 (s, 6H); 1.77-1.85 (m, 1H); 3.17- |

TABLE 5-1-continued

| | Systematic name | |
|---|---|---|
| Ex. | Starting materials, Protocol: specific conditions, purification, yield. | $^1$H NMR (solvent) data |
| | | 3.29 (m, 1H); 3.27 (s, 3H); 3.85 (d, 1H, J = 7 Hz); 4.18 (q, 2H, J = 7.2 Hz); 6.44 (d, 1H, J = 8.5 Hz); 6.58 (dd, 1H, J = 8.5 Hz J = 2.1 Hz); 6.75 (d, 1H, J = 2.1 Hz); 7.18 (d, 2H, J = 8.5 Hz); 7.36 (d, 2H, J = 8.5 Hz) |
| Ex. 5-16-1 | Ethyl 2-(4-(2-((2,4-bis(trifluoromethyl)phenyl)(methoxy)methyl)cyclopropyl)-2,6-dimethylphenoxy)-2-methylpropanoate | |
| | Ex. 4-12-1 and methyl iodide, Procotol C, Yield: 83%. | (250 MHz, CDCl$_3$): 0.77-0.82 (m, 1H); 0.98-1.06 (m, 1H); 1.31-1.41 (m, 4H); 1.44 (s, 6H); 1.99-2.09 (m, 1H); 2.14 (s, 6H); 3.21 (s, 3H); 4.28 (q, 2H, J = 7.1 Hz); 4.38 (d, 1H, J = 5.7 Hz); 6.64 (s, 2H); 7.83-7.99 (m, 3H) |
| Ex. 5-16-2 | Ethyl 2-(4-(2-((2,4-bis(trifluoromethyl)phenyl)(methoxy)methyl)cyclopropyl)-2,6-dimethylphenoxy)-2-methylpropanoate | |
| | Ex. 4-12-2 and methyl iodide, Procotol C, Yield: 90%. | (250 MHz, CDCl$_3$): 0.85-0.95 (m, 1H); 1.14-1.26 (m, 1H); 1.30-1.42 (m, 4H); 1.42 (s, 6H); 1.93-2.01 (m, 1H); 2.11 (s, 6H); 3.19 (s, 3H); 4.26 (q, 2H, J = 7.2 Hz); 4.51-4.57 (m, 1H); 6.54 (s, 2H); 7.87-7.92 (m, 3H) |
| Ex. 5-17-1 | Ethyl 2-(4-(2-(methoxy(2-methoxy-4-(trifluoromethoxy)phenyl)methyl)cyclopropyl)-2,6-dimethylphenoxy)-2-methylpropanoate | |
| | Ex. 4-13-1 and methyl iodide, Procotol C, Yield: 52%. | (250 MHz, CDCl$_3$): 0.72-0.81 (m, 1H); 0.92-1.01 (m, 1H); 1.36 (t, 3H, J = 7.1 Hz); 1.41-1.51 (m, 7H); 1.81-1.91 (m, 1H); 2.14 (s, 6H); 3.29 (s, 3H); 3.86 (s, 3H); 4.25-4.37 (m, 3H); 6.65 (s, 2H); 6.73-6.77 (m, 1H); 6.84-6.91 (m, 1H); 7.46 (d, 1H, J = 8.4 Hz) |
| Ex. 5-18-1 | Ethyl 2-(4-(2-((2-(hexyloxy)phenyl)(methoxy)methyl)cyclopropyl)-2,6-dimethylphenoxy)-2-methylpropanoate | |
| | Ex. 4-14-1 and methyl iodide, Procotol C, Yield: 65%, (de = 80%). | (250 MHz, CDCl$_3$): 0.68-0.78 (m, 1H); 0.87-1.01 (m, 4H); 1.24-1.51 (m, 16H); 1.72-1.84 (m, 3H); 2.14 (s, 6H); 3.26 (s, 3H); 3.88-4.01 (m, 2H); 4.25 (q, 2H, J = 7.1 Hz); 4.41 (d, 1H, J = 7.5 Hz); 6.63 (s, 2H); 6.85-6.88 (m, 1H); 6.97 (t, 1H, J = 7 Hz); 7.21 (dd, 1H, J = 7.7 Hz J = 1.4 Hz); 7.42-7.46 (m, 1H) |
| Ex. 5-19-1 | Ethyl 2-(2-bromo-4-(2-(methoxy(4-(trifluoromethoxy)phenyl)methyl)cyclopropyl)phenoxy)-2-methylpropanoate | |
| | Ex. 4-15-1 and methyl iodide, Procotol C, Yield: 85%. | (250 MHz, CDCl$_3$): 0.82-0.91 (m, 1H); 0.91-0.99 (m, 1H); 1.30 (t, J = 7.2 Hz); 1.37-1.43 (m, 1H); 1.62 (s, 6H); 1.97-2.05 (m, 1H); 3.30 (s, 3H); 3.81-3.84 (m, 1H); 4.27 (q, 2H, J = 7.2 Hz); 6.78 (d, 1H, J = 8.5 Hz); 6.89 (dd, 1H, J = 8.5 Hz J = 2.2 Hz); 7.21-7.28 (m, 3H); 7.39 (d, 2H, J = 8.7 Hz) |
| Ex. 5-20-1 | Ethyl 2-(2,6-difluoro-4-(2-(methoxy(4-(trifluoromethoxy)phenyl)methyl)cyclopropyl)phenoxy)-2-methylpropanoate | |
| | Ex. 4-16-1 and methyl iodide, Procotol C, Yield: 65%. | (250 MHz, CDCl$_3$): 0.79-0.91 (m, 1H); 0.96-1.04 (m, 1H); 1.29 (t, 3H, J = 7.2 Hz); 1.39-1.49 (m, 1H); 1.55 (s, 6H); 1.99-2.09 (m, 1H); 3.79-3.83 (m, 1H); 4.21 (q, 2H, J = 7.2 Hz); 6.55-6.65 (m, 2H); 7.22 (d, 2H, J = 8.6 Hz); 7.37 (d, 2H, J = 8.6 Hz) |
| Ex. 5-21-1 | Ethyl 2-(2-cyclopropyl-4-(2-(methoxy(4-(trifluoromethoxy)phenyl)methyl)cyclopropyl)phenoxy)-2-methylpropanoate | |
| | Ex. 5-19-1 and Cyclopropylboronic acid, Procotol F, Yield: 32%. | (250 MHz, CDCl$_3$): 0.58-0.68 (m, 2H); 0.77-0.99 (m, 4H); 1.25-1.43 (m, 4H); 1.58 (s, 6H); 1.92-2.02 (m, 1H); 2.16-2.28 (m, 1H); 3.31 (s, 3H); 3.8-3.84 (m, 1H); 4.28 (q, 2H, J = 7.1 Hz); 6.50 (d, 1H, J = 2.2 Hz); 6.65 (d, 1H, J = 8.4 Hz); 6.72 (dd, 1H, J = 8.4 Hz, 2.2 Hz); 7.24 (d, 2H, J = 8.6 Hz); 7.40 (d, 2H, J = 8.6 Hz) |

Example 6

Synthesis of the Compounds According to the Invention

The synthesis of the compounds according to the invention depicted in FIGS. 1 & 2 and summarized in Table 6-1 was realized using the Protocol D described in Example 1; otherwise, any specific changes in conditions of elution or reaction conditions are reported.

TABLE 6-1

| Cpd. | Starting materials, Protocol: specific conditions, purification, yield. | Appearance, $^1$H NMR (MHz, solvent) data, Mass (ES+/ES−), Melting Point. |
| --- | --- | --- |
| Cpd. 1-1 | Ex. 5-1-1, Protocol D<br>Yield: 53%. | White powder, (250 MHz, DMSO-d6): 0.70-0.78 (m, 1H); 0.83-0.91 (m, 1H); 1.22-1.27 (m, 1H); 1.27 (s, 6H); 1.90-1.97 (m, 1H); 2.11 (s, 6H); 3.16 (s. 3H); 3.74 (d, 1H, J = 8.0 Hz); 6.68 (s, 2H); 7.32 (d, 2H, J = 8.4 Hz); 7.55 (d, 2H, J = 8.4 Hz)<br>Mass (ES−): 445 (M($^{79}$Br)—H), MP = 133° C. |
| Cpd. 1-2 | Ex. 5-1-2, Protocol D<br>Yield: 61%. | Colorless oil, (400 MHz, DMSO-d6): 0.83-0.88 (m, 1H); 1.02-1.05 (m, 1H); 1.35-1.38 (m, 1H); 1.48 (m, 6H); 1.76-1.80 (m, 1H); 2.17 (s, 6H); 3.28 (s, 3H); 3.89 (d, 1H, J = 7.1 Hz); 6.55 (s, 2H); 7.22 (d, 2H, J = 8.2 Hz); 7.48 (d, 2H, J = 8.2 Hz)<br>Mass (ES−): 445 (M($^{79}$Br)—H). |
| Cpd. 2-1 | Ex. 5-2-1, Protocol D<br>Yield: 45%. | Amorphous solid, (400 MHz, DMSO-d6): 0.70-0.78 (m, 1H); 0.80-0.95 (m, 1H); 1.23-1.29 (m, 1H); 1.28 (s, 6H); 1.80-1.98 (m, 1H); 2.13 (s, 6H); 2.39 (s, 3H); 3.14 (s. 3H); 3.71 (d, 1H, J = 7.9 Hz); 6.68 (s, 2H); 7.17 (d, 2H, J = 8.1 Hz); 7.25 (d, 2H, J = 8.1 Hz)<br>Mass (ES−): 381 (M − H). |
| Cpd. 3-1 | Ex. 5-3-1, Protocol D<br>Yield: 43%,<br>Eluent: dichloromethane/methanol: 99/1 | Amorphous solid, (250 MHz, DMSO-d6): 0.69-0.77 (m, 1H); 0.81-0.95 (m, 1H); 1.23-1.29 (m, 1H); 1.28 (s, 6H); 1.88-1.96 (m, 1H); 2.11 (s, 6H); 2.47 (s, 3H); 3.14 (s, 3H); 3.71 (d, 1H, J = 7.9 Hz); 6.68 (s, 2H); 7.24 (d, 2H, J = 8.1 Hz); 7.30 (d, 2H, J = 8.1 Hz); 12.79 (br s, 1H)<br>Masse (ES−): 413.1 (M − H). |
| Cpd. 3-2 | Ex. 5-3-2, Protocol D<br>Yield: 30%. | Colorless oil, (4000 MHz, DMSO-d6): 0.83-0.90 (m, 1H); 1.00-1.07 (m, 1H); 1.28-1.32 (m, 7H); 1.73-1.81 (m, 1H); 2.07 (s, 6H); 2.44 (s, 3H); 3.15 (s, 3H); 3.86 (d, 1H, J = 7.0 Hz); 6.58 (s, 2H); 7.22 (d, 2H, J = 8.2 Hz); 7.35 (d, 2H, J = 8.2 Hz); 12.76 (br s, 1H). |
| Cpd. 4-1 | Ex. 5-4-1, Protocol D<br>Yield: 90%. | White powder, (250 MHz, DMSO-d6): 0.73-0.80 (m, 1H); 0.89-0.97 (m, 1H); 1.24-1.29 (m, 1H); 1.32 (s, 6H); 1.95-2.02 (m, 1H); 2.10 (s, 6H); 3.20 (s, 3H); 3.87 (d, 1H, J = 8.2 Hz); 6.69 (s, 2H); 7.60 (d, 2H, J = 8.1 Hz); 7.74 (d, 2H, J = 8.1 Hz); 12.78 (s, 1H)<br>Mass (ES−): 435 (M − H); MP = 146-150° C. |
| Cpd. 4-2 | Ex. 5-4-2, Protocol D<br>Yield: 70%. | Colorless oil, (250 MHz, CDCl$_3$): 0.95-1.02 (m, 1H); 1.10-1.24 (m, 1H); 1.36-1.45 (m, 1H); 1.50 (s, 6H); 1.77-1.94 (m, 1H); 2.18 (s, 6H); 3.33 (s, 3H); 4.04 (d, 1H, J = 6.5 Hz); 6.60 (s, 2H); 7.51 (d, 2H, J = 8.0 Hz); 7.66 (d, 2H, J = 8.0 Hz)<br>Mass (ES−): 435 (M − H). |

TABLE 6-1-continued

| Cpd. | Starting materials, Protocol: specific conditions, purification, yield. | Appearance, $^1$H NMR (MHz, solvent) data, Mass (ES+/ES−), Melting Point. |
|---|---|---|
| Cpd. 5-1 | Ex. 5-5-1, Protocol D, Yield: 77%. | Amorphous solid, (250 MHz, CDCl$_3$): 0.82-0.90 (m, 5H); 1.37-1.44 (m, 3H); 1.50 (s, 6H); 1.52-1.58 (m, 2H); 1.91-1.95 (m, 1H); 2.19 (s, 6H); 3.36-3.40 (m, 2H); 3.94 (d, 1H, J = 7.4 Hz); 6.69 (s, 2H); 7.21 (d, 2H, J = 8.3 Hz); 7.42 (d, 2H, J = 8.3 Hz)<br>Mass (ES−): 493.2 (M − H). |
| Cpd. 5-2 | Ex. 5-5-2, Protocol D, Yield: 65%. | Colorless oil, (250 MHz, CDCl$_3$): 0.89-1.09 (m, 4H); 1.16-1.29 (m, 1H); 1.32-1.45 (m, 3H); 1.48 (s, 6H); 1.54-1.65 (m, 2H); 1.74-1.95 (m, 1H); 2.17 (s, 6H); 3.38 (t, 2H, J = 6.4 Hz); 4.06 (d, 1H, J = 6.4 Hz); 6.60 (s, 2H); 7.22 (d, 2H, J = 8.1 Hz); 7.41 (d, 2H, J = 8.1 Hz)<br>Mass (ES−): 493.2 (M − H). |
| Cpd. 6-1 | Ex. 5-6-1, Protocol D, Yield: 59%. | Colorless oil, (250 MHz, CDCl$_3$): 0.82-0.94 (m, 4H); 1.19-1.23 (m, 3H); 1.33-1.37 (m, 2H); 1.50 (s, 6H); 1.45-1.49 (m, 2H); 1.63-1.69 (m, 5H); 1.91-1.95 (m, 1H); 2.19 (s, 6H); 3.41 (t, 2H, J = 6.3 Hz); 3.89 (d, 1H, J = 7.4 Hz); 6.69 (s, 2H); 7.21 (d, 2H, J = 8.4 Hz); 7.42 (d, 2H, J = 8.4 Hz)<br>Mass (ES−): 547.3 (M − H). |
| Cpd. 6-2 | Ex. 5-6-2, Protocol D, Yield: 45%. | Colorless oil, (250 MHz, CDCl$_3$): 0.82-0.94 (m, 4H); 1.10-1.60 (m, 13H); 1.63-1.87 (m, 6H); 2.16 (s, 6H); 3.40 (t, 2H, J = 6.6 Hz); 4.04 (d, 1H, J = 6.5 Hz); 6.59 (s, 2H); 7.21 (d, 2H, J = 8.4 Hz); 7.40 (d, 2H, J = 8.4 Hz)<br>Mass (ES−): 547.3 (M − H). |
| Cpd. 7-1 | Ex. 5-7-1, Protocol D, Yield: 50%, Eluent: dichloromethane/methanol: 99/1 | Colorless oil, (DMSO-d6): 0.71-0.79 (m, 1H); 0.86-0.93 (m, 1H); 1.23-1.31 (m, 1H); 1.46 (s, 6H); 1.80-1.87 (m, 1H); 2.10 (s, 3H); 3.18 (s, 3H); 3.84-3.87 (m, 1H); 6.57-6.61 (m, 1H); 6.76-6.79 (m, 2H); 7.32-7.36 (m, 2H); 7.45-7.53 (m, 2H); 12.94 (br s, 1H)<br>Mass (ES−): 437 (M − H). |
| Cpd. 7-2 | Ex. 5-7-2, Protocol D, Yield: 40%, Eluent: dichloromethane/methanol: 99/1 | Amorphous solid, (250 MHz, DMSO-d6): 0.87-0.94 (m, 1H); 1.03-1.10 (m, 1H); 1.23-1.31 (m, 1H); 1.43 (s, 6H); 1.80-1.87 (m, 1H); 2.04 (s, 3H); 3.19 (s, 3H); 3.65-3.68 (m, 1H); 6.50-6.53 (m, 1H); 6.65-6.73 (m, 2H); 7.32-7.36 (m, 2H); 7.47-7.50 (m, 2H); 12.91 (br s, 1H)<br>Mass (ES−): 437.1 (M − H). |
| Cpd. 8-1 | Ex. 5-8-1, Protocol D, Yield: 50%, Eluent: dichloromethane/methanol: 99/1 | Colorless oil, (250 MHz, DMSO-d6): 0.68-0.76 (m, 1H); 0.78-0.86 (m, 1H); 0.97 (t, 3H, J = 7.3 Hz); 1.30-1.36 (m, 1H); 1.33 (s, 6H); 1.64-1.78 (m, 2H); 1.70-1.94 (m, 1H); 2.12 (s, 6H); 3.12 (s, 3H); 3.67 (d, 1H, J = 7.8 Hz); 3.90 (t, 2H, J = 6.5 Hz); 6.69 (s, 2H); 6.89 (d, 2H, J = 8.6 Hz); 7.25 (d, 2H, J = 8.6 Hz); 12.79 (br s, 1H)<br>Mass (ES−): 426.1 (M − H). |
| Cpd. 8-2 | Ex. 5-8-2, Protocol D, Yield: 40%, Eluent: dichloromethane/methanol: 99/1 | Colorless oil, (250 MHz, DMSO-d6): 0.82-0.89 (m, 1H); 0.93-1.07 (m, 4H); 1.28-1.39 (m, 7H); 1.63-1.77 (m, 3H); 2.06 (s, 6H); 3.12 (s, 3H); 3.82 (d, 1H, J = 7.0 Hz); 3.89 (t, 2H, J = 6.5 Hz); 6.58 (s, 2H); 6.68 (d, 2H, J = 8.6 Hz); 7.24 (d, 2H, J = 8.6 Hz); 12.76 (br s, 1H)<br>Masse (ES−): 426.1 (M − H). |
| Cpd. 9-1 | Ex. 5-9-1, Protocol D, Yield: 15%. | White solid, (250 MHz, DMSO-d6): 0.74-0.81 (m, 1H); 0.89-0.97 (m, 1H); 1.23-1.29 (m, 1H); 1.32 (s, 6H); 1.94-2.02 (m, 1H); 2.10 (s, 6H); 3.19 (s. 3H); 3.83 (d, 1H, J = 8.1 Hz); 6.69 (s, 2H); 7.54 (d, 2H, J = 8.2 Hz); 7.72 (d, 2H, J = 8.2 Hz); 12.77 (br s, 1H)<br>Masse (ES−): 467.1 (M − H), MP = 135-137° C. |

TABLE 6-1-continued

| Cpd. | Starting materials, Protocol: specific conditions, purification, yield. | Appearance, $^1$H NMR (MHz, solvent) data, Mass (ES+/ES−), Melting Point. |
|---|---|---|
| Cpd. 10-1 | Ex. 5-10-1, Protocol D, Yield: 70%. | Colorless oil, (250 MHz, CDCl$_3$): 0.82-0.96 (m, 2H); 1.23 (t, 3H, J = 7.1 Hz); 1.38-1.43 (m, 1H); 1.51 (s, 6H); 1.88-1.93 (m, 1H); 2.21 (s, 6H); 3.41-3.48 (m, 2H); 3.96 (d, 1H, J = 7.4 Hz); 6.70 (s, 2H); 7.23 (d, 2H, J = 8.1 Hz); 7.42 (d, 2H, J = 8.1 Hz)<br>Masse (ES−): 465.0 (M − H). |
| Cpd. 10-2 | Ex. 5-10-2, Protocol D, Yield: 65%. | White solid, (400 MHz, CDCl$_3$): 0.86-0.96 (m, 1H); 1.15-1.30 (m, 4H); 1.34-1.42 (m, 1H); 1.48 (s, 6H); 1.81-1.91 (m, 1H); 2.16 (s, 6H); 3.42-3.48 (m, 2H); 4.02 (d, 1H, J = 7.1 Hz); 6.57 (s, 2H); 7.21 (d, 2H, J = 8.1 Hz); 7.42 (d, 2H, J = 8.1 Hz); 9.11 (br s, 1H)<br>Mass (ES−): 465.0 (M − H). |
| Cpd. 11-1 | Ex. 5-11-1, Protocol D, Yield: 19%. | Colorless oil, (250 MHz, CDCl$_3$): 0.82-0.94 (m, 2H); 1.47 (s, 6H); 1.45-1.49 (m, 1H); 1.91-1.95 (m, 1H); 2.20 (s, 6H); 4.00 (d, 1H, J = 7.4 Hz); 4.39 (d, 1H, J = 12.1 Hz); 4.58 (d, 1H, J = 12.1 Hz); 6.69 (s, 2H); 7.11-7.56 (m, 9H)<br>Mass (ES−): 528.1 (M − H). |
| Cpd. 11-2 | Ex. 5-11-2, Protocol D, Yield: 75%. | Colorless oil, (250 MHz, CDCl$_3$): 0.96-1.04 (m, 1H); 1.17-1.22 (m, 1H); 1.41-1.47 (m, 1H); 1.50 (s, 6H); 1.82-1.92 (m, 1H); 2.20 (s, 6H); 4.17 (d, 1H, J = 7.1 Hz); 4.39 (d, 1H, J = 12.1 Hz); 4.58 (d, 1H, J = 12.1 Hz); 6.59 (s, 2H); 7.24-7.47 (m, 9H)<br>Mass (ES−): 528.1 (M − H). |
| Cpd. 12-1 | Ex. 5-12-1, Protocol D, Yield: 73%. | Colorless oil, (250 MHz, DMSO-d6): 0.79-0.86 (m, 1H); 0.95-1.05 (m, 1H); 1.35-1.43 (m, 1H); 1.49 (s, 6H); 1.93-1.99 (m, 1H); 2.18 (s, 6H); 3.31 (s, 3H); 4.23 (d, 1H, J = 7.7 Hz); 6.69 (s, 2H); 7.30-7.38 (m, 1H); 7.44-7.5 (m, 1H); 7.6-7.66 (m, 1H); 9.28 (s, 1H).<br>Mass (ES−): 453 (M − H). |
| Cpd. 12-2 | Ex. 5-12-2, Protocol D, Yield: 82%. | Colorless oil, (400 MHz, CDCl$_3$): 0.92-1.00 (m, 1H); 1.09-1.17 (m, 1H); 1.35-1.43 (m, 1H); 1.47 (s, 6H); 1.87-1.95 (m, 1H); 2.15 (s, 6H); 3.31 (s, 3H); 4.36 (d, 1H, J = 6.8 Hz); 6.58 (s, 2H); 7.3-7.38 (m, 1H); 7.42-7.48 (m, 1H); 7.58-7.64 (m, 1H)<br>Mass (ES−): 453 (M − H). |
| Cpd. 13-1 | Ex. 5-13-1, Protocol D, Yield: 83%. | Colorless oil, (250 MHz, DMSO-d6): 0.76-0.84 (m, 1H); 0.96-1.04 (m, 1H); 1.31-1.44 (m, 1H); 1.48 (s, 6H); 1.92-2.00 (m, 1H); 2.17 (s, 6H); 3.26 (s, 3H); 4.26 (d, 1H, J = 7.5 Hz); 6.68 (s, 2H); 7.26-7.30 (m, 1H); 7.32-7.36 (m, 2H); 7.55-7.64 (m, 1H)<br>Mass (ES−): 451 (M − H). |
| Cpd. 13-2 | Ex. 5-13-2, Protocol D, Yield: 76%. | Colorless oil, (250 MHz, CDCl$_3$): 0.90-0.97 (m, 1H); 1.09-1.16 (m, 1H); 1.34-1.42 (m, 1H); 1.46 (s, 6H); 1.86-1.93 (m, 1H); 2.14 (s, 6H); 3.25 (s, 3H); 4.36 (d, 1H, J = 6.7 Hz); 6.57 (s, 2H); 7.28-7.34 (m, 3H); 7.55-7.57 (m, 1H)<br>Mass (ES−): 451 (M − H). |
| Cpd. 14-1 | Ex. 5-14-1, Protocol D, Yield: 28%, Eluent: dichloromethane/methanol: 95/5 | Colorless oil, (300 MHz, DMSO-d6): 0.72-0.80 (m, 1H); 0.87-0.95 (m, 1H); 1.20-1.35 (m, 7H); 1.93-2.02 (m, 1H); 2.10 (s, 6H); 3.17 (s, 3H); 3.79 (d, 1H, J = 8.2 Hz); 6.68 (s, 2H); 7.35 (d, 2H, J = 8.5 Hz); 7.49 (d, 2H, J = 8.5 Hz);<br>Mass (ES+): 475 (M + Na). |

TABLE 6-1-continued

| Cpd. | Starting materials, Protocol: specific conditions, purification, yield. | Appearance, $^1$H NMR (MHz, solvent) data, Mass (ES+/ES−), Melting Point. |
|---|---|---|
| Cpd. 14-2 | Ex. 5-14-2, Protocol D, Yield: 61%, Eluent: dichloromethane/methanol: 95/5 | White powder, (300 MHz, DMSO-d6): 0.85-0.92 (m, 1H); 1.02-1.11 (m, 1H); 1.20-1.35 (m, 7H); 1.77-1.86 (m, 1H); 2.05 (s, 6H); 3.18 (s, 3H); 3.98 (d, 1H, J = 7.0 Hz); 6.57 (s, 2H); 7.33 (d, 2H, J = 8.5 Hz); 7.48 (d, 2H, J = 8.5 Hz) Mass (ES+): 475 (M + Na), MP = 190-194° C. |
| Cpd. 14-1-1 | Ex. 5-14-1-1, Protocol D, Yield: 45% Eluent: dichloromethane/methanol: 96/4 to 95/5. | White powder, (300 MHz, DMSO-d6): 0.75 (m, 1H, J = 4.9 Hz); 0.89 (m, 1H, J = 4.9 Hz); 1.20-1.35 (m, 7H); 1.92 (m, 1H, J = 5.2 Hz); 2.10 (s, 6H); 3.17 (s, 3H); 3.79 (d, 1H, J = 8.2 Hz); 6.68 (s, 2H); 7.35 (d, 2H, J = 8.5 Hz); 7.49 (d, 2H, J = 8.5 Hz); 12.79 (s, 1H) Mass (ES+): 453.2 (M + H), MP = 155-156° C. Rt = 15.33 min. ChiralpaK AD-H 250 × 4.6 mm (heptane/IPA 97/3 0.1% TFA). ee = 100%. |
| Cpd. 14-1-2 | Ex. 5-14-1-2, Protocol D, Yield: 77% Trituration in diisopropyl ether and filtration | White powder, (300 MHz, DMSO-d6): 0.75 (m, 1H, J = 4.9 Hz); 0.89 (m, 1H, J = 4.9 Hz); 1.20-1.35 (m, 7H); 1.92 (m, 1H, J = 5.2 Hz); 2.10 (s, 6H); 3.17 (s, 3H); 3.79 (d, 1H, J = 8.2 Hz); 6.68 (s, 2H); 7.35 (d, 2H, J = 8.5 Hz); 7.49 (d, 2H, J = 8.5 Hz); 12.77 (s, 1H) Mass (ES+): 453.2 (M + H) MP = 155-156° C. Rt = 18.43 min. ChiralpaK AD-H 250 × 4.6 mm (heptane/IPA 97/3 0.1% TFA). ee = 99.6%. |
| Cpd. 14-2-1 | Ex. 5-14-2-1, Protocol D, Yield: 59% Eluent: dichloromethane/methanol: 95/5. | Colorless oil, (300 MHz, CDCl3): 0.87-1.08 (m, 1H); 1.08-1.29 (m, 1H); 1.34-1.44 (m, 1H); 1.47 (s, 6H); 1.70-1.89 (m, 1H); 2.15 (s, 6H); 3.32 (s, 3H); 3.98 (d, 1H, J = 7.6 Hz); 6.59 (s, 2H); 7.26 (d, 2H, J = 8.1 Hz); 7.41 (d, 2H, J = 8.1 Hz) Mass (ES−): 451 (M − H) Rt = 14.04 min, ChiralpaK AD-H 250 × 4.6 mm (heptane/IPA 97/3 0.1% TFA) ee = 95.17%. |
| Cpd. 14-2-2 | Ex. 5-14-2-2, Protocol D, Yield: 85% Eluent: dichloromethane/methanol: 95/5. | Colorless oil, (300 MHz, CDCl3): 0.87-1.08 (m, 1H); 1.08-1.29 (m, 1H); 1.34-1.44 (m, 1H); 1.47 (s, 6H); 1.70-1.89 (m, 1H); 2.15 (s, 6H); 3.32 (s, 3H); 3.98 (d, 1H, J = 7.6 Hz); 6.59 (s, 2H); 7.26 (d, 2H, J = 8.1 Hz); 7.41 (d, 2H, J = 8.1 Hz) Mass (ES−): 451 (M − H) Rt = 19.15 min, ChiralpaK AD-H × 4.6 mm (heptane/IPA 97/3 0.1% TFA) ee = 97.55%. |
| Cpd. 15-1 | Ex. 5-15-1, Protocol D, Yield: 34%, Eluent: dichloromethane/methanol: 95/5. | Colorless oil, (300 MHz, CDCl3): 0.64-0.76 (m, 1H); 0.77-0.87 (m, 1H); 1.06 (d, 6H, J = 6.9 Hz); 1.21-1.48 (m, 7H); 1.85-1.98 (m, 1H); 3.12-3.31 (m, 4H); 3.78 (d, 1H, J = 7.3 Hz); 6.49-6.59 (m, 1H); 6.61-6.76 (m, 1H); 6.78-6.87 (m, 1H); 7.20 (d, 2H, J = 8.2 Hz); 7.35 (d, 2H, J = 8.2 Hz) Mass (ES−): 465 (M − H). |
| Cpd. 15-2 | Ex. 5-15-2, Protocol D, Yield: 63%, Eluent: dichloromethane/methanol: 95/5. | Colorless oil, (300 MHz, CDCl3): 0.82-1.03 (m, 8H); 1.04-1.37 (m, 7H); 1.72-1.83 (m, 1H); 3.06-3.18 (m, 1H); 3.27 (s, 3H); 3.83-3.87 (m, 1H); 6.40 (d, 1H, J = 7.4 Hz); 6.52-6.71 (m, 2H); 7.17 (d, 2H, J = 8.4 Hz); 7.35 (d, 2H, J = 8.4 Hz) Mass (ES+): 465 (M − H). |
| Cpd. 16-1 | Ex. 5-16-1, Protocol D, Yield: 61%, Eluent: dichloromethane/methanol: 95/5. | Colorless oil, (300 MHz, CDCl3): 0.79-0.84 (m, 1H); 1.01-1.08 (m, 1H); 1.34-1.44 (m, 1H); 1.48 (s, 6H); 2.00-2.09 (m, 1H); 2.17 (s, 6H); 3.22 (s, 3H); 4.40 (d, 1H, J = 5.9 Hz); 6.66 (s, 2H); 7.87 (d, 1H, J = 8.2 Hz); 7.92 (s, 1H); 7.95 (d, 1H, J = 8.2 Hz) Mass (ES−): 503.1 (M − H). |

TABLE 6-1-continued

| Cpd. | Starting materials, Protocol: specific conditions, purification, yield. | Appearance, $^1$H NMR (MHz, solvent) data, Mass (ES+/ES−), Melting Point. |
|---|---|---|
| Cpd. 16-2 | Ex. 5-16-2, Protocol D, Yield: 62%, Eluent: dichloromethane/methanol: 95/5. | White solid, (300 MHz, CDCl3): 0.84-0.91 (m, 1H); 1.15-1.30 (m, 1H); 1.30-1.42 (m, 1H); 1.45 (s, 6H); 1.92-2.04 (m, 1H); 2.13 (s, 6H); 3.19 (s, 3H); 4.54 (d, 1H, J = 4.8 Hz); 6.56 (s, 2H); 7.84-7.92 (m, 3H) Mass (ES−): 503.1 (M − H), MP = 127-130° C. |
| Cpd. 17-1 | Ex. 5-17-1, Protocol D, Yield: 45%, Eluent: dichloromethane/methanol: 95/5. | Colorless oil, (300 MHz, CDCl3): 0.72-0.82 (m, 1H); 0.94-1.03 (m, 1H); 1.37-1.49 (m, 1H); 1.48 (s, 6H); 1.81-1.93 (m, 1H); 2.20 (s, 6H); 3.30 (s, 3H); 3.87 (s, 3H); 4.34 (d, 1H, J = 7.5 Hz); 6.67 (s, 2H); 6.73-6.81 (m, 1H); 6.88-6.92 (m, 1H); 7.45 (d, 1H, J = 8.7 Hz) Mass (ES−): 481 (M − H). |
| Cpd. 18-1 | Ex. 5-18-1, Protocol D, Yield: 59%, (de = 80%). Eluent: dichloromethane/methanol: 95/5. | Colorless oil, (300 MHz, CDCl3): 0.67-0.80 (m, 1H); 0.84-0.93 (m, 3H); 0.94-1.04 (m, 1H); 1.23-1.39 (m, 5H); 1.42-1.52 (m, 4H); 1.47 (s, 6H); 1.54-1.76 (m, 3H); 1.47 (s, 6H); 3.28 (m, 3H); 3.83 (d, 1H, J = 7.5 Hz); 6.67 (s, 2H); 6.87 (d, 1H, J = 8.3 Hz J = 1.1 Hz); 6.98 (m, 1H); 7.16-7.30 (m, 1H); 7.44 (dd, 1H, J = 7.6 Hz J = 1.8 Hz) Mass (ES−): 467 (M − H). |
| Cpd. 19-1 | Ex. 5-19-1, Protocol D, Yield: 95%, Eluent: dichloromethane/methanol: 95/5. | Colorless oil, (300 MHz, CDCl3): 0.81-0.91 (m, 1H); 0.94-1.04 (m, 1H); 1.38-1.48 (m, 1H); 1.63 (s, 6H); 1.98-2.12 (m, 1H); 3.20 (s, 3H); 3.83 (d, 1H, J = 7.4 Hz); 6.92-6.98 (m, 2H); 7.22-7.30 (m, 3H); 7.39 (d, 2H, J = 8.6 Hz) Mass (ES−): 501/503 (M − H). |
| Cpd. 20-1 | Ex. 5-20-1, Protocol D, Yield: 53%, Eluent: dichloromethane/methanol: 95/5. | Colorless oil, (300 MHz, CDCl3): 0.83-0.94 (m, 1H); 0.99-1.11 (m, 1H); 1.38-1.48 (m, 1H); 1.57 (s, 6H); 1.54-1.76 (m, 1H); 3.28 (s, 3H); 3.83 (d, 1H, J = 7.3 Hz); 6.65 (d, 2H, J = 9.0 Hz); 7.25 (d, 2H, J = 8.7 Hz); 7.39 (d, 2H, J = 8.7 Hz) Mass (ES−): 459 (M − H). |
| Cpd. 21-1 | Ex. 5-21-1, Protocol D, Yield: 78%, Eluent: dichloromethane/methanol: 95/5. | Colorless oil, (300 MHz, DMSO): 0.58-0.64 (m, 2H); 0.72-0.79 (m, 1H); 0.83-0.93 (m, 3H); 1.22-1.29 (m, 1H); 1.46 (s, 6H); 1.95-2.03 (m, 1H); 2.09-2.16 (m, 1H); 3.18 (s, 3H); 3.8 (d, 1H, J = 7.8 Hz); 6.42-6.46 (m, 1H); 6.65 (d, 1H, J = 8.5 Hz); 6.69-6.76 (m, 1H); 7.37 (d, 2H, J = 8.5 Hz); 7.5 (d, 2H, J = 8.5 Hz) Mass (ES+): 465 (M + H). |

Example 7

Biological Results with Compounds of the Invention

Materials and Methods
Diabetes Model (db/db Mice)

The male db/db mice (8 to 9 week-old) were purchased from CERJ JANVIER (Le Genest Saint Isle, France). Animal care and handling was performed according to the Declaration of Helsinki and was approved by the local ethics committees. The animals were kept under a 12 hour light/dark standard light cycle and had free access to water and food. Animals were fed standard rodent chow diet (A03 SAFE, Augy, France). Mice were randomly assigned into different treatment groups, weighed and dosed by oral gavage (10 ml/kg body weight) once daily in the morning, either with the vehicle or with the compound. The vehicle used was 0.1% Tween 80 (Polyoxyethylenesorbitan monooleate) and 1% carboxymethylcellulose in 98.9% distilled water. The entire treatment protocol took 37 days. Non-fasting glycemia was measured at 8 A.M. with the Smart Check blood glucose monitoring system, in mice that have had unrestricted access to food and water throughout the night. The blood concentration of the glycosylated hemoglobin A1c was determined using the Randox kit for Daytona automate (Randox, cat# HA 3830) according to the manufacturer's recommendations. The HbA1c result was calculated as a percentage of the total hemoglobin concentration.

Gal4-PPAR Assays

Monkey kidney COS-7 cells were maintained in standard culture conditions (Dulbecco's modified Eagle's minimal medium: DMEM) supplemented with 10% fetal calf serum, 1% sodium pyruvate, 1% essential amino acids and 1% antibiotics at 37° C. in a humidified atmosphere of 5% $CO_2$ and 95% air. The medium was changed every 2 days. All tested compounds were dissolved in DMSO. Cells were transfected using 2 µl JetPEI™ (Polyplus transfection)/µg of DNA. Briefly, 40 µg of DNA was transfected in a 225 $cm^2$ culture flask of adherent COS-7 cells (respecting the 1/50 ratio between the Gal4(RE)_TkpGL3 plasmid and the plasmid coding the nuclear receptor of interest (pGal4-hPPARalpha, pGal4-hPPARgamma, pGal4-hPPARdelta, pGal4-mPPA- Ralpha, pGal4-mPPARgamma and pGal4-mPPARdelta) or of the pGal4phi plasmid (negative control). Cells were enzymatically detached and seeded in 384 well plates at the density of 20,000 cells/well and then incubated for 4 hours at 37° C. The activation was automatically performed, by using the Genesis Freedom 200™ (Tecan), in fresh medium supplemented with 2% of synthetic serum, free of lipids (Ultroser™, Biosepra) supplemented with the tested compounds (compound of interest or reference molecules) or vehicle (DMSO 0.1%). The luciferase activity was measured with the Steady-Glo Luciferase Assay System (Promega, Madison, Wis.). All transactivation experiments were performed at least 2 times. Activation curves were realized using SigmaPlot® (version 7.0 from SPSS Inc.) software and took into account all the experimental points. SimgaPlot® was also used to fit the standard curves and then determine the specific EC50 values, maximum effect versus reference molecules and Hill slope. The $E_{max}$ effect of each new ligand is represented as the ratio of the maximal induction (plateau) obtained with the new ligand and the induction obtained with the corresponding reference compound. The reference compounds for PPARalpha, PPARgamma and PPARdelta were fenofibrate (100 μM), rosiglitazone (10 μM) and GW501516 (1 μM).

Compound Pharmacokinetics Study in Mice

The compound was administered to six male swiss mice (five weeks old) by the PO route and six male mice by the iv route (caudal vein). For the iv route, the compound was dissolved in DMSO to obtain a 2 mg/mL solution for a dose of 1 mg/kg. For the PO route (10 mg/kg), the compound was dissolved in a solution of 0.5% Methyl cellulose (ref sigma M0262) and 0.3% Polysorbate 80 (Tween 80—ref sigma P8074). During the iv administration and blood sampling animals were anesthetized with Isofluorane® (from Belamont) using an anaesthetic system (Minerve). At the precise time-point, blood samplings were done at the retro-orbital sinus, with a capillary tube. The blood volume collected per each time-point was 0.2-0.3 ml. Blood samples were collected into tubes containing both lithium and heparin and then centrifuged at 2500 rpm at 4° C. Plasma was removed and transferred into polypropylene tubes. Individual plasma aliquots were frozen at −20° C. (±5° C.) and stored until analysis.

After blood sampling, the animals were perfused with 7 ml cold saline solution directly into the heart to extract the maximum of blood from the brain vasculature. Animals were then beheaded and the brain tissue collected and frozen at −20° C. (±5° C.) and stored until analysis. Prior to the sample analysis, the suitability of the analytical method to detect the compounds to be evaluated was performed as described below. The molecular and daughter ions were selected for each molecule by direct infusion into the MS-MS system. For those plasma samples which are mixed prior to analysis, precaution was taken to avoid mixing common moieties both with regards to the parent compounds as well as potential metabolites. According to the expected sensitivity, 8 point calibration standards (1, 5, 10, 50, 100, 500, 1000 and 5000 ng/mL) were run using standard conditions which consist to LC/MS/MS system with C18 column after precipitation of the plasma proteins with acetonitrile before the start of the analytical test. Calibration standards were performed in each matrix (plasma and brain). Prior to analysis, 100 μL of each plasma sample was mixed with 300 μL acetonitrile. Following protein precipitation, samples were vortex mixed for 30 seconds, centrifuged 5 min at 15000 tr/min and the supernatant was removed. Analyses were performed using LC/MS/MS determination according to previous analytical test results. Brains were homogenized with a potter using water (1/1, w/w). 100 μl of the homogenate was mixed with 100 μl of acetonitrile. The mixture was mixed (Vortex) for 30 seconds, then centrifuged during 5 min at 15000 tr/min. Brain homogenate supernatants were directly measured by LC/MS/MS after centrifugation. LC-MS/MS system was used with a C18 Kromasil column and API4000® from Applied Biosystem or Quattro® from Waters as mass spectrometers.

Alzheimer's Disease Model (APPPS1 Mice)

Mice for that study were produced by in vitro fertilization (Charles River, France). Heterozygous double transgenic male mice expressing a chimeric mouse/human amyloid precursor protein (APP) with the Swedish mutation (K595N/M596L) and a mutant human presenilin 1 (exon 9 deletion) under the control of prion promoter were used. The animals were on a C57BL/6J background. Animal care and handling was performed according to the Declaration of Helsinki and was approved by the local ethics committees. Female mice (n=11-12 per group) of 4 months of age were used for experiments. Mice were fed ad libitum a standard chow pellets (Sniff, ref E15000-04), supplemented with the compound. The dosage of drug was computed to be 1 or 10 mg/kg/day of the compound as based on an average daily food consumption of 5 g of chow per mouse. Animals were treated for 8 weeks, starting at age of 17 weeks, prior to MWM assay. During the experimental treatment, animals were housed 4 per cage. In all instances, animals lived under standard conditions of 22° C. with a 12 h light-dark cycle and with free access to food and water. Spatial memory was evaluated in control and in treated APPPS1 mice by the Morris-Water-Maze test as described by Terwel et al., (J Neurosci. 2011 May 11; 31(19): 7049-59). At the time of sacrifice, animals received a short inhalation anaesthesia using isoflurane. Animals were transcardially perfused with heparinized sodium chloride (0.9%). The brains were removed and brain regions were dissected from one hemisphere. Hemispheres were homogenized in ice cold PBS, 1 mM EDTA, 1 mM EGTA, 3 μl/ml protease inhibitor mix (Sigma). Homogenates were extracted in radio immunoprecipitation assay (RIPA) buffer (25 mM Tris-HCl pH 7.5, 150 mM NaCl, 1% NP40, 0.5% NaDOC, 0.1% SDS), centrifuged at 100,000×g for 30 min. The supernatant was considered to contain the soluble amyloid-beta fraction. The remaining pellet was subsequently solubilized in 2% SDS, 25 mM Tris-HCl, pH 7.5 and centrifuged at 100,000×g for 30 min. The supernatant was considered to contain the SDS-soluble amyloid-beta fraction. The remaining pellet was subsequently solubilized in 70% formic acid in water and dried under vacuum centrifugation (speed-vac). The pellet was resuspended in 200 mM Tris pH 7.5, and was considered to contain the insoluble amyloid-beta fraction. The extracted protein fractions were measured using the 4G8 beta-amyloid triplex ultra sensitive ELISA (Mesocale) according to the manufactures protocol. SDS-soluble fractions were diluted 1:50 in 1% blocker A solution containing 0.5% Tx-100.

Results & Conclusions

Figure 4:
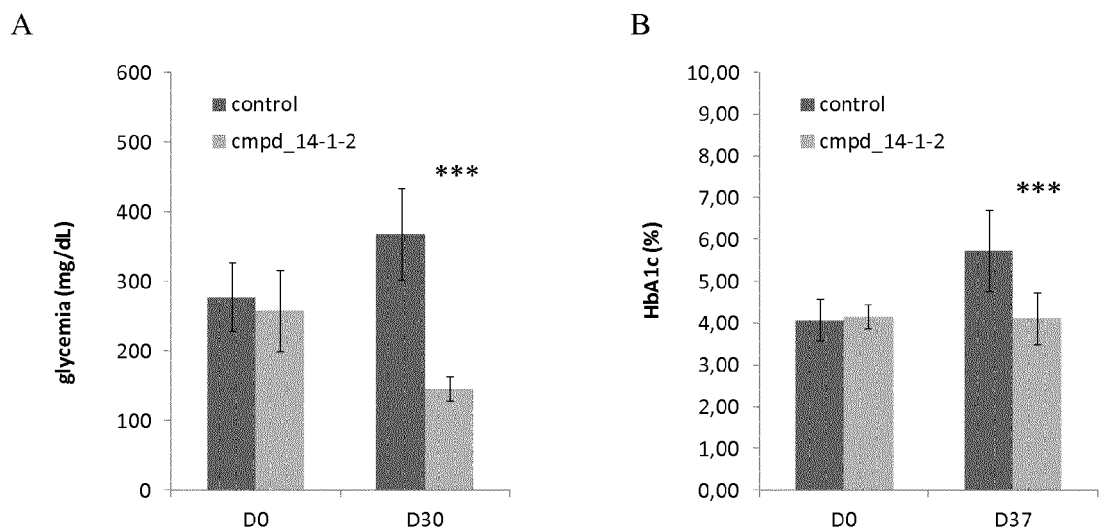
FIG. 4—Effect of compound 14-1-2 on glucose homeostasis parameters in db/db mice Diabetic db/db mice were treated with Cpd_14-1-2 (3 mg per kg per day) by gavage, as described in materials and methods. Non-fasting glycemia (A) and glycated hemoglobin (HbA1c) (B) were measured by day 30 (D30) and by day 37 (D37), respectively.

Diabetic db/db mice were treated with CPD_14-1-2 (3 mg per kg per day) by gavage, as described in materials and methods. Non-fasting glycemia (A) and glycated hemoglobin (HbA1c) (B) were measured by day 30 (D30) and by day 37 (D37), respectively. Results are shown in FIG. 4.

Non-fasting glycemia has increased by 33% (from 277 mg/dL to 368 mg/dL) in untreated, diabetic mice (control) during the study period. In contrary, a decrease of 48% (from 258 mg/dL to 146 mg/dL) was observed during that same period of time in mice treated with the CPD 14-1-2. At day 30, the non-fasting glycemia was 60% lower (146 mg/dL as compared to 368 mg/dL; t-test p-value <0.0001) in mice treated with CPD_14-1-2, as compared to untreated controls. The glycated hemoglobin content has increased by 41% (from 4.08% to 5.74%) in the diabetic, untreated mice during the study period. In contrary, no significant change in HbA1c was observed during that same period of time in mice treated with the CPD_14-1-2 (4.12% as compared to 4.16%). At day 37, the HbA1c was 28% lower (4.12% as compared to 5.74%; t-test p-value <0.01) in mice treated with CPD_14-1-2, as compared to the diabetic controls.

TABLE 7

| | Gal4-hPPARα(LBD) | | Gal4-hPPARγ(LBD) | | Gal4-hPPARδ(LBD) | |
|---|---|---|---|---|---|---|
| | $EC_{50}$ (µM) | TOP (% ref) | $EC_{50}$ (µM) | TOP (% ref) | $EC_{50}$ (µM) | TOP (% ref) |
| cpd 1-1 | 0.239 | 44 | 0.044 | 68 | 0.04 | 84 |
| cpd 1-2 | 0.186 | 33 | 0.019 | 77 | 0.054 | 83 |
| cpd 2-1 | 0.635 | 35 | 0.110 | 72 | 0.152 | 85 |
| cpd 3-1 | 0.105 | 57 | 0.035 | 79 | 0.054 | 77 |
| cpd 3-2 | 0.139 | 42 | 0.018 | 65 | 0.169 | 75 |
| cpd 4-1 | 0.064 | 47 | 0.020 | 84 | 0.016 | 92 |
| cpd 5-1 | 0.047 | 44 | 0.143 | 84 | 0.034 | 62 |
| cpd 5-2 | 0.054 | 47 | 0.021 | 72 | 0.057 | 60 |
| cpd 6-1 | 0.068 | 36 | 0.094 | 71 | 0.100 | 72 |
| cpd 6-2 | 0.026 | 38 | 0.034 | 79 | 0.131 | 66 |
| cpd 7-1 | 0.265 | 42 | 0.045 | 55 | 0.035 | 90 |
| cpd 9-1 | 0.010 | 50 | 0.011 | 77 | 0.014 | 89 |
| cpd 10-1 | 0.038 | 51 | 0.095 | 74 | 0.014 | 90 |
| cpd 10-2 | 0.030 | 43 | 0.039 | 74 | 0.024 | 73 |
| cpd 11-1 | 0.021 | 46 | 0.116 | 86 | 0.079 | 75 |
| cpd 11-2 | 0.100 | 42 | 0.023 | 87 | 0.122 | 67 |
| cpd 12-1 | 0.053 | 47 | 0.012 | 71 | 0.007 | 89 |
| cpd 12-2 | 0.090 | 37 | 0.003 | 85 | 0.013 | 78 |
| cpd 13-1 | 0.652 | 26 | 0.072 | 72 | 0.328 | 59 |
| cpd 13-2 | 0.623 | 28 | 0.009 | 71 | 0.214 | 57 |
| cpd 14-1 | 0.032 | 60 | 0.025 | 66 | 0.007 | 81 |
| cpd 14-2 | 0.041 | 58 | 0.017 | 58 | 0.03 | 74 |
| cpd 14-1-1 | 0.211 | 43 | 0.081 | 78 | 0.027 | 67 |
| cpd 14-1-2 | 0.012 | 46 | 0.011 | 82 | 0.004 | 90 |
| cpd 14-2-1 | 0.05 | 44 | 0.016 | 90 | 0.019 | 78 |
| cpd 14-2-2 | 0.017 | 44 | 0.016 | 72 | 0.059 | 57 |
| cpd 15-1 | 0.449 | 24 | 0.066 | 66 | 0.105 | 92 |
| cpd 15-2 | 0.145 | 31 | 0.046 | 69 | 0.123 | 96 |
| cpd 16-1 | 0.108 | 40 | 0.014 | 80 | 0.044 | 60 |
| cpd 16-2 | 0.05 | 50 | 0.002 | 88 | 0.012 | 71 |
| cpd 17-1 | 0.038 | 49 | 0.012 | 75 | 0.006 | 86 |
| cpd 18-1 | 0.059 | 44 | 0.026 | 84 | 0.157 | 78 |
| cpd 19-1 | 0.157 | 53 | 0.097 | 64 | 0.026 | 100 |
| cpd 20-1 | 0.143 | 50 | 0.230 | 67 | 0.087 | 84 |
| cpd 21-1 | 3.650 | 17 | 0.828 | 48 | 3.271 | 88 |

Table 7 presents $EC_{50}$ and maximal, relative activation values obtained for the representative compounds. All values were established as described in detail in materials and methods.

TABLE 8

| | AUCt (ng/mL * h) | F % | brain/plasma ratio |
|---|---|---|---|
| plasma | 71803 | 92.9 | 0.37 |
| brain | 26726 | | |

Table 8 presents selected pharmacokinetic parameters of CPD__14-1-2 in mouse. As described in materials and methods, the compound was administered either iv (2 mpk) or PO (10 mpk) and its concentration in both plasma and brain tissue were followed for 24 hours. PK data show that CPD__14-1-2 demonstrates very good bioavailability (F=93%) and as judged from the AUC comparison (brain exposure to plasma exposure ratio), a significant part (37%) of the administered compound penetrates into the brain.

TABLE 9

| | | CPD_14-1-2 (1 mpk) | CPD_14-1-2 (10 mpk) |
|---|---|---|---|
| Morris-Water maze | distance | 22.6 % +/− 21% (*) | 31.1 % +/− 18 % (**) |
| | latency | 45.6 % +/− 16 % () | 39.9 % +/− 20 % () |
| amyloid-beta peptide | Aβ 1-38 | 76 % +/− 16 % () | 97 % +/− 3 % () |
| | Aβ 1-40 | 55 % +/− 17 % () | 72 % +/− 14 % () |
| | Aβ 1-42 | 56 % +/− 19 % () | 74 % +/− 14 % () | mean reduction (%) from untreated APPPS1 mice +/− standard deviation t-test, (*) p-value < 0.05; (**) p-value < 0.01

Table 9 presents the effect of CPD__14-1-2 on both cognitive parameters (distance to localize the platform and latency to find the platform) and on the brain amyloid-beta levels that were measured in the APPPS1 transgenic mouse model for the Alzheimer's disease. APPPS1 mice were treated with CPD__14-1-2 (1 mg per kg per day or 10 mg per kg per day) for 60 days. MWM assays and amyloid-beta biochemistry were performed as described in materials and methods. Numbers in the table represent the mean reduction (%) as compared to the APPPS1 untreated mice (pathologic control) +/− standard deviation. The presented data show that the treatment with the CPD__14-1-2 provides therapeutic effects both in terms of better cognitive performance and decreased beta-amyloid accumulation in the brain.

BIBLIOGRAPHIC REFERENCES

Angione A R, et al., *PPARdelta regulates satellite cell proliferation and skeletal muscle regeneration*, Skelet Muscle, 2011, 1 (1), 33

Arora M K, et al., *The low dose combination of fenofibrate and rosiglitazone halts the progression of diabetes-induced experimental nephropathy*, Eur J Pharmacol, 2010, 636 (1-3), 137-44

Barak Y, et al., *Effects of peroxisome proliferator-activated receptor delta on placentation, adiposity, and colorectal cancer*, Proc Natl Acad Sci USA, 2002, 99 (1), 303-8

Berger J and Wagner J A, *Physiological and therapeutic roles of peroxisome proliferator-activated receptors*, Diabetes Technol Ther, 2002, 4 (2), 163-74

Bhatia V and Viswanathan P, *Insulin resistance and PPAR insulin sensitizers*, Curr Opin Investig Drugs, 2006, 7 (10), 891-7

Bocher V, et al., [*Role of the peroxisome proliferator-activated receptors (PPARS) in the regulation of lipids and inflammation control*], J Soc Biol, 2002, 196 (1), 47-52

Breidert T, et al., *Protective action of the peroxisome proliferator-activated receptor-gamma agonist pioglitazone in a mouse model of Parkinson's disease*, J Neurochem, 2002, 82 (3), 615-24

Chawla A, et al., *PPAR-gamma dependent and independent effects on macrophage-gene expression in lipid metabolism and inflammation*, Nat Med, 2001, 7 (1), 48-52

Combs C K, et al., *Inflammatory mechanisms in Alzheimer's disease: inhibition of beta-amyloid-stimulated proinflammatory responses and neurotoxicity by PPARgamma agonists*, J Neurosci, 2000, 20 (2), 558-67

Cronet P, et al., *Structure of the PPARalpha and-gamma ligand binding domain in complex with AZ 242; ligand selectivity and agonist activation in the PPAR family*, Structure, 2001, 9 (8), 699-706

Feinstein D L, *Contrasting the neuroprotective and gliotoxic effects of PPARγ agonists*, Drug Discovery Today: Therapeutic Strategies, 2004, 1 (1), 29-34

Feinstein D L, et al., *Peroxisome proliferator-activated receptor-gamma agonists prevent experimental autoimmune encephalomyelitis*, Ann Neurol, 2002, 51 (6), 694-702

Goldenberg I, et al., *Secondary prevention with bezafibrate therapy for the treatment of dyslipidemia: an extended follow-up of the BIP trial*, J Am Coll Cardiol, 2008, 51 (4), 459-65

Goldenberg I, et al., *Long-term benefit of high-density lipoprotein cholesterol-raising therapy with bezafibrate: 16-year mortality follow-up of the bezafibrate infarction prevention trial*, Arch Intern Med, 2009, 169 (5), 508-14

Heneka M T, et al., *Peroxisome proliferator-activated receptor-gamma ligands reduce neuronal inducible nitric oxide synthase expression and cell death in vivo*, J Neurosci, 2000, 20 (18), 6862-7

Hou X, et al., *PPARalpha agonist fenofibrate protects the kidney from hypertensive injury in spontaneously hypertensive rats via inhibition of oxidative stress and MAPK activity*, Biochem Biophys Res Commun, 2010, 394 (3), 653-9

Kawahito Y, et al., *15-Deoxy-Delta(12,14)-PGJ(2) Induces Synoviocyte Apoptosis and Suppresses Adjuvant-Induced Arthritis in Rats*, J Clin Invest, 2000, 106 (2), 189-97

Kitamura Y, et al., *Increased expression of cyclooxygenases and peroxisome proliferator-activated receptor-gamma in Alzheimer's disease brains*, Biochem Biophys Res Commun, 1999, 254 (3), 582-6

Kota B P, et al., *An overview on biological mechanisms of PPARs*, Pharmacol Res, 2005, 51 (2), 85-94

Lawn R M, et al., *The Tangier disease gene product ABC1 controls the cellular apolipoprotein-mediated lipid removal pathway*, J Clin Invest, 1999, 104 (8), R25-31

Lefebvre P, et al., *Sorting out the roles of PPAR alpha in energy metabolism and vascular homeostasis*, J Clin Invest, 2006, 116 (3), 571-80

Leibowitz M D, et al., *Activation of PPARdelta alters lipid metabolism in db/db mice*, FEBS Lett, 2000, 473 (3), 333-6

Letavernier E, et al., *Peroxisome proliferator-activated receptor beta/delta exerts a strong protection from ischemic acute renal failure*, J Am Soc Nephrol, 2005, 16 (8), 2395-402

Li A C, et al., *Differential inhibition of macrophage foam-cell formation and atherosclerosis in mice by PPARalpha, beta/delta, and gamma*, J Clin Invest, 2004, 114 (11), 1564-76

Lohray B B, et al., *(−)3-[4-[2-(Phenoxazin-10-yl)ethoxy]phenyl]-2-ethoxypropanoic acid [(−) DRF 2725]: a dual PPAR agonist with potent antihyperglycemic and lipid modulating activity*, J Med Chem, 2001, 44 (16), 2675-8

Lovett-Racke A E, et al., *Peroxisome proliferator-activated receptor alpha agonists as therapy for autoimmune disease*, J Immunol, 2004, 172 (9), 5790-8

Malhotra S, et al., *Potential therapeutic role of peroxisome proliferator activated receptor-gamma agonists in psoriasis*, Expert Opin Pharmacother, 2005, 6 (9), 1455-61

Murakami K, et al., *A novel insulin sensitizer acts as a coligand for peroxisome proliferator-activated receptor-alpha (PPAR-alpha) and PPAR-gamma: effect of PPAR-alpha activation on abnormal lipid metabolism in liver of Zucker fatty rats*, Diabetes, 1998, 47 (12), 1841-7

Nagasawa T, et al., *Effects of bezafibrate, PPAR pan-agonist, and GW501516, PPARdelta agonist, on development of steatohepatitis in mice fed a methionine-and choline-deficient diet*, Eur J Pharmacol, 2006, 536 (1-2), 182-91

Nagy L, et al., *Oxidized LDL regulates macrophage gene expression through ligand activation of PPARgamma*, Cell, 1998, 93 (2), 229-40

Niino M, et al., *Amelioration of experimental autoimmune encephalomyelitis in C57BL/6 mice by an agonist of peroxisome proliferator-activated receptor-gamma*, J Neuroimmunol, 2001, 116 (1), 40-8

Oliver W R, Jr., et al., *A selective peroxisome proliferator-activated receptor delta agonist promotes reverse cholesterol transport*, Proc Natl Acad Sci USA, 2001, 98 (9), 5306-11

Ouk T, et al., *Withdrawal of fenofibrate treatment partially abrogates preventive neuroprotection in stroke via loss of vascular protection*, Vascul Pharmacol, 2009, 51 (5-6), 323-30

Patel H J, et al., *Activation of peroxisome proliferator-activated receptors in human airway smooth muscle cells has a superior anti-inflammatory profile to corticosteroids: relevance for chronic obstructive pulmonary disease therapy*, J Immunol, 2003, 170 (5), 2663-9

Piqueras L, et al., *Activation of PPARbeta/delta inhibits leukocyte recruitment, cell adhesion molecule expression, and chemokine release*, J Leukoc Biol, 2009, 86 (1), 115-22

Portilla D, et al., *Etomoxir-induced PPARalpha-modulated enzymes protect during acute renal failure*, Am J Physiol Renal Physiol, 2000, 278 (4), F667-75

Sastre M, et al., *Nonsteroidal anti-inflammatory drugs and peroxisome proliferator-activated receptor-gamma agonists modulate immunostimulated processing of amyloid precursor protein through regulation of beta-secretase*, J Neurosci, 2003, 23 (30), 9796-804

Sivarajah A, et al., *Agonists of peroxisome-proliferator activated receptor-gamma reduce renal ischemia/reperfusion injury*, Am J Nephrol, 2003, 23 (4), 267-76

Storer P D, et al., *Peroxisome proliferator-activated receptor-gamma agonists inhibit the activation of microglia and astrocytes: implications for multiple sclerosis*, J Neuroimmunol, 2005, 161 (1-2), 113-22

Su C G, et al., *A novel therapy for colitis utilizing PPAR-gamma ligands to inhibit the epithelial inflammatory response*, J Clin Invest, 1999, 104 (4), 383-9

Tanaka T, et al., *Activation of peroxisome proliferator-activated receptor delta induces fatty acid beta-oxidation in skeletal muscle and attenuates metabolic syndrome*, Proc Natl Acad Sci USA, 2003, 100 (26), 15924-9

Tenenbaum A, et al., *Dual and pan-peroxisome proliferator-activated receptors (PPAR) co-agonism: the bezafibrate lessons*, Cardiovasc Diabetol, 2005, 4 14

Tenenbaum H, et al., *Long-term effect of bezafibrate on pancreatic beta-cell function and insulin resistance in patients with diabetes*, Atherosclerosis, 2007, 194 (1), 265-71

Tontonoz P and Spiegelman B M, *Fat and beyond: the diverse biology of PPARgamma*, Annu Rev Biochem, 2008, 77 289-312

Walczak R and Tontonoz P, *PPARadigms and PPARadoxes: expanding roles for PPARgamma in the control of lipid metabolism*, J Lipid Res, 2002, 43 (2), 177-86

Wang G, et al., *Chronic treatment with fibrates elevates superoxide dismutase in adult mouse brain microvessels*, Brain Res, 2010, 1359 247-55

Wang Y X, et al., *Peroxisome-proliferator-activated receptor delta activates fat metabolism to prevent obesity*, Cell, 2003, 113 (2), 159-70

Youssef J and Badr M, *Role of Peroxisome Proliferator-Activated Receptors in Inflammation Control*, J Biomed Biotechnol, 2004, 2004 (3), 156-166

The invention claimed is:

1. A compound, derived from 1,3-diphenylpropane, having the general formula (I):

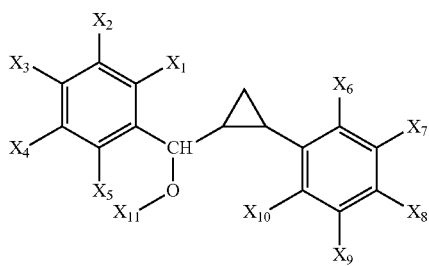

in which:
$X_1$ represents a halogen atom, a hydrogen atom, an R1 group or G1-R1 group;
$X_2$ represents a halogen atom, a hydrogen atom, an R2 group or G2-R2 group;
$X_3$ represents a halogen atom, a hydrogen atom, an R3 group or G3-R3 group;
$X_4$ represents a halogen atom, a hydrogen atom, an R4 group or G4-R4 group;
$X_5$ represents a halogen atom, a hydrogen atom, an R5 group or G5-R5 group;
$X_6$, $X_7$, $X_9$ and $X_{10}$, which can be identical or different, represent a halogen atom, a hydrogen atom, or an alkyl group; and
$X_8$ represents a G8-R8 group;
wherein R1, R2, R3, R4 and R5, which can be identical or different, represent an alkyl group or a halogenated alkyl group;
R8 represents an alkyl group substituted by at least one COOR12 group;
R12 represents a hydrogen atom or an alkyl group;
G1, G2, G3, G4, G5, and G8, which can be identical or different, represent an oxygen atom or a sulfur atom; and
$X_{11}$ represents an alkyl group, optionally substituted by an aryl or a cycloalkyl group.

2. The compound according to claim 1, wherein when at least one of $X_1$, $X_2$, $X_3$, $X_4$ and $X_5$ represents R1, R2, R3, R4 or R5, respectively, then said R1, R2, R3, R4 or R5 is optionally halogenated C1-C4, an alkyl group, a methyl group or a trifluoromethyl group.

3. The compound according to claim 1, wherein when at least one of $X_1$, $X_2$, $X_3$, $X_4$ and $X_5$ represents G1-R1, G2-R2, G3-R3, G4-R4 or G5-R5, respectively, then said R1, R2, R3, R4 or R5 is an optionally halogenated C1-C4, an alkyl group, a methyl group or a trifluoromethyl group.

4. The compound according to claim 1, wherein at least three or four X5 out of the $X_1$, $X_2$, $X_3$, $X_4$ and $X_5$ groups are hydrogen atoms, or $X_2$, $X_4$ and $X_5$ are hydrogen atoms or $X_1$, $X_2$, $X_4$ and $X_5$ are hydrogen atoms.

5. The compound according to claim 1, wherein the $X_1$, $X_2$, $X_3$, $X_4$ and $X_5$ groups represent R1, R2, R3, R4 and R5, respectively, and said R1, R2, R3, R4 and R5 are optionally halogenated C1-C4, alkyl groups, methyl groups or trifluoromethyl groups.

6. The compound according to claim 1, wherein $X_3$ represents a halogen atom, R3 or a G3-R3 group, $X_1$ represents a halogen atom or a hydrogen atom, and $X_2$, $X_4$ and $X_5$ are hydrogen atoms.

7. The compound according to claim 1, wherein $X_1$ represents a halogen atom, R1 or a G1-R1 group, $X_3$ represents a halogen atom or a hydrogen atom, and $X_2$, $X_4$ and $X_5$ are hydrogen atoms.

8. The compound according to claim 1, wherein $X_6$, $X_7$, $X_9$ and $X_{10}$ independently represent a hydrogen atom, a halogen atom or an alkyl group, with at least one of $X_7$ and $X_9$ not being a hydrogen atom.

9. The compound according to claim 1, wherein R8 is a linear or branched (C1-C4)alkyl or R8 is —CH(CH$_3$)-, or —C(CH$_3$)$_2$-.

10. The compound according to claim 1, wherein $X_{11}$ is a hydrogen atom or a linear or branched ($C_1$-$C_4$)alkyl, optionally substituted by an aryl group or a cycloalkyl group.

11. The compound according to claim 1, wherein the compound is selected from:
2-(4-(2-(methoxy(4-bromophenyl)methyl)cyclopropyl)-2,6-dimethylphenoxy)-2-methylpropanoic acid;
2-(4-(2-(methoxy(4-methylphenyl)methyl)cyclopropyl)-2,6-dimethylphenoxy)-2-methylpropanoic acid;
2-(4-(2-(methoxy(4-(methylthio)phenyl)methyl)cyclopropyl)-2,6-dimethylphenoxy)-2-methylpropanoic acid;
2-(4-(2-(methoxy(4-(trifluoromethyl)phenyemethyl)cyclopropyl)-2,6-dimethylphenoxy)-2-methylpropanoic acid;
2-(4-(2-(butyloxy(4-(trifluoromethoxy)phenyl)methyl)cyclopropyl)-2,6-dimethylphenoxy)-2-methylpropanoic acid;
2-(4-(2-(cyclohexylethyloxy(4-(trifluoromethoxy)phenyl)methyl)cyclopropyl)-2,6-dimethylphenoxy)-2-methylpropanoic acid;
2-(4-(2-(methoxy(4-(trifluoromethoxy)phenyl)methyl)cyclopropyl)-2-methylphenoxy)-2-methylpropanoic acid;
2-(4-(2-(methoxy(4-(propyloxy)phenyl)methyl)cyclopropyl)-2,6-dimethylphenoxy)-2-methylpropanoic acid;
2-(4-(2-(methoxy(4-(trifluoromethylthio)phenyl)methyl)cyclopropyl)-2,6-dimethylphenoxy)-2-methylpropanoic acid;
2-(4-(2-(ethoxy(4-(trifluoromethoxy)phenyl)methyl)cyclopropyl)-2,6-dimethylphenoxy)-2-methylpropanoic acid;
2-(4-(2-(benzyloxy(4-(trifluoromethoxy)phenyl)methyl)cyclopropyl)-2,6-dimethylphenoxy)-2-methylpropanoic acid;
2-(4-(2-(methoxy(2-fluoro-4-(trifluoromethyl)phenyl)methyl)cyclopropyl)-2,6-dimethylphenoxy)-2-methylpropanoic acid;

2-(4-(2-(methoxy(2-(trifluoromethyloxy)phenyl)methyl)cyclopropyl)-2,6-dimethylphenoxy)-2-methylpropanoic acid;

2-(4-(2-(methoxy(4-(trifluoromethoxy)phenyl)methyl)cyclopropyl)-2,6-dimethylphenoxy)-2-methylpropanoic acid;

2-(2-isopropyl-4-(2-(methoxy(4-(trifluoromethoxy)phenyl)methyl)cyclopropyl)phenoxy)-2-methylpropanoic acid;

2-(4-(2-((2,4-bis(trifluoromethyl)phenyl)(methoxy)methyl)cyclopropyl)-2,6-dimethylphenoxy)-2-methylpropanoic acid;

2-(4-(2-(methoxy(2-methoxy-4-(trifluoromethoxy)phenyl)methyl)cyclopropyl)-2,6-dimethylphenoxy)-2-methylpropanoic acid;

2-(4-(2-((2-(hexyloxy)phenyl)(methoxy)methyl)cyclopropyl)-2,6-dimethylphenoxy)-2-methylpropanoic acid;

2-(2-bromo-4-(2-(methoxy(4-(trifluoromethoxy)phenyl)methyl)cyclopropyl)phenoxy)-2-methylpropanoic acid;

2-(2,6-difluoro-4-(2-(methoxy(4-(trifluoromethoxy)phenyl)methyl)cyclopropyl)phenoxy)-2-methylpropanoic acid; or 2-(2-cyclopropyl-4-(2-(methoxy(4-(trifluoromethoxy)phenyl)methyl)cyclopropyl)phenoxy)-2-methylpropanoic acid.

12. The compound according to claim 1, wherein the compound is 2-(4-(2-(methoxy(4-(trifluoromethoxy)phenyl)methyl)cyclopropyl)-2,6-dimethylphenoxy)-2-methylpropanoic acid.

13. A pharmaceutical composition comprising, in a pharmaceutically acceptable support, at least one of the compounds as defined in claim 1.

14. A method for the treatment of a metabolic and/or inflammatory disease, the method comprising administering a compound according to claim 1 to a subject in need thereof.

15. The method according to claim 14, wherein said disease is selected from overweight condition, bulimia, anorexia nervosa, hyperlipidemia, dyslipidemia, hypoalphalipoproteinemia, hypertriglyceridemia, hypercholesterolemia, low HDL, metabolic syndrome, non-alcoholic fatty liver disease (NAFLD), non-alcoholic steatohepatitis (NASH), diseases associated with hepatic fibrosis, such as primary biliary cirrhosis, viral hepatitis, or drug-induced hepatitis, alcoholic liver disease, type 2 diabetes, type 1 diabetes, hyperinsulinemia, impaired glucose tolerance, insulin resistance, a diabetic complication of neuropathy, nephropathy, retinopathy, diabetic foot ulcer or cataracts, hypertension, coronary heart disease, heart failure, congestive heart failure, atherosclerosis, arteriosclerosis, stroke, cerebrovascular disease, myocardial infarction, peripheral vascular disease, vitiligo, uveitis, pemphigus foliaceus, inclusion body myositis, polymyositis, dermatomyositis, scleroderma, Graves' disease, Hashimoto's disease, chronic graft versus host disease, rheumatoid arthritis, inflammatory bowel syndrome, Crohn's disease, systemic lupus erythematosis, Sjögren's syndrome, multiple sclerosis, asthma, chronic obstructive pulmonary disease, polycystic kidney disease, polycystic ovary syndrome, pancreatitis, nephritis, hepatitis, eczema, psoriasis, dermatitis, impaired wound healing, Alzheimer's disease, Parkinson's disease, amyotrophic lateral sclerosis, spinal cord injury, acute disseminated encephalomyelitis, Guillain-Barré syndrome, thrombosis, infarction of the large or small intestine, renal insufficiency, erectile dysfunction, urinary incontinence, neurogenic bladder, ophthalmic inflammation, macular degeneration, pathologic neovascularization, HCV infection, HIV infection, and *Helicobacter pylori* infection.

16. The method according to claim 14, wherein the metabolic or inflammatory disease is diabetes.

17. A method for the treatment of a neurodegenerative disorder, comprising administering a compound according to claim 1 to a subject in need thereof.

18. The method according to claim 17, wherein the neurodegenerative disorder is Alzheimer's disease, Parkinson's disease or multiple sclerosis.

\* \* \* \* \*